(12) United States Patent
Rho et al.

(10) Patent No.: US 12,269,851 B2
(45) Date of Patent: Apr. 8, 2025

(54) POLYPEPTIDE AND METHOD OF PRODUCING IMP USING THE SAME

(71) Applicant: CJ CHEILJEDANG CORPORATION, Seoul (KR)

(72) Inventors: Jin Ah Rho, Suwon-si (KR); Byoung Hoon Yoon, Seoul (KR); So-Jung Park, Suwon-si (KR); Min Ji Baek, Suwon-si (KR); Ji Hye Lee, Anyang-si (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 130 days.

(21) Appl. No.: 18/059,581

(22) Filed: Nov. 29, 2022

(65) Prior Publication Data

US 2023/0192780 A1    Jun. 22, 2023

Related U.S. Application Data

(62) Division of application No. 17/833,539, filed on Jun. 6, 2022, now Pat. No. 11,746,130, which is a division of application No. 16/346,725, filed as application No. PCT/KR2019/000168 on Jan. 4, 2019, now Pat. No. 11,384,124.

(30) Foreign Application Priority Data

Jan. 4, 2018 (KR) .................. 10-2018-0001399

(51) Int. Cl.
*C07K 14/34* (2006.01)
*C12N 1/20* (2006.01)
*C12P 19/32* (2006.01)
*C12R 1/15* (2006.01)

(52) U.S. Cl.
CPC ............. *C07K 14/34* (2013.01); *C12N 1/20* (2013.01); *C12N 1/205* (2021.05); *C12P 19/32* (2013.01); *C12R 2001/15* (2021.05)

(58) Field of Classification Search
CPC .......... C07K 14/34; C12N 1/20; C12N 1/205; C12N 15/77; C12P 19/32; C12P 19/40
See application file for complete search history.

(56) References Cited

U.S. PATENT DOCUMENTS

| 7,767,626 | B2 | 8/2010 | Toriyabe et al. |
| 9,271,500 | B2 | 3/2016 | Takahashi et al. |
| 9,783,509 | B2 | 10/2017 | Alig et al. |
| 9,802,930 | B1 | 10/2017 | Tanabe et al. |
| 9,924,719 | B2 | 3/2018 | Tanabe et al. |
| 10,039,282 | B2 | 8/2018 | Wo et al. |
| 2020/0377558 | A1 | 12/2020 | Rho |

FOREIGN PATENT DOCUMENTS

| EP | 3 608 410 A1 | 2/2020 |
| JP | 2-88570 A | 3/1990 |
| KR | 2003-0042972 A | 6/2003 |
| KR | 10-2007-0060207 A | 6/2007 |
| KR | 10-2007-0060208 A | 6/2007 |
| KR | 10-2010-0109732 A | 10/2010 |
| KR | 10-1744958 B1 | 6/2017 |
| KR | 10-1916622 B1 | 11/2018 |
| WO | 99/55668 A1 | 11/1999 |
| WO | 2010/100189 A1 | 9/2010 |
| WO | 2013/191113 A1 | 12/2013 |
| WO | 2015/004028 A1 | 1/2015 |
| WO | 2015/091267 A1 | 6/2015 |
| WO | 2016/052247 A1 | 4/2016 |
| WO | 2016/052455 A1 | 4/2016 |

OTHER PUBLICATIONS

Adrio et al., "Genetic improvement of processes yielding microbial products," *FEMS Microbiol Rev* 30:187-214 (2006).
European Nucleotide Archive, AMJ44984, Corynebacterium stationis MFS transporter, 2 pages, Feb. 18, 2016.
GenBank Accession No. WP_066795119, retrieved May 24, 2019, from https://www.ncbi.nlm.nih.gov/protein/WP_066795119.1/.
GenBank: ASJ19118.1, "transcriptional regulator [Corynebacterium stationis]," (two pages) Jul. 5, 2017.
Ishii et al., "Improved Inosine Production and Derepression of Purine Nucleotide Biosynthetic Enzymes in 8-Azaguanine Resistant Mutants of *Bacillus subtilis*," Agr. Biol. Chem. 36(9):1511-1522 (1972).
Kisselev, "Polypeptide Release Factors in Prokaryotes and Eukaryotes: Same Function, Different Structure," *Structure* 10:8-9 (2002).
Ledesma-Amaro et al., "Biotechnological production of feed nucleotides by microbial strain improvement," *Process Biochemistry*, http://dx.doi.org/10.1016/j.procbio.2013.06.025, 8 pages (2013).
MFS transporter [Corynebacterium stationis]—GenBank: AMJ44984. 1, Feb. 16, 2016.
Mori et al., "A novel process of inosine 5'-monophosphate production using overexpressed guanosine/inosine kinase," Appl Microbiol Biotechnol, 48:693-698, 1997, 6 pages.
NCBI Reference Sequence WP_066795121.1, retrieved from https://www.ncbi.nlm.nih.gov/protein/WP_066795121.1/ on May 24, 2019.
Parkhill et al., "Complete genome sequence of a multiple drug resistant *Salmonella enterica* serovarTyphi CT18," Nature 413:848-852 (2001).
Peifer et al., "Metabolic engineering of the purine biosynthetic pathway in Corynebacterium glutamicum results in increased intracellular pool sizes of IMP and hypoxanthine," Microbial Cell Factories, 11:138, 2012, 14 pages.
Sanchez et al., "Metabolic regulation and overproduction of primary metabolites," *Microbiol Biotechnology* 1(4):283-319 (2008).

(Continued)

*Primary Examiner* — Iqbal H Chowdhury
(74) *Attorney, Agent, or Firm* — Seed IP Law Group LLP

(57) ABSTRACT

The present disclosure relates to a novel protein variant having an activity of exporting 5'-inosine monophosphate, a microorganism comprising the protein variant, and a method for preparing 5'-inosine monophosphate using the microorganism.

4 Claims, No Drawings
Specification includes a Sequence Listing.

(56) References Cited

OTHER PUBLICATIONS

UniProt Accession No. A0A0F0LG81 (Multidrug resistance protein 3) created Jun. 24, 2015.
UniProtKB—A0A241TXB3_9CORY, Transcriptional regulator, 4 pages, Oct. 25, 2017.
Whisstock et al., "Prediction of protein function from protein sequence and structure," *Quarterly Reviews of Biophysics* 36(3):307-340 (2003).
Witkowski et al., "Conversion of a β-Ketoacyl Synthase to a Malonyl Decarboxylase by Replacement of the Active-Site Cysteine with Glutamine," *Biochemistry* 38:11643-11650 (1999).

POLYPEPTIDE AND METHOD OF PRODUCING IMP USING THE SAME

CROSS REFERENCE TO RELATED APPLICATIONS

The present application is a divisional application of U.S. application Ser. No. 17/833,539 filed Jun. 6, 2022, which is a divisional application of U.S. application Ser. No. 16/346,725 filed May 1, 2019, now U.S. Pat. No. 11,384,124, which is a U.S. national phase application of PCT/KR2019/000168 filed Jan. 4, 2019, which claims priority to KR Application No. 10-2018-0001399 filed Jan. 4, 2018. U.S. application Ser. Nos. 16/346,725 and 17/833,539 are herein incorporated by reference their entireties.

REFERENCE TO AN ELECTRONIC SEQUENCE LISTING

The contents of the electronic sequence listing (200187_442D2_SEQUENCE_LISTING.xml; Size: 280,570 bytes; and Date of Creation: Nov. 11, 2022) is herein incorporated by reference in its entirety.

TECHNICAL FIELD

The present disclosure relates to a novel protein variant having an activity of exporting 5'-inosine monophosphate, a microorganism containing the protein variant, a method for preparing 5'-inosine monophosphate using the microorganism, and a method for increasing export of 5'-inosine monophosphate using the microorganism.

BACKGROUND ART

5'-Inosine monophosphate (hereinafter, IMP), a nucleic acid material, is an intermediate of the nucleic acid metabolic pathway and is used in many fields such as foods, medicines, various medical applications, etc. In particular, IMP is widely used as an additive for food seasonings or foods, along with 5'-guanine monophosphate (hereinafter, GMP). Although IMP itself is known to provide a beef taste, it is known to enhance the flavor of monosodium glutamic acid (MSG) and is thus attracting attention as a taste-enhancing nucleic acid-based seasoning.

Examples of methods for producing IMP include a method of enzymatically degrading ribonucleic acid extracted from yeast cells (Japanese Patent Publication No. 1614/1957), a method for chemically phosphorylating inosine produced by fermentation (*Agri. Biol. Chem.*, 36, 1511, (1972), etc.), a method for culturing microorganisms which can directly produce IMP and recovering IMP in the culture broth, etc. Among these, the method most frequently used at present is a method using microorganisms capable of directly producing IMP.

Meanwhile, since enzymes do not always exhibit optimal properties in nature with respect to activity, stability, substrate specificity for optical isomers, etc. required in industrial applications, various attempts have been made to improve enzymes to suit the intended use by a mutation of their amino acid sequences, etc. Among these, although rational design and site-directed mutagenesis of enzymes have been applied to improve enzyme function, in many cases, these attempts were shown to be disadvantageous in that information on the structure of target enzymes is not sufficient or the structure-function correlation is not clear, thus preventing their effective application. Additionally, a method of improving enzyme activity by attempting the enhancement of enzymes through directed evolution, which is for screening enzymes of desired traits from a library of modified enzymes constructed through random mutagenesis of enzyme genes, was previously reported.

DISCLOSURE

Technical Problem

To produce IMP in high yield by direct IMP production through microbial fermentation, it is essential that the IMP export be smoothly performed. To achieve the object of the present disclosure, the inventors of the present disclosure have conducted extensive studies, and as a result, have identified the proteins involved in the activity of exporting IMP and have also discovered protein variants having higher activity of exporting IMP, thereby completing the present disclosure.

Technical Solution

An object of the present disclosure is to provide a protein variant having the activity of exporting IMP.

Another object of the present disclosure is to provide a polynucleotide encoding the protein variant of the present disclosure.

Still another object of the present disclosure is to provide a vector including the polynucleotide of the present disclosure.

Still another object of the present disclosure is to provide a microorganism producing IMP, in which the microorganism includes the protein variant of the present disclosure and the vector of the present disclosure.

Still another object of the present disclosure is to provide a method for preparing IMP, which includes culturing the microorganism of the genus *Corynebacterium* of the present disclosure in a medium, and recovering IMP from the microorganism or the medium.

Still another object of the present disclosure is to provide a method for increasing export of IMP, which includes a step of enhancing an activity of the protein exporting IMP in a microorganism of the genus *Corynebacterium*.

To achieve the above objects, an aspect of the present disclosure provides a protein variant having an activity of exporting IMP.

As used herein, the term "a protein that exports 5'-inosine monophosphate (IMP)" refers to a protein involved in the extracellular export of IMP. For the purpose of the present disclosure, the term may be used interchangeably with a protein having an activity of exporting IMP, an IMP export protein, a protein capable of exporting IMP, an IMP-exporting protein, etc.; specifically, the protein may be expressed as ImpE, more specifically, ImpE1 or ImpE2, and even more specifically, the protein that exports of the present disclosure may be expressed as ImpE2, but the expression of the protein is not limited thereto. Additionally, the protein may be derived from a microorganism of the genus *Corynebacterium*, and specifically from *Corynebacterium stationis*, but the microorganism is not limited thereto.

The protein may be a protein which includes the amino acid sequence represented by SEQ ID NO: 2 or one which consists of the amino acid sequence represented by SEQ ID NO: 2, but any sequence having the same activity as the protein can be included without limitation, and one of ordinary skill in the art can obtain sequence information from GenBank of NCBI, a well-known database. Additionally, the protein of the present disclosure that exports IMP may be a protein which includes an amino acid sequence of SEQ ID NO: 2, or an amino acid sequence which has a homology or identity to the sequence of SEQ ID NO: 2 of at least 80%, at least 90%, at least 95%, at least 96%, at least 97%, at least 98%, or at least 99%. Additionally, it is apparent that any protein having an amino acid sequence with deletion, mutation, substitution, or addition in part of the sequence can also be included in the scope of the present disclosure, as long as the amino acid sequence has a homology or identity described above and has an effect corresponding to that of the protein.

That is, although described as "a protein having an amino acid sequence represented by a particular SEQ ID NO" or "a protein consisting of a particular SEQ ID NO" in the present disclosure, it is apparent that a protein having an amino acid sequence with deletion, modification, substitution, conservative substitution, or addition of some amino acids also falls within the scope of the present invention as long as the protein has an activity the same as or equivalent to that of the protein which consists of an amino acid sequence of the corresponding SEQ ID NO. For example, insofar as the protein has an activity the same as or equivalent to that of the protein variant of the present disclosure, the above expression does not exclude a sequence addition upstream or downstream of the amino acid sequence that does not alter the functions of the protein, a naturally occurring mutation therein, a silent mutation therein, or conservative substitution, and even in a case of such a sequence addition or mutation, it is apparent that the protein also belongs to the scope of the present disclosure.

In the present disclosure, "homology" and "identity" refer to a degree of relevance between two given amino acid sequences or nucleotide sequences, and may be expressed as a percentage.

The terms "homology" and "identity" are often used interchangeably with each other.

The sequence homology or identity of conserved polynucleotide or polypeptide sequences may be determined by standard alignment algorithms and may be used with default gap penalty established by the program being used. Substantially, homologous or identical polynucleotides or polypeptides can generally hybridize under moderate or high stringency, along the entire length or at least about 50%, about 60%, about 70%, about 80%, or about 90% or higher of the entire length. In the hybridization, polynucleotides that include degenerate codons instead of codons are also considered.

Whether any two polynucleotide or polypeptide sequences have a homology, similarity, or identity may be determined, for example, using a known computer algorithm such as the "FASTA" program (e.g., Pearson et al., (1988) *Proc. Natl. Acad. Sci. USA* 85: 2444) using default parameters. Alternatively, it may be determined using the Needleman-Wunsch algorithm (Needleman and Wunsch, 1970, *J Mol. Biol.* 48: 443-453), which is performed in the Needleman program of the EMBOSS package (EMBOSS: The European Molecular Biology Open Software Suite, Rice et al., 2000, *Trends Genet.* 16: 276-277) (version 5.0.0 or versions thereafter) (GCG program package (Devereux, J., et al., *Nucleic Acids Research* 12: 387 (1984)), BLASTP, BLASTN, FASTA (Atschul, [S.] [F.] et al., *J Molec Bio* 215]: 403 (1990); Guide to Huge Computers, Martin J. Bishop, [ED.,] Academic Press, San Diego, 1994, and [CARILLO ETA/.](1988) SIAM *J Applied Math* 48: 1073). For example, the homology, similarity, or identity may be determined using BLAST or ClustalW of the National Center for Biotechnology Information (NCBI).

The homology, similarity, or identity of polynucleotide or polypeptide sequences may be determined by comparing sequence information using, for example, the GAP computer program (e.g., Smith and Waterman, *Adv. Appl. Math* (1981) 2:482) as published. In summary, the GAP program defines the homology or identity as the value obtained by dividing the number of similarly aligned symbols (i.e. nucleotides or amino acids) by the total number of the symbols in the shorter of the two sequences. Default parameters for the GAP program may include (1) a unary comparison matrix (containing a value of 1 for identities and 0 for non-identities) and the weighted comparison matrix of Gribskov et al. (1986), *Nucl. Acids Res.* 14: 6745, as disclosed in Schwartz and Dayhoff, eds., *Atlas of Protein Sequence and Structure*, National Biomedical Research Foundation, pp. 353-358, 1979; (2) a penalty of 3.0 for each gap and an additional 0.10 penalty for each symbol in each gap (or a gap opening penalty of 10 and a gap extension penalty of 0.5); and (3) no penalty for end gaps. Accordingly, as used herein, the term "homology" or "identity" refers to relevance between sequences.

As used herein, the term "variant" refers to a polypeptide which, in conservative substitution and/or modification of one or more amino acids, differs from the recited sequence but retains the functions or properties of the protein. A variant differs from identified sequences being distinguished by several amino acid substitutions, deletions, or additions. Such variant may generally be identified by modifying one amino acid of the polypeptide sequence and evaluating the properties of the variant. That is, the abilities of the variant protein may be increased, unaltered, or decreased compared to those of the native protein. In addition, some modified polypeptides may include modified ones in which one or more moieties (e.g., a N-terminal leader sequence, transmembrane domain, etc.) are removed. Other variants may include variants in which a small portion has been removed from the N- and/or C-terminal of the mature protein. As used herein, the term "conservative substitution" refers to replacement of an amino acid with another amino acid having similar structural and/or chemical properties. The variant may have, for example, one or more conservative substitutions while still retaining one or more biological activities. Such amino acid substitution may be generally made on the basis of similarity in polarity, charge, solubility, hydrophobicity, hydrophilicity, and/or amphipathic nature. For example, positively charged (basic) amino acids include arginine, lysine, and histidine; and negatively charged (acidic) amino acids include glutamic acid and aspartic acid; aromatic amino acids include phenylalanine, tryptophan, and tyrosine; and hydrophobic amino acids include alanine, valine, isoleucine, leucine, methionine, phenylalanine, proline, glycine, and tryptophan.

Additionally, the variant may also include deletion or addition of amino acids, which have minimal effects on properties and a secondary structure of a polypeptide. For example, the polypeptide may be conjugated to a signal (or leader) sequence at the N-terminus of a protein that is involved in the co-translational or post-translational transfer of the protein. The polypeptide may also be conjugated to another sequence or linker to enable identification, purification, or synthesis of the polypeptide.

Specifically, the protein variant having the activity of exporting IMP of the present disclosure may be a protein variant having an amino acid sequence, in which, from the N-terminus in the amino acid sequence of SEQ ID NO: 2, at least one amino acid selected from the group consisting of the 123$^{rd}$ amino acid, the 243$^{rd}$ amino acid, the 387$^{th}$ amino acid, the 405$^{th}$ amino acid; the 413$^{th}$ amino acid, and the 458$^{th}$ amino acid is substituted with another amino acid, but the amino acid substitution is not limited thereto.

For example, the protein variant having the activity of exporting IMP of the present disclosure may be a protein variant having the IMP-exporting activity may be one which has, from the N-terminus in the amino acid sequence of SEQ ID NO: 2, a substitution of the 123$^{rd}$ amino acid with cysteine (i.e., F123C); a substitution of the 243$^{rd}$ amino acid with valine (i.e., I243V); a substitution of the 387$^{th}$ amino acid with threonine (i.e., S387T); a substitution of the 405$^{th}$ amino acid with tyrosine (i.e., F405Y); a substitution of the 413$^{th}$ amino acid with threonine (i.e., M413T); a substitution of the 458$^{th}$ amino acid with lysine (i.e., N458K); or a combination thereof, but the amino acid substitution is not limited thereto. More specifically, the protein variant having an activity of exporting IMP may be a protein, which has an amino acid sequence selected from the group consisting of SEQ ID NOS: 73, 74, 75, 76, 77, 78, 101, 103, 105, 107, 109, 111, 113, 115, 117, 119, 121, 123, 125, 127, 129, 131, 133, 135, 137, 139, 141, 143, 145, 147, 149, 151, 153, and 155, or an amino acid sequence having a homology of at least 80%, at least 90%, at least 95%, at least 96%, at least 97%, at least 98%, or at least 99% or higher to these amino acid sequences. Additionally, it is apparent that any protein having an amino acid sequence, in which part of the amino acid sequence is deleted, modified, substituted, or added, can also be used as the protein of the present disclosure, as long as the amino acid sequence has the sequence homology described above and shows an effect equivalent to those of the above polypeptides.

Additionally, the protein variant having the activity of exporting IMP of the present disclosure may be a protein variant consisting of an amino acid sequence, which further includes, from the N-terminus in the amino acid sequence of SEQ ID NO: 2, a substitution of the 2$^{nd}$ amino acid with another amino acid, a substitution of the 64$^{th}$ amino acid with another amino acid, or a combination thereof. Specifically, the protein variant having the activity of exporting IMP of the present disclosure may be a protein variant, which further includes, from the N-terminus in the amino acid sequence of SEQ ID NO: 2, a substitution of the 2$^{nd}$ amino acid with isoleucine, a substitution of the 64$^{th}$ amino acid with glutamic acid or aspartate, or a combination thereof.

The "substitution with another amino acid" is not limited as long as the other amino acid is an amino acid different from the amino acid before the substitution. For example, when the 2$^{nd}$ amino acid from the N-terminus in the amino acid sequence of SEQ ID NO: 2 is substituted with another amino acid, the other amino acid is not limited as long as the other amino acid is an amino acid other than valine, and when the 64$^{th}$ amino acid from the N-terminus in the amino acid sequence of SEQ ID NO: 2 is substituted with another amino acid, the other amino acid is not limited as long as the other amino acid is an amino acid other than glycine.

Another aspect of the present disclosure provides a polynucleotide encoding the protein variant of the present disclosure, or a vector containing the polynucleotide of the present disclosure.

As used herein, the term "polynucleotide" refers to a polymer of nucleotides in which nucleotide monomers are extended in a long chain by covalent bonds and which has a DNA strand or RNA strand longer than a certain length.

With regard to the polynucleotide of the present disclosure, based on codon degeneracy, it is apparent that the proteins which consist of the amino acid sequence of SEQ ID NO: 73, 74, 75, 76, 77, 78, 101, 103, 105, 107, 109, 111, 113, 115, 117, 119, 121, 123, 125, 127, 129, 131, 133, 135, 137, 139, 141, 143, 145, 147, 149, 151, 153, or 155, or polynucleotides which can be translated into proteins having a homology to the above proteins, can also be included in the scope of the present disclosure. For example, the polynucleotide of the present disclosure may be a polynucleotide sequence having the base sequence of SEQ ID NO: 79, 80, 81, 82, 83, 84, 102, 104, 106, 108, 110, 112, 114, 116, 118, 120, 122, 124, 126, 128, 130, 132, 134, 136, 138, 140, 142, 144, 146, 148, 150, 152, 154, or 156, and more specifically, a polynucleotide consisting of the base sequence of SEQ ID NO: 79, 80, 81, 82, 83, 84, 102, 104, 106, 108, 110, 112, 114, 116, 118, 120, 122, 124, 126, 128, 130, 132, 134, 136, 138, 140, 142, 144, 146, 148, 150, 152, 154, or 156. Additionally, any sequence which encodes a protein that has an activity of the protein having an amino acid sequence of SEQ ID NO: 73, 74, 75, 76, 77, 78, 101, 103, 105, 107, 109, 111, 113, 115, 117, 119, 121, 123, 125, 127, 129, 131, 133, 135, 137, 139, 141, 143, 145, 147, 149, 151, 153, or 155, determined by hybridization under stringent conditions with a probe that can be prepared from a known gene sequence (e.g., a sequence complementary to all or part of the above nucleotide sequences), can be included without limitation.

The term "stringent conditions" refers to conditions under which specific hybridization between polynucleotides is made possible. Such conditions are specifically described in references (e.g., J. Sambrook et al., supra). For example, the conditions may include performing hybridization between genes having a high homology, a homology of 40% or higher, specifically 90% or higher, more specifically 95% or higher, even more specifically 97% or higher, and most specifically 99% or higher, while not performing hybridization between genes having a homology of lower than the above homologies; or to perform hybridization once, specifically two or three times, under conventional washing conditions for southern hybridization of 60° C., 1×SSC, and 0.1% SDS, specifically at a salt concentration and temperature corresponding to 60° C., 0.1×SSC, and 0.1% SDS, and more specifically 68° C., 0.1×SSC, and 0.1% SDS.

Hybridization requires that two nucleic acids have a complementary sequence, although mismatches between bases may be possible depending on the stringency of the hybridization. The term "complementary" is used to describe the relationship between mutually hybridizable nucleotide bases. For example, with respect to DNA, adenosine is complementary to thymine, and cytosine is complementary to guanine. Accordingly, the present disclosure may also include isolated nucleic acid fragments complementary to the entire sequence as well as substantially similar nucleic acid sequences.

Specifically, polynucleotides having a homology can be detected at a Tm value of 55° C. using hybridization conditions that include a hybridization step and using the conditions described above. Additionally, the Tm value may be 60° C., 63° C., or 65° C., but is not limited thereto and may be appropriately adjusted by an ordinary person skilled in the art according to the intended purpose.

The stringency suitable for the hybridization of polynucleotides depends on the length and complementarity of the polynucleotides and the related variables are well known in the art (see Sambrook et al., supra, 9.50 to 9.51 and 11.7 to 11.8).

In the present disclosure, the polynucleotide which encodes the amino acid sequence of the protein having an IMP-exporting activity may be impE2 gene, and the explanation of the polynucleotide is as described above.

In the present disclosure, the explanation of the polynucleotide encoding the protein variant, which has an IMP-exporting activity, is also as described above.

As used herein, the term "vector" refers to a DNA construct including the nucleotide sequence of the polynucleotide encoding a target protein, in which the target protein is operably linked to a suitable control sequence so that the target protein can be expressed in an appropriate host. The control sequence may include a promoter capable of initiating transcription, any operator sequence for controlling the transcription, a sequence encoding an appropriate mRNA ribosome-binding domain, and a sequence controlling the termination of transcription and translation. The vector, after being transformed into a suitable host cell, may be replicated or function irrespective of the host genome, or may be integrated into the host genome itself.

The vector used in the present disclosure may not be particularly limited as long as the vector is replicable in the host cell, and it may be constructed using any vector known in the art. Examples of the vector may include natural or recombinant plasmids, cosmids, viruses, and bacteriophages. For example, as a phage vector or cosmid vector, pWE15, M13, MBL3, MBL4, IXII, ASHII, APII, t10, t11, Charon4A, Charon21A, etc. may be used; and as a plasmid vector, those based on pBR, pUC, pBluescriptll, pGEM, pTZ, pCL, pET, etc. may be used. Specifically, pDZ, pACYC177, pACYC184, pCL, pECCG117, pUC 19, pBR322, pMW118, pCC1BAC vectors, etc. may be used.

In an embodiment, the polynucleotide encoding the target protein may be replaced with a modified polynucleotide (variant) within the chromosome using a vector for the insertion into the chromosome in a cell. The insertion of the polynucleotide into the chromosome may be performed using a known method in the art, for example, by homologous recombination, but is not limited thereto. In particular, a selection marker for confirming the insertion into the chromosome may be further included. The selection marker is used for selection of a transformed cell, i.e., in order to confirm whether the target nucleic acid has been inserted, and markers capable of providing selectable phenotypes such as drug resistance, nutrient requirement, resistance to cytotoxic agents, and expression of surface proteins may be used. Under the circumstances where selective agents are treated, only the cells capable of expressing the selection markers can survive or express other phenotypic traits, and thus the transformed cells can be easily selected.

Still another aspect of the present disclosure provides a microorganism which can produce IMP that includes the protein variant of the present disclosure, a polynucleotide encoding the protein variant of the present disclosure, or the vector of the present disclosure. Specifically, the microorganism of the present disclosure may be a microorganism prepared by transformation using a vector containing the polynucleotide encoding the protein variant of the present disclosure, but the microorganism is not limited thereto.

As used herein, the term "transformation" refers to a process of introducing a vector including a polynucleotide encoding a target protein into a host cell, thereby enabling the expression of the protein encoded by the polynucleotide in the host cell. For the transformed polynucleotide, it does not matter whether it is inserted into the chromosome of the host cell and located therein or located outside the chromosome, as long as the transformed polynucleotide can be expressed in the host cell. Additionally, the polynucleotide includes DNA and RNA which encode the target protein. The polynucleotide may be inserted in any form as long as it can be introduced into a host cell and expressed therein. For example, the polynucleotide may be introduced into a host cell in the form of an expression cassette, which is a gene construct including all of the essential elements required for self-expression. The expression cassette may conventionally include a promoter operably linked to the polynucleotide, a transcription termination signal, a ribosome-binding domain, and a translation termination signal. The expression cassette may be in the form of a self-replicable expression vector. Additionally, the polynucleotide may be introduced into a host cell as is and operably linked to a sequence essential for its expression in the host cell, but is not limited thereto.

Additionally, as used herein, the term "operably linked" refers to a functional linkage between a promoter sequence, which initiates and mediates the transcription of the polynucleotide encoding the target protein, i.e., a conjugate of the present disclosure, and the above gene sequence.

As used herein, the term "IMP-producing microorganism" refers to a microorganism which is naturally capable of producing IMP; or a microorganism whose parent strain is not naturally capable of producing and/or exporting IMP which is provided with an ability to produce or export IMP. In the present disclosure, the microorganism producing IMP can be used interchangeably with a microorganism exporting IMP or a microorganism having an activity of exporting IMP.

The IMP-producing microorganism is a host cell or microorganism, which includes a protein variant having an activity of exporting IMP or a polynucleotide encoding the protein variant, or which is transformed with a vector containing the polynucleotide encoding the protein variant, and is thereby capable of expressing the protein variant. Specifically, the microorganism of the present disclosure may be a microorganism of the genus *Escherichia*, a microorganism of the genus *Serratia*, a microorganism of the genus *Erwinia*, a microorganism of the genus *Enterobacteria*, a microorganism of the genus *Salmonella*, a microorganism of the genus *Streptomyces*, a microorganism of the genus *Pseudomonas*, a microorganism of the genus *Brevibacterium*, a microorganism of the genus *Corynebacterium*, etc., and more specifically, the microorganism of the present disclosure may be a microorganism of the genus *Corynebacterium*.

As used herein, the term "IMP-producing microorganism of the genus *Corynebacterium*" refers to a microorganism of the genus *Corynebacterium* which is naturally capable of producing IMP or capable of producing IMP by mutation. Specifically, as used herein, the microorganism of the genus *Corynebacterium* capable of producing IMP may be a native strain of the microorganism of the genus *Corynebacterium* capable of producing IMP; or a microorganism of the genus *Corynebacterium* with enhanced ability to producing IMP prepared by inserting a gene associated with IMP production or by enhancing or attenuating the endogenous gene associated with IMP production. More specifically, in the present disclosure, the microorganism of the genus *Corynebacterium* capable of producing IMP may be a microorganism of the genus *Corynebacterium* which has improved ability of producing IMP, by including a protein variant having an activity of exporting IMP or a polynucleotide encoding the protein variant, or by being transformed with a vector containing the polynucleotide encoding the protein variant. The "microorganism of the genus *Corynebacterium* with enhanced ability to producing IMP" may be a microorganism of the genus *Corynebacterium* with improved ability to producing IMP compared to that of its parent strain before transformation or that of an unmodified microorganism of the genus *Corynebacterium*. The "unmodified microorganism of the genus *Corynebacterium*" may be a native type of the microorganism of the genus *Corynebacterium*, or a microorganism of the genus *Corynebacterium* which does not contain the protein variant capable of exporting IMP, or a microorganism of the genus *Corynebacterium* which is not transformed with a vector containing a polynucleotide encoding the protein variant capable of exporting IMP.

In an embodiment of the present disclosure, the microorganism of the present disclosure may be a microorganism in which an activity of adenylosuccinate synthetase and/or IMP dehydrogenase is further attenuated.

Specifically, the microorganism of the present disclosure may be *Corynebacterium glutamicum*, *Corynebacterium ammoniagenes*, *Brevibacterium lactofermentum*, *Brevibacterium flavum*, *Corynebacterium thermoaminogenes*, *Corynebacterium efficiens*, or *Corynebacterium stationis*, but the microorganism is not limited thereto.

Still another aspect of the present disclosure provides a method for preparing IMP, which includes culturing the microorganism of the genus *Corynebacterium* producing IMP of the present disclosure in a medium.

Specifically, the method of the present disclosure may further include a step of recovering IMP from the microorganism of the present disclosure or the medium of the present disclosure.

In the above method of the present disclosure, the cultivation of the microorganism may be performed in a batch process, continuous process, fed-batch process, etc. known in the art, but the cultivation process is not particularly limited thereto. In particular, with respect to the cultivation conditions, the pH of the culture may be adjusted to a suitable pH (e.g., pH 5 to 9, specifically pH 6 to 8, and most specifically with an appropriate basic compound (e.g., sodium hydroxide, potassium hydroxide, or ammonia) or acidic compound (e.g., phosphoric acid or sulfuric acid), and the aerobic condition of the culture may be maintained by introducing oxygen or an oxygen-containing gas mixture to the culture. The cultivation temperature may generally be in the range of 20° C. to 45° C., and specifically 25° C. to 40° C. for about 10 to 160 hours, but the cultivation conditions are not limited thereto. The IMP produced by the above cultivation may be secreted into the culture or may be retained in the cells.

Additionally, examples of the carbon sources to be used in the culture medium may include sugars and carbohydrates (e.g., glucose, sucrose, lactose, fructose, maltose, molasses, starch, and cellulose); oils and fats (e.g., soybean oil, sunflower oil, peanut oil, and coconut oil); fatty acids (e.g., palmitic acid, stearic acid, and linoleic acid); alcohols (e.g., glycerol and ethanol); and organic acids (e.g., acetic acid), but are not limited thereto. These carbon sources may be used alone or in combination, but are not limited thereto. Examples of the nitrogen sources to be used in the culture medium may include nitrogen-containing organic compounds (e.g., peptone, yeast extract, meat gravy, malt extract, corn steep liquor, soybean flour, and urea) or inorganic compounds (e.g., ammonium sulfate, ammonium chloride, ammonium phosphate, ammonium carbonate, and ammonium nitrate), etc. These nitrogen sources may be used alone or in combination, but are not limited thereto. Examples of the phosphorus sources to be used in the culture medium may include potassium dihydrogen phosphate, dipotassium hydrogen phosphate, corresponding sodium-containing salts, etc., but are not limited thereto. Additionally, metal salts (e.g., magnesium sulfate or iron sulfate), amino acids, vitamins, etc., which are essential growth-promoting materials, may be contained in the medium.

In the present disclosure, the method for recovering the IMP produced in the step of cultivation may be performed by collecting the IMP from the culture broth using an appropriate method known in the art. For example, methods such as centrifugation, filtration, anion exchange chromatography, crystallization, HPLC, etc. may be used, and the desired IMP can be recovered from a culture or cultured microorganism using an appropriate method known in the art.

Further, the recovery step may include a purification process and may be performed using an appropriate method known in the art. Thus, the IMP to be recovered may be in a purified form or a microorganism fermentation broth containing IMP.

Still another aspect of the present disclosure provides a composition for producing IMP, which contains a protein variant capable of exporting IMP of the present disclosure or a polynucleotide encoding the protein variant.

The composition of the present disclosure may further contain any constitution that is capable of operating the polynucleotide without limitation. In the composition of the present disclosure, the polynucleotide may be in a form in which the polynucleotide is included in a vector such that an operably linked gene can be expressed in a host cell where the polynucleotide is introduced.

Additionally, the composition may further contain any appropriate excipient conventionally used in compositions for producing IMP (e.g., preservatives, humectants, dispersing agents, suspending agents, buffering agents, stabilizing agents, isotonic agents, etc.), but the appropriate excipient is not limited thereto.

Still another aspect of the present disclosure provides use of the protein variant of the present disclosure for increasing IMP production in a microorganism of the genus *Corynebacterium*.

Still another aspect of the present disclosure provides a method for increasing export of IMP, which includes enhancing an activity of the protein consisting of SEQ ID NO: 2 in a microorganism of the genus *Corynebacterium*. Specifically, the enhancement of the activity of the protein consisting of SEQ ID NO: 2 may be performed by introducing, applying, or including a protein variant capable of exporting IMP, in which the protein variant consists of an amino acid sequence which has, from the N-terminus in the amino acid sequence of SEQ ID NO: 2, a substitution of the $123^{rd}$ amino acid with another amino acid, a substitution of the $243^{rd}$ amino acid with another amino acid, a substitution of the $387^{th}$ amino acid with another amino acid, a substitution of the $405^{th}$ amino acid with another amino acid; a substitution of the $413^{th}$ amino acid with another amino acid, a substitution of the $458^{th}$ amino acid with another amino acid, or a combination thereof. The terms, "protein capable of exporting IMP", "protein variant capable of exporting IMP", and "microorganism of the genus *Corynebacterium*" are as described above.

Still another aspect of the present disclosure provides use of the protein variant of the present disclosure for increasing export of IMP in a microorganism of the genus *Corynebacterium*.

Advantageous Effects of the Invention

IMP can be produced in high yield by culturing a microorganism of the genus *Corynebacterium* producing IMP using a protein variant, which is capable of exporting IMP.

DETAILED DESCRIPTION OF THE INVENTION

The present disclosure will be described in detail as follows. Meanwhile, each of the explanations and exemplary embodiments disclosed herein can be applied to other respective explanations and exemplary embodiments. That is, all of the combinations of various factors disclosed herein belong to the scope of the present disclosure. Additionally, the scope of the present disclosure should not be limited by the specific disclosure provided hereinbelow.

Example 1: Discovery of IMP Export Proteins

A genomic DNA library of *Corynebacterium stationis* ATCC6872 was prepared for the identification of membrane proteins of *Corynebacterium* involved in the export of IMP. Then, since the wild-type strain of *Corynebacterium* cannot produce IMP, or even if it does produce IMP, it produces only a small amount thereof, a strain called CJI0323, which is capable of producing IMP, derived from the ATCC6872 strain was prepared for the identification of the ability to produce IMP. The CJI0323 strain prepared was subjected to screening of membrane proteins involved in IMP export using the genomic DNA library of the ATCC6872 strain. The specific details of the experiment are as follows.

Example 1-1: Selection of IMP-Producing Strain, CJI0323

The ATCC6872 cells were suspended in a phosphate buffer (pH 7.0) or citrate buffer (pH 5.5) at a concentration of $10^7$ cells/mL to $10^8$ cells/mL to prepare an ATCC6872-derived IMP-producing strain, and the cells were subjected to UV treatment and placed at room temperature or 32° C. for 20 to 40 minutes to induce mutation. The resulting cells were washed twice with a 0.85% saline solution, and then diluted and plated on a medium, which was prepared by adding a resistance-providing material at an appropriate concentration to a minimal medium containing 1.7% agar, and colonies were obtained thereafter. Each colony was cultured in a nutrient medium and cultured in a seed medium for 24 hours. After culturing the colonies for 3 to 4 days in a fermentation medium, the colony with the highest amount of IMP produced accumulated in the culture medium was selected. In the course of preparing a strain capable of producing IMP at high concentration, in order to provide adenine auxotrophy, guanine leakage, lysozyme susceptibility, 3,4-dehydroproline resistance, streptomycin resistance, azetidine carboxylic acid resistance, thiaproline resistance, azaserine resistance, sulfaguanidine resistance, norvaline resistance, and trimethoprim resistance, the procedures above were performed sequentially for each material. As a result, CJI0323, which showed resistance to the above materials and excellent ability to produce IMP, was finally selected. The degree of resistance between ATCC6872 and CJI0323 was compared and the results are shown in Table 1 below.

TABLE 1

| Characteristics | ATCC6872 | CJI0323 |
| --- | --- | --- |
| Adenine auxotrophy | Non-auxotrophy | Auxotrophy |
| Guanine leakage | Non-auxotrophy | Leaky auxotrophy |
| Lysozyme susceptibility | 80 μg/mL | 8 μg/mL |
| 3,4-Dihydroproline resistance | 1000 μg/mL | 3500 μg/mL |
| Streptomycin resistance | 500 μg/mL | 2000 μg/mL |
| Azetidine carboxylic acid resistance | 5 mg/mL | 30 mg/mL |
| Thiaproline resistance | 10 μg/mL | 100 μg/mL |
| Azaserine resistance | 25 μg/mL | 100 μg/mL |
| Sulfaguanidine resistance | 50 μg/mL | 200 μg/mL |
| Norvaline resistance | 0.2 mg/mL | 2 mg/mL |
| Trimethoprim resistance | 20 μg/mL | 100 μg/mL |

Minimal medium: 2% glucose, 0.3% sodium sulfate, 0.1% $KH_2SO_4$, 0.3% $K_2HPO_4$, 0.3% magnesium sulfate, calcium chloride (10 mg/L), iron sulfate (10 mg/L), zinc sulfate (1 mg/L), manganese chloride (3.6 mg/L), L-cysteine (20 mg/L), calcium pantothenate (10 mg/L), thiamine hydrochloride (5 mg/L), biotin (30 μg/L), adenine (20 mg/L), guanine (20 mg/L), pH 7.3

Nutrient medium: 1% peptone, 1% meat juice, 0.25% sodium chloride, 1% yeast extract, 2% agar, pH 7.2

Seed medium: 1% glucose, 1% peptone, 1% meat juice, 1% yeast extract, 0.25% sodium chloride, adenine (100 mg/L), guanine (100 mg/L), pH 7.5

Fermentation medium: 0.1% sodium glutamate, 1% ammonium chloride, 1.2% magnesium sulfate, 0.01% calcium chloride, iron sulfate (20 mg/L), manganese sulfate (20 mg/L), zinc sulfate (20 mg/L), copper sulfate (5 mg/L), L-cysteine (23 mg/L), alanine (24 mg/L), nicotinic acid (8 mg/L), biotin (45 μg/L), thiamine hydrochloride (5 mg/L), adenine (30 mg/L), 1.9% phosphoric acid (85%), 2.55% glucose, 1.45% fructose Example 1-2: Experiments on Fermentation Titer of CJI0323

The seed medium (2 mL) was dispensed into test tubes (diameter: 18 mm), which were then autoclaved and each inoculated with ATCC6872 and CJI0323. Thereafter, the resultants were shake-cultured at 30° C. for 24 hours and then used as a seed culture solution. The fermentation medium (29 mL) was dispensed into Erlenmeyer flasks (250 mL) for shaking, autoclaved at 121° C. for 15 minutes, and the seed culture solution (2 mL) was inoculated thereto and cultured for 3 days. The culture conditions were set to 170 rpm, 30° C., and a pH of 7.5.

Upon completion of the culture, the amount of IMP produced was measured by HPLC (SHIMAZDU LC20A) and the results of the culture are shown in Table 2 below.

TABLE 2

| Strain | IMP (g/L) |
| --- | --- |
| ATCC6872 | 0 |
| CJI0323 | 9.52 |

The CJI0323 strain was named *Corynebacterium stationis* CN01-0323, deposited on Nov. 7, 2017, to the Korean Culture Center of Microorganisms (KCCM), an international depositary authority under the Budapest Treaty, and assigned Accession Number KCCM12151P.

Example 1-3: Discovery of Exporting Proteins

Screening conditions showing growth inhibition of the CJI0323 strain were established by additionally adding IMP to the minimal medium containing 1.7% agar. The plasmids of the genomic library of the ATCC6872 strain were transformed into the CJI0323 strain by electroporation (van der Rest et al. 1999), and those colonies in which the growth inhibition was released under the medium conditions supplemented with an excess amount of IMP were selected. Plasmids were obtained from the selected colonies and analyzed by a sequencing technique. As a result, one kind of membrane protein involved in the release of the growth inhibition was identified under the condition where an excess amount of IMP was added.

The one kind of membrane protein from *Corynebacterium* was identified based on the amino acid sequence of SEQ ID NO: 2 and the nucleotide sequence of SEQ ID NO: 4 (NCBI GenBank: NZ_CP014279, WP 066795121, MFS transporter). The membrane protein is known as the MFS transporter, but its specific function has not been confirmed, and further, its function regarding the IMP export is still unknown. In the present disclosure, the membrane protein was named ImpE2(WT).

Example 2: Identification of ImpE1 and ImpE2

Example 2-1: Confirmation of ImpE1 and ImpE2

In order to examine the functions of the membrane protein, ImpE2, the gene structure of SEQ ID NO: 4 was confirmed in the NCBI (NCBI GenBank: NZ_CP014279, WP_066795121, MFS transporter). As a result, it was confirmed that the 7 bp starting portion of the ORF of SEQ ID NO: 4 (impE2) overlaps in 7 nucleotide bases with a different gene (NCBI GenBank: NZ_CP014279, WP_066795119, transcriptional regulator), which is located upstream of impE2. Since the functions of the gene located upstream of impE2 and the protein encoded by the gene have not been confirmed, in the present disclosure, the protein was named ImpE1(WT) (the amino acid sequence of SEQ ID NO: 1 and the nucleotide sequence of SEQ ID NO: 3).

Example 2-2: Preparation of impE1- or impE2-Deficient Vector

In order to confirm whether the deletion of ImpE1 or ImpE2, which are involved in releasing the growth inhibition caused by IMP as identified in Examples 1 and 2-1, in an IMP-producing strain can reduce its IMP-exporting ability, attempts were made to prepare vectors deficient in each of the genes.

The gene fragments for preparing the vectors were obtained by PCR using the genomic DNA of the ATCC6872 strain as a template.

Specifically, the PCR for impE1 was performed using primers of SEQ ID NOS: 5 and 6 and primers of SEQ ID NOS: 7 and 8; and the PCR for impE2 was performed using the primers of SEQ ID NOS: 9 and 10 and primers of SEQ ID NOS: 11 and 12 (Table 3).

TABLE 3

| SEQ ID NO | Primer | Sequence (5'-3') |
|---|---|---|
| 5 | impE1 kop-1 | GCTCTAGACGAGAAAGCTAAAGCCGGTGA |
| 6 | impE1 kop-2 | GTTTTTAGCTACCATTGTTACACCCCGTGCAAGTTT |

TABLE 3-continued

| SEQ ID NO | Primer | Sequence (5'-3') |
|---|---|---|
| 7 | impE1 kop-3 | GCACGGGGTGTAACAATGGTAGCTAAAAACTCCACC |
| 8 | impE1 kop-4 | GCTCTAGAAATAGTTGGGGAAGTCCACTC |
| 9 | impE2 kop-1 | GCTCTAGACTTGGATGACCTGGTGGAAAA |
| 10 | impE2 kop-2 | CTTGGAGAAAATTTCCTACCATTCCAGTCCTTTCGT |
| 11 | impE2 kop-3 | GGACTGGAATGGTAGGAAATTTTCTCCAAGGGAAAT |
| 12 | impE2 kop-4 | GGACTAGTGGATTGTGTTGACGCACGATG |
| 65 | impE1E2 kop-2 | CTTGGAGAAAATTTCTGTTACACCCCGTGCAAGTTT |
| 66 | impE1E2 kop-3 | GCACGGGGTGTAACAGAAATTTTCTCCAAGGGAAAT |

In particular, the primers used were prepared based on information on a gene of *Corynebacterium stationis* (ATCC6872) (NCBI Genbank: NZ_CP014279) registered in NIH GenBank and the nucleotide sequences adjacent thereto.

PCR was performed by initial denaturation at 94° C. for 5 minutes; 25 cycles consisting of denaturation at 94° C. for 30 seconds, annealing at 52° C. for 3 minutes, and polymerization at 72° C. for 1 minute; and final polymerization at 72° C. for 5 minutes.

Overlapping PCR was performed using two fragments of the impE1 gene, which were amplified using the primers of SEQ ID NOS: 5 and 6 and the primers of SEQ ID NOS: 7 and 8, as templates, and as a result, a polynucleotide template (1.8 kbp) was obtained. The obtained gene fragment was cloned into a linearized pDZ vector (Korean Patent No. 10-0924065 and International Patent Publication No. 2008-033001), which was digested with the restriction enzyme (XbaI), and ligated using T4 ligase, and thereby the pDZ-ΔimpE1 vector was prepared. Additionally, overlapping polymerase chain reaction was performed using a fragment of the impE2 gene, amplified using the primers of SEQ ID NOS: 9 and 10, and two fragments of the impE2 gene, amplified using the primers of SEQ ID NOS: 11 and 12, as templates, and as a result, a polynucleotide template (1.7 kbp) was obtained. The obtained gene fragment was digested with restriction enzymes, XbaI and SpeI. The gene fragment was cloned using T4 ligase into a linearized pDZ vector, which had already been digested with the restriction enzyme (XbaI), and thereby the pDZ-ΔimpE2 vector was prepared.

Example 2-3: Preparation of impE1- and impE2-Integration-Deficient Vectors

Since the impE1 and impE2 genes, which encode proteins involved in releasing the growth inhibition caused by IMP, are overlapped, there is a need to regulate both genes simultaneously. Therefore, attempts were made to prepare a vector in which both impE1 and impE2 are deficient.

For the PCR of impE1 and impE2 genes, primers of SEQ ID NOS: 5 and 65 and primers of SEQ ID NOS: 66 and 12 were used. The primers used were prepared based on information on a gene of *Corynebacterium stationis* (ATCC6872) (NCBI Genbank: NZ_CP014279) registered in NIH GenBank and the nucleotide sequences adjacent thereto. Overlapping PCR was performed using a fragment of the impE1 gene, amplified using the primers of SEQ ID NOS: 5 and 65, and two fragments of the impE2 gene, amplified using the primers of SEQ ID NOS: 66 and 12, as templates, and as a result, a polynucleotide template (2.0 kbp) was obtained. The obtained gene fragments were digested with XbaI and SpeI, respectively. The gene fragments were cloned using T4 ligase into a linearized pDZ vector, which had already been digested with the restriction enzyme (XbaI), and thereby the pDZ-ΔimpE1E2 vector was prepared.

Example 2-4: Preparation of impE1- and impE2-Deficient Strains

The two kinds of plasmids prepared in Example 2-2 and one kind of plasmid prepared in Example 2-3 were each transformed into the CJI0323 strain by electroporation (using the transformation method disclosed in *Appl. Microbiol. Biotechnol.* (1999) 52: 541 to 545). The strains in which the vector was inserted into the chromosome by recombination of the homologous sequences were selected on a medium containing kanamycin (25 mg/L). The selected primary strains were subjected to a second cross-over. The genetic deficiency in the finally transformed strains was confirmed by performing PCR using the primer pairs of SEQ ID NOS: 5 and 8, SEQ ID NOS: 9 and 12, and SEQ ID NOS: 5 and 12.

The selected strains were named CJI0323_ΔimpE1, CJI0323_ΔimpE2, and CJI0323_ΔimpE1E2. Additionally, the ability to produce IMP of these strains was evaluated.

The seed medium (2 mL) was dispensed into test tubes (diameter: 18 mm), which were then autoclaved, each inoculated with CJI0323, CJI0323_ΔimpE1, CJI0323_ΔimpE2, and CJI0323_ΔimpE1E2, shake-cultured at 30° C. for 24 hours, and used as seed culture solutions. The fermentation medium (29 mL) was dispensed into Erlenmeyer flasks (250 mL) for shaking and autoclaved at 121° C. for 15 minutes. Then, the seed culture solution (2 mL) was inoculated thereto and the resultant was cultured for 3 days. The culture conditions were set to 170 rpm, 30° C., and a pH of 7.5.

Upon completion of the culture, the amount of IMP produced was measured by HPLC, and the results of the culture are shown in Table 4 below.

TABLE 4

| Strain | IMP (g/L) |
| --- | --- |
| CJI0323 | 9.52 |
| CJI0323_ΔimpE1 | 1.92 |
| CJI0323_ΔimpE2 | 1.88 |
| CJI0323_ΔimpE1E2 | 1.80 |

The IMP amount accumulated in each strain was compared with that of the parent strain, *Corynebacterium stationis* CJI0323. As a result, it was found that, as shown in Table 4 above, the IMP concentrations of the strains CJI0323_ΔimpE1, CJI0323_ΔimpE2, and CJI0323_ΔimpE1E2 were reduced by about 8 g/L under the same conditions compared to the CJI0323 strain, confirming that ImpE1 and ImpE2 are proteins involved in the IMP export.

Example 3: Confirmation of Nucleotide Sequences of impE1 and impE2 of IMP-Producing Strain, CJI0323

In the case of the CJI0323 strain producing IMP at high concentration in Example 1, it is possible that the strain has an improved IMP-exporting ability so as to produce IMP at high concentration. Accordingly, an attempt was made to confirm the presence of any mutation in impE1 and impE2 of the CJI0323 strain.

The chromosomal DNA of the CJI0323 strain was amplified by polymerase chain reaction (hereinafter, "PCR"). Specifically, first, PCR was performed by repeating 28 cycles consisting of denaturation at 94° C. for 1 minute, annealing at 58° C. for 30 seconds, and polymerization at 72° C. for 2 minutes using the chromosomal DNA of the CJI0323 strain as a template along with the primers of SEQ ID NOS: 13 and 14 (Table 5), and thereby a fragment of about 2.8 kbp was amplified.

TABLE 5

| SEQ ID NO | Primer | Sequence (5' to 3') |
| --- | --- | --- |
| 13 | impE1E2 seqF | GAACGGAGTCATCTCCTTTGC |
| 14 | impE1E2 seqR | CCAAACGCTCTGCAAGAAACTG |

Upon analysis of the nucleotide sequence using the same primers, it was confirmed that the $490^{th}$ nucleotide of the impE1 gene (i.e., g) was substituted with 'a', compared to the nucleotide sequence of the wild-type strain, ATCC6872. This substitution indicates that there was a mutation in which the $164^{th}$ amino acid of the ImpE1 protein (i.e., glutamic acid) was substituted with lysine.

Additionally, it was confirmed that the $4^{th}$ nucleotide of the impE2 gene (i.e., g) was substituted with 'a' (this means that the $666^{th}$ nucleotide of the impE1 gene (i.e., g) was substituted with 'a') and the $191^{st}$ nucleotide of the impE1 gene (i.e., g) was substituted with 'a'. These substitutions indicate that there were mutations in which the $2^{nd}$ amino acid of the ImpE2 protein (i.e., valine), which corresponds to the $222^{nd}$ amino acid of the ImpE1 protein, was substituted with isoleucine; and the $64^{th}$ amino acid of the ImpE2 protein (i.e., glycine) was substituted with glutamic acid.

The impE1 nucleotide of the CJI0323 strain was named impE1_CJI0323 (SEQ ID NO: 87) and the protein thereof was named ImpE1_CJI0323 (SEQ ID NO: 85), whereas the impE2 nucleotide of the CJI0323 strain was named impE2_CJI0323 (SEQ ID NO: 88) and the protein thereof was named ImpE2_CJI0323 (SEQ ID NO: 86).

Example 4: Recovery of Mutations in impE1 and impE2

Example 4-1: Preparation of Vectors for Recovering Mutations in impE1 or impE2

In Example 3, the presence of any mutation in impE1 and impE2 of the IMP-producing strain CJI0323 was examined. As a result, it was confirmed that impE1 had one mutation and impE2 had two mutations. Since the CJI0323 strain produces IMP at a high concentration, it is highly likely that the mutation is one that can improve the ability to export IMP. Accordingly, after recovering the mutated impE1 and impE2 to the native wild-type ImpE without mutation, the following experiment was performed to confirm whether additionally discovered protein variants have improved IMP-exporting ability.

To prepare a recovery vector, PCR was performed using *Corynebacterium stationis* ATCC6872 as a template.

The impE1 impE2 gene fragment amplified using the primers of SEQ ID NOS: 89 and 90 was treated with a restriction enzyme, XbaI, and cloned into the XbaI restriction site on the pDZ vector, and thereby the pDZ-impE1E2 (WT) was prepared.

Example 4-2: Preparation of Vectors with Single Mutation in impE1 or impE2

The plasmid prepared in Example 4-1 was transformed into the CJI0323 strain by electroporation (using the transformation method disclosed in *Appl. Microbiol. Biotechnol.* (1999) 52: 541 to 545). The strains in which the vector was inserted into the chromosome by recombination of the homologous sequences were selected on a medium containing kanamycin (25 mg/L). The selected primary strains were subjected to a second cross-over. The recovery of the mutation in the finally transformed strains was confirmed by performing PCR using the primer pair of SEQ ID NOS: 89 and 90, followed by nucleotide sequencing analysis. The prepared strain was named CJI0323_impE1E2(WT).

Example 5: Discovery of Mutations in impE2

Among the three kinds of mutations discovered through the results in Example 3, the one having the highest IMP-exporting ability was selected and the following experiment was performed to discover mutations having a higher IMP-exporting ability compared to the same.

Example 5-1: Selection of Mutations Having the Highest IMP-Exporting Ability Among impE1E2 Mutations A vector with a single E164K mutation in the ImpE1 gene was prepared using the native wild-type strain, *Corynebacterium stationis* ATCC6872, as a template along with the primers of SEQ ID NOS: 91 and 92 and primers of SEQ ID NOS: 93 and 94. Overlapping PCR was performed using an E164K-1 gene fragment amplified using the primers of SEQ ID NOS: 91 and 92 and two E164K-2 gene fragments amplified using the primers of SEQ ID NOS: 93 and 94, and thereby a template with a 1.8 kbp polynucleotide was obtained. The obtained gene fragments were digested with XbaI and cloned into a linearized pDZ vector, which had already been digested with XbaI, using T4 ligase, and thereby the pDZ-impE1 (E164K) vector was prepared.

A vector with a single V2I mutation in the ImpE2 gene was prepared using the ATCC6872 strain as a template along with the primers of SEQ ID NOS: 91 and 95 and primers of SEQ ID NOS: 96 and 94. Overlapping PCR was performed using a V2I-1 gene fragment amplified using the primers of SEQ ID NOS: 91 and 95 and two V2I-2 gene fragments amplified using the primers of SEQ ID NOS: 96 and 94, and thereby a template with a 1.8 kbp polynucleotide was obtained. The obtained gene fragments were digested with XbaI and cloned into a linearized pDZ vector, which had already been digested with XbaI, using T4 ligase, and thereby the pDZ-impE2(V2I) vector was prepared.

A vector with a single G64E mutation in the ImpE2 gene was prepared using the ATCC6872 strain as a template along with the primers of SEQ ID NOS: 91 and 97 and primers of SEQ ID NOS: 98 and 94. Overlapping PCR was performed using a G64E-1 gene fragment amplified using the primers of SEQ ID NOS: 91 and 97 and two G64E-2 gene fragments amplified using the primers of SEQ ID NOS: 98 and 94, and thereby a template with a 1.8 kbp polynucleotide was obtained. The obtained gene fragments were digested with XbaI and cloned into a linearized pDZ vector, which had already been digested with XbaI, using T4 ligase, and thereby the pDZ-impE2(G64E) vector was prepared.

TABLE 6

| SEQ ID NO | Primer | Sequence (5' to 3') |
|---|---|---|
| 89 | impE1E2 WT F | GCTCTAGAGAACGGAGTCATCTCCTTTGC |
| 90 | impE1E2 WT R | GCTCTAGACCAAACGCTCTGCAAGAAACTG |
| 91 | impE1 164K-1 | GCTCTAGACTTGGATGACCTGGTGGAAAA |
| 92 | impE1 164K-2 | CTGGGGCGCGTTGTTTTTCAGGATGCTCCC GAAGACG |
| 93 | impE1 164K-3 | AACAACGCGCCCCAGAATTGG |
| 94 | impE1 164K-4 | GCTCTAGAAATAGTTGGGGAAGTCCACTC |
| 95 | impE2 V2I-2 | TGGAGTTTTTAGCTATCATTCCAGTCCTTT CGTGTAA |
| 96 | impE2 V2I-3 | TAGCTAAAAACTCCACCCCAA |
| 97 | impE2 G64E-2 | CCGAAAATCATCTGCTCCAAAGAGCTCATC AGCATGG |
| 98 | impE2 G64E-3 | GCAGATGATTTTCGGTTCCGC |

The three kinds of plasmids prepared in Example 4-2 were transformed into the CJI0323_impE1E2(WT) strain (using the transformation method disclosed in *Appl. Microbiol. Biotechnol.* (1999) 52: 541 to 545). The strains in which the vector was inserted into the chromosome by recombination of the homologous sequences were selected on a medium containing kanamycin (25 mg/L). The selected primary strains were subjected to a second cross-over. The introduction of the mutation in the finally transformed strains was confirmed by performing PCR using the primer pair of SEQ ID NOS: 13 and 14, followed by nucleotide sequencing analysis. The selected strains were named CJI0323_impE1 (E164K), CJI0323_impE2(V2I), and CJI0323_impE2(G64E).

The CJI0323_impE1 (E164K), *Corynebacterium stationis* CJI0323_impE2(V2I), and *Corynebacterium stationis* CJI0323_impE2(G64E) strains were deposited on Nov. 2, 2018, to the Korean Culture Center of Microorganisms (KCCM), an international depositary authority under the Budapest Treaty, and assigned Accession Numbers KCCM12359P, KCCM12360P, and KCCM12361P, respectively.

The seed medium (2 mL) was dispensed into test tubes (diameter: 18 mm), which were then autoclaved, each inoculated with CJI0323_impE1E2(WT), CJI0323_impE1 (E164K), CJI0323_impE2(V2I), and CJI0323_impE2 (G64E), shake-cultured at 30° C. for 24 hours, and used as seed culture solutions. The fermentation medium (29 mL) was dispensed into Erlenmeyer flasks (250 mL) for shaking and autoclaved at 121° C. for 15 minutes. Then, the seed culture solutions (2 mL) were inoculated thereto and the resultants were cultured for 3 days. The culture conditions were set to 170 rpm, 30° C., and a pH of 7.5.

Upon completion of the culture, the amount of IMP produced was measured by HPLC, and the results of the culture are shown in Table 7 below.

TABLE 7

| Strain | IMP (g/L) |
| --- | --- |
| CJI0323 | 9.52 |
| CJI0323_impE1E2(WT) | 2.32 |
| CJI0323_impE1(E164K) | 2.57 |
| CJI0323_impE2(V2I) | 3.11 |
| CJI0323_impE2(G64E2) | 3.27 |

As shown above, it was confirmed that each of the three kinds of mutations is involved in IMP export, and that the CJI0323_impE2(G64E) strain had the greatest amount of IMP production among the three kinds of mutations.

Example 5-2: Preparation of Vectors for Substitutional Insertion of Amino Acids in impE2 Mutation To confirm the positional importance of the impE2(G64E) mutation among the representative three kinds of mutations with enhanced ability to produce IMP as identified in the results above, a vector for introducing a mutation of substituting the 64$^{th}$ amino acid in the amino acid sequence of impE2 with a different amino acid was prepared.

The procedure of preparing the vector for the introduction of the ImpE2(G64E) mutation is as follows.

Based on the reported polynucleotide sequences, the chromosomal genes of *Corynebacterium stationis* CJI0323 were isolated, and gene fragments were obtained by performing PCR using the chromosomal DNA of *Corynebacterium stationis* CJI0323 as a template along with primer pairs between the primer of SEQ ID NO: 15 and each of SEQ ID NOS: 16 to 33. PCR was performed by initial denaturation at 94° C. for 5 minutes; 20 cycles consisting of denaturation at 94° C. for 30 seconds, annealing at 55° C. for 30 seconds, and polymerization at 72° C. for 1 minute; and final polymerization at 72° C. for 5 minutes. As a result, 18 kinds of 1 kbp polynucleotides were obtained.

Then, the chromosomal genes of *Corynebacterium stationis* CJI0323 were isolated, and gene fragments were obtained by performing PCR using the chromosomal DNA of *Corynebacterium stationis* CJI0323 as a template along with primer pairs between the primer of SEQ ID NO: 34 and each of SEQ ID NOS: 35 to 52. PCR was performed by initial denaturation at 94° C. for 5 minutes; 20 cycles consisting of denaturation at 94° C. for 30 seconds, annealing at 55° C. for 30 seconds, and polymerization at 72° C. for 1 minute; and final polymerization at 72° C. for 5 minutes. As a result, 18 kinds of 1 kbp polynucleotides were obtained.

Overlapping PCR was performed using two fragments obtained from the above results as a template, and thereby 18 kinds of 2 kbp polynucleotides to be used as templates were obtained. The obtained gene fragments were digested with a restriction enzyme, XbaI, ligated to the linearized pDZ vector, which had already been digested with a restriction enzyme, XbaI, transformed into *E. coli* DH5α, and the transformants were plated on a solid LB medium containing kanamycin (25 mg/L).

The sequence information on the primers used for the preparation of the vector is shown in Table 8 below.

TABLE 8

| SEQ ID NO | Primer | Sequence (5' to 3') |
| --- | --- | --- |
| 15 | XbaI-impE2 64 1F | GGGTCTAGAAAAGAGCTTAAGGCAGCTGCT |
| 16 | impE2 64-R 1R | GAAAATCATCTGGCGCAAAGAGCTCAT |
| 17 | impE2 64-H 1R | GAAAATCATCTGGTGCAAAGAGCTCAT |
| 18 | impE2 64-D 1R | GAAAATCATCTGGTCCAAAGAGCTCAT |
| 19 | impE2 64-K 1R | GAAAATCATCTGCTTCAAAGAGCTCAT |
| 20 | impE2 64-S 1R | GAAAATCATCTGGGACAAAGAGCTCAT |
| 21 | impE2 64-T 1R | GAAAATCATCTGGGTCAAAGAGCTCAT |
| 22 | impE2 64-N 1R | GAAAATCATCTGGTTCAAAGAGCTCAT |
| 23 | impE2 64-Q 1R | GAAAATCATCTGCTGCAAAGAGCTCAT |
| 24 | impE2 64-C 1R | GAAAATCATCTGGCACAAAGAGCTCAT |
| 25 | impE2 64-P 1R | GAAAATCATCTGTGGCAAAGAGCTCAT |
| 26 | impE2 64-A 1R | GAAAATCATCTGAGCCAAAGAGCTCAT |
| 27 | impE2 64-V 1R | GAAAATCATCTGGACCAAAGAGCTCAT |
| 28 | impE2 64-I 1R | GAAAATCATCTGGATCAAAGAGCTCAT |
| 29 | impE2 64-L 1R | GAAAATCATCTGCAGCAAAGAGCTCAT |
| 30 | impE2 64-M 1R | GAAAATCATCTGCATCAAAGAGCTCAT |
| 31 | impE2 64-F 1R | GAAAATCATCTGGAACAAAGAGCTCAT |
| 32 | impE2 64-Y 1R | GAAAATCATCTGGTACAAAGAGCTCAT |
| 33 | impE2 64-W 1R | GAAAATCATCTGCCACAAAGAGCTCAT |
| 34 | XbaI-impE2 64 2R | GGGTCTAGACGGTCAATGAAGTCTCAACGG |
| 35 | impE2 64-R 2F | ATGAGCTCTTTGCGCCAGATGATTTTC |
| 36 | impE2 64-H 2F | ATGAGCTCTTTGCACCAGATGATTTTC |
| 37 | impE2 64-D 2F | ATGAGCTCTTTGGACCAGATGATTTTC |
| 38 | impE2 64-K 2F | ATGAGCTCTTTGAAGCAGATGATTTTC |
| 39 | impE2 64-S 2F | ATGAGCTCTTTGTCCCAGATGATTTTC |
| 40 | impE2 64-T 2F | ATGAGCTCTTTGACCCAGATGATTTTC |
| 41 | impE2 64-N 2F | ATGAGCTCTTTGAAGCAGATGATTTTC |
| 42 | impE2 64-Q 2F | ATGAGCTCTTTGCAGCAGATGATTTTC |
| 43 | impE2 64-C 2F | ATGAGCTCTTTGTGCCAGATGATTTTC |
| 44 | impE2 64-P 2F | ATGAGCTCTTTGCCACAGATGATTTTC |
| 45 | impE2 64-A 2F | ATGAGCTCTTTGGCTCAGATGATTTTC |
| 46 | impE2 64-V 2F | ATGAGCTCTTTGGTCCAGATGATTTTC |
| 47 | impE2 64-I 2F | ATGAGCTCTTTGATCCAGATGATTTTC |
| 48 | impE2 64-L 2F | ATGAGCTCTTTGCTGCAGATGATTTTC |
| 49 | impE2 64-M 2F | ATGAGCTCTTTGATGCAGATGATTTTC |
| 50 | impE2 64-F 2F | ATGAGCTCTTTGTTCCAGATGATTTTC |

TABLE 8-continued

| SEQ ID NO | Primer | Sequence (5' to 3') |
|---|---|---|
| 51 | impE2 64-Y 2F | ATGAGCTCTTTGTACCAGATGATTTTC |
| 52 | impE2 64-W 2F | ATGAGCTCTTTGTGGCAGATGATTTTC |

After selecting the colonies transformed with the vector into which the target gene was inserted, the plasmids were obtained using a conventionally known plasmid extraction method. The information on the obtained plasmids is shown in Table 9 below.

TABLE 9

| No. | Plasmid |
|---|---|
| 1 | pDZ-impE2 64R |
| 2 | pDZ-impE2 64H |
| 3 | pDZ-impE2 64D |
| 4 | pDZ-impE2 64K |
| 5 | pDZ-impE2 64S |
| 6 | pDZ-impE2 64T |
| 7 | pDZ-impE2 64N |
| 8 | pDZ-impE2 64Q |
| 9 | pDZ-impE2 64C |
| 10 | pDZ-impE2 64P |
| 11 | pDZ-impE2 64A |
| 12 | pDZ-impE2 64V |
| 13 | pDZ-impE2 64I |
| 14 | pDZ-impE2 64L |
| 15 | pDZ-impE2 64M |
| 16 | pDZ-impE2 64F |
| 17 | pDZ-impE2 64Y |
| 18 | pDZ-impE2 64W |

Example 5-3: Preparation of Strains where the Amino Acid at Position 64 of Variant (ImpE2) is Substituted with Another Amino Acid, and Comparison of Ability to Produce IMP The 18 kinds of plasmids prepared in Example 3-1 were transformed into the CJI0323 strain. The strains in which the vector was inserted into the chromosome by recombination of the homologous sequences were selected on a medium containing kanamycin (25 mg/L). The selected primary strains were subjected to a second cross-over. The introduction of the mutation in the finally transformed strains was confirmed by performing PCR using the primer pair of SEQ ID NOS: 13 and 14, followed by nucleotide sequencing analysis. The strain names according to the inserted mutations are shown in Table 10 below.

TABLE 10

| No. | Strain |
|---|---|
| 1 | CJI0323::impE2(G64R) |
| 2 | CJI0323::impE2(G64H) |
| 3 | CJI0323:impE2(G64D) |
| 4 | CJI0323::impE2(G64K) |
| 5 | CJI0323::impE2(G64S) |
| 6 | CJI0323::impE2(G64T) |
| 7 | CJI0323::impE2(G64N) |
| 8 | CJI0323::impE2(G64Q) |
| 9 | CJI0323::impE2(G64C) |
| 10 | CJI0323::impE2(G64P) |
| 11 | CJI0323::impE2(G64A) |
| 12 | CJI0323::impE2(G64V) |
| 13 | CJI0323::impE2(G64I) |

TABLE 10-continued

| No. | Strain |
|---|---|
| 14 | CJI0323:impE2(G64E) |
| 15 | CJI0323::impE2(G64M) |
| 16 | CJI0323::impE2(G64F) |
| 17 | CJI0323::impE2(G64Y) |
| 18 | CJI0323::impE2(G64W) |

Strains were cultured in the same manner as in Example 2 and the concentration of IMP therefrom was analyzed (Table 11).

TABLE 11

Concentration of IMP Production by impE2 Mutation (g/L)

| Strain | Average IMP |
|---|---|
| CJI0323_impE1E2(WT) | 2.32 |
| CJI0323_impE1(E164K)_impE2(V2I) | 4.24 |
| CJI0323::impE2(G64K) | 4.42 |
| CJI0323::impE2(G64H) | 5.14 |
| CJI0323::impE2(G64D) | 11.53 |
| CJI0323::impE2(G64K) | 8 |
| CJI0323::impE2(G64S) | 5.7 |
| CJI0323::impE2(G64T) | 5.52 |
| CJI0323::impE2(G64N) | 5.9 |
| CJI0323::impE2(G64Q) | 4.8 |
| CJI0323::impE2(G64C) | 5.9 |
| CJI0323::impE2(G64P) | 4.75 |
| CJI0323::impE2(G64A) | 4.58 |
| CJI0323::impE2(G64V) | 4.56 |
| CJI0323::impE2(G64I) | 5.89 |
| CJI0323::impE2(G64E) | 5.6 |
| CJI0323::impE2(G64M) | 4.3 |
| CJI0323::impE2(G64F) | 5.89 |
| CJI0323::impE2(G64Y) | 4.6 |
| CJI0323::impE2(G64W) | 4.76 |

As shown above, all of the modified strains showed an increase in the ability to produce IMP compared to the CJI0323_impE1E2(WT) strain, and thus, it was reconfirmed that the $64^{th}$ amino acid mutation of the impE2 is an important site that has a significant effect on the increase of the ability of the ImpE protein with respect to IMP export. In particular, in the case where the $64^{th}$ amino acid (i.e., glycine) is substituted with a different amino acid (i.e., aspartate), the ability to export IMP was increased by 172% compared to that of the CJI0323_impE1 (E164K) impE2 (V2I) strain, which has no mutation in the $64^{th}$ amino acid. Additionally, it was confirmed that in the case where the $64^{th}$ amino acid (i.e., glycine) is substituted with a different amino acid (i.e., aspartate), the ability to produce IMP was improved by 397% compared to the CJI0323_impE1E2 (WT) strain, which is the strain recovered to a wild-type strain, and by 20% compared to the CJI0323 strain.

Example 6: Library of impE Mutation Using Artificial Mutagenesis

To obtain a protein variant having an improved ability to export IMP, a vector library for a first cross-over insertion within the chromosome was prepared by the following method.

In this regard, an attempt was made to perform error-prone PCR with respect to impE2 of the CJI0323::impE2 (G64D) strain, which was confirmed to have the greatest ability to export IMP by the results of Example 5-3. To introduce a mutation in the amino acid sequence possessed by the CJI0323::G64D strain at a position downstream of the 64th amino acid thereof, impE gene variants (1.6 kbp) where nucleotide substitutions are randomly introduced from the 193rd nucleotide of the impE2 to about 130 bp downstream therefrom were obtained. Error-prone PCR was performed using the Diversify PCR Random Mutagenesis Kit (Clontech), and gene fragments were obtained by PCR using the genomic DNA of the CJI0323::impE2(G64D) strain as a template along with a primer pair of SEQ ID NO: 53 and SEQ ID NO: 54 (Table 12).

TABLE 12

| SEQ ID NO | Primer | Sequence (5' to 3') |
|---|---|---|
| 53 | impE lib F | CAGATGATTTTCGGTTCCGCTC |
| 54 | impE lib R | GACCGAGACAAAAACGCCAAACG |

Mutations were introduced to the amplified gene fragments in an amount of 0 to 3.5 mutations per 1 kb of each gene fragment. PCR was performed by initial denaturation at 94° C. for 5 minutes; 30 cycles consisting of denaturation at 94° C. for 30 seconds, annealing at 60° C. for 30 seconds, and polymerization at 72° C. for 1 minute and 36 seconds; and final polymerization at 72° C. for 5 minutes. As a result, a 1.6 kbp polynucleotide was obtained.

The amplified gene fragment was ligated to the pCR2.1-TOPO vector using the pCR2.1-TOPO TA cloning kit (Invitrogen), transformed into E. coli DH5α, and the transformants were plated on a solid LB medium containing kanamycin (25 mg/L). Twenty kinds of the transformed colonies were selected and plasmids were obtained therefrom. Upon analysis of the polynucleotide sequences of these plasmids, it was confirmed that mutations were introduced at different positions at a frequency of 3.5 mutations/kb. About 20,000 transformed E. coli colonies were selected and their plasmids were extracted. The resulting library was named pTOPO_impE library.

Example 7: Selection of Strains where impE Library Vectors are Inserted

The pTOPO_impE library vectors prepared in Example 6 were transformed by electroporation into the CJI0323::impE2(G64D) strain capable of producing IMP at high concentration and the transformants were plated on a nutrient medium containing kanamycin (25 mg/L). As a result, 10,000 colonies of strains, in which modified genes were inserted, were obtained and these colonies were named CJI0323::impE2(G64D)/pTOPO_impE(mt)1 to CJI0323::impE2(G64D)/pTOPO_impE(mt)10000.

Nutrient medium: 1% peptone, 1% meat juice, 0.25% sodium chloride, 1% yeast extract, 2% agar, pH 7.2

Seed medium: 1% glucose, 1% peptone, 1% meat juice, 1% yeast extract, 0.25% sodium chloride, adenine (100 mg/L), guanine (100 mg/L), pH 7.5

Fermentation medium: 0.1% sodium glutamate, 1% ammonium chloride, 1.2% magnesium sulfate, 0.01% calcium chloride, iron sulfate (20 mg/L), manganese sulfate (20 mg/L), zinc sulfate (20 mg/L), copper sulfate (5 mg/L), L-cysteine (23 mg/L), alanine (24 mg/L), nicotinic acid (8 mg/L), biotin (45 μg/L), thiamine hydrochloride (5 mg/L), adenine (30 mg/L), 1.9% phosphoric acid (85%), 2.55% glucose, 1.45% fructose Each of the obtained 10,000 colonies was inoculated with an autoclaved seed medium (200 μL), shake-cultured in a 96-deepwell plate of the Microplate shaker (TAITEC) at 1,200 rpm at 30° C. for 24 hours, and used as a seed culture solution. An autoclaved fermentation medium (290 μL) was dispensed into a 96-deepwell plate and the seed culture solution (200 μL) was inoculated thereto, and the resultant was shake-cultured for 72 hours under the same conditions as described above.

To analyze the amount of IMP produced in the culture solution, upon completion of culture, the supernatant of the culture solution (3 μL) was transferred into a 96-well UV-plate, in which distilled water (197 μL) had been dispensed into each well. Then, the resultant was shaken at 25° C. for 30 seconds using the Microplate shaker (TAITEC) and the absorbance at 270 nm was measured using the spectrophotometer. Upon comparison of the above absorbance with that of the CJI0323::impE2(G64D) strain, 50 colonies of the strains showing an increase in the absorbance by 10% or higher were selected. Other colonies showed a similar or decreased absorbance compared to that of the control.

The amount of IMP produced in the selected 50 strains was repeatedly confirmed by measuring their absorbance using the same method, and as a result, the top four strains with improved ability to produce IMP compared to that of the CJI0323::impE2(G64D) strain were selected.

Example 8: Confirmation of Ability to Produce IMP of Strains Selected from impE2 Mutation Library To compare the ability of producing IMP of the four strains selected in Example 7, these four strains were cultured by the following method and the components of the resulting culture solutions were analyzed.

A seed medium (5 mL), which is the same as in Example 2, was dispensed into autoclaved test tubes (diameter: 18 mm) and shake-cultured at 30° C. for 24 hours to be used as seed culture solutions. A fermentation medium (29 mL), which is the same as in Example 2, was dispensed into Erlenmeyer flasks (250 mL) for shaking and autoclaved at 121° C. for 15 minutes. Then, the seed culture solutions (2 mL) were inoculated thereto and the resultants were cultured for 4 to 5 days. The culture conditions were set to 170 rpm, 30° C., and a pH of 7.5. Upon completion of the culture, the amount of IMP produced was measured by HPLC.

Among these fifty strains, the top four strains with respect to the ability to produce IMP were selected and the cultivation and analysis were performed repeatedly. The concentrations of IMP analyzed are shown in Table 13 below.

TABLE 13

Concentration of IMP produced by selected strains
CJI0323::impE2(G64D)/pTOPO_impE(mt) (g/L)

| Strain | Average IMP |
|---|---|
| CJI0323::impE2(G64D) | 11.53 |
| CJI0323::impE2(G64D)/pTOPO_impE(mt)-627 | 13.47 |
| CJI0323::impE2(G64D)/pTOPO_impE(mt)-3605 | 12.96 |
| CJI0323::impE2(G64D)/pTOPO_impE(mt)-6765 | 13.17 |
| CJI0323::impE2(G64D)/pTOPO_impE(mt)-9997 | 12.70 |

As a result of the IMP concentration analysis, it was confirmed that the concentrations of the IMP of the four selected strains showed a maximum increase of 17% compared to that of the control strain, CJI0323::impE2(G64D).

Example 9: Confirmation of impE2 Gene Mutation in Selected Strains with impE2 Mutation To confirm the mutations introduced to the impE2 gene of the four strains selected in Example 8, the polynucleotide sequences of impE2 mutations were analyzed. To determine these polynucleotide sequences, PCR was performed using a primer pair of SEQ ID NO: 13 and SEQ ID NO: 14.

Analysis was performed for each of the polynucleotide sequences of the modified impE2 gene fragments obtained above. These polynucleotide sequences were compared to SEQ ID NO: 4 of impE2 (WT) or SEQ ID NO: 100 of impE2 (CJHB101::G64D), and as a result, the amino acid sequences of the modified impE2 were confirmed. The information on the mutations of the amino acid sequences of impE2 in the selected strains is shown in Table 14 below.

TABLE 14

Amino acid mutations of impE2 in selected four strains

| Strain | Amino acid mutations of impE2 |
|---|---|
| CJI0323::impE2(G64D)/pTOPO_impE(mt)-627 | impE2 (S387T, M413T, N458K) |
| CJI0323::impE2(G64D)/pTOPO_impE(mt)-3605 | impE2 (F123C) |
| CJI0323::impE2(G64D)/pTOPO_impE(mt)-6765 | impE2 (I243V) |
| CJI0323::impE2(G64D)/pTOPO_impE(mt)-9997 | impE2 (F405Y) |

Example 10: Preparation of Vectors for Insertion of Chromosome with impE2 Mutations To confirm the effects of application of impE2 mutations, which were identified in Example 9, vectors capable of introducing these impE2 mutations into the chromosome were prepared. The vector preparation process is as follows.

Only the vectors including the library mutations shown in Table 14, excluding the impE2(G64D) mutations, were prepared. Specifically, the chromosomal genes of *Corynebacterium stationis* ATCC6872 were isolated, and gene fragments were obtained by PCR using the primer pairs between SEQ ID NO: 56 and each of SEQ ID NOS: 57, 59, 61, and 63. PCR was performed by initial denaturation at 94° C. for 5 minutes; 20 cycles consisting of denaturation at 94° C. for 30 seconds, annealing at 55° C. for 30 seconds, and polymerization at 72° C. for 1 minute; and final polymerization at 72° C. for 5 minutes to obtain PCR fragments.

Gene fragments were obtained by PCR using each of the chromosomes of the four selected strains as a template along with primer pairs between SEQ ID NO: 55 and each of SEQ ID NOS: 58, 60, 62, and 64. PCR was performed by initial denaturation at 94° C. for 5 minutes; 20 cycles consisting of denaturation at 94° C. for 30 seconds, annealing at 55° C. for 30 seconds, and polymerization at 72° C. for 1 minute and 30 seconds; and final polymerization at 72° C. for 5 minutes to obtain PCR fragments. Overlapping PCR was performed using two fragments, and the obtained gene fragments were digested with a restriction enzyme (XbaI I). The resulting gene fragments were ligated using T4 ligase to a linearized pDZ vector (Korean Patent No. 10-0924065 and International Patent Publication No. 2008-033001), which had already been digested with a restriction enzyme (XbaI), transformed into *E. coli* DH5α, and the transformants were plated on a solid LB medium containing kanamycin (25 mg/L).

To prepare vectors with a single mutation for confirming the effects of the single mutations of the impE2 (S387T, M413T, and N458K), in which three kinds of mutations among the selected variants are integrated, PCR was performed using the ATCC6872 strain as a template along with primer pairs between SEQ ID NO: 56 and each of SEQ ID NOS: 67, 69, and 71, and thereby gene fragments were obtained. Then, PCR was performed using the ATCC6872 strain as a template along with primer pairs between SEQ ID NO: 55 and each of SEQ ID NOS: 68, 70, and 72, and thereby gene fragments were obtained. Overlapping PCR was performed using the two fragments prepared above, and the thus-obtained gene fragments were digested with a restriction enzyme (XbaI). The resulting gene fragments were ligated using T4 ligase to the linearized pDZ vector, which had already been digested with a restriction enzyme (XbaI), transformed into *E. coli* DH5α, and the transformants were plated on a solid LB medium containing kanamycin.

TABLE 15

| SEQ ID NO | Primer | Sequence (5' to 3') |
|---|---|---|
| 55 | impE mt-R | CATCTAGACCGAGACAAAAACGCCAAACG |
| 56 | impEW mt-1 | GCTCTAGACCGCGGATAACGTCGGCATTA |
| 57 | impEW ttk-2 | CATCCACCACAAAGCAAACGC |
| 58 | impEW ttk-3 | CTTTGTGGTGGATGACCCAGATGACCGTTGAGACTT |
| 59 | impEW C-2 | AAATGGAGATACCTGAGATGT |
| 60 | impEW C-3 | CAGGTATCTCCATTTGCGTTATTGGCTCGACGCTCG |
| 61 | impEW v-2 | GGCCGCAAAACCCATCCAGTC |
| 62 | impEW v-3 | ATGGGTTTTGCGGCCGTCGCAATCACGACCAGCACC |
| 63 | impEW y-2 | ATACAAGGAAGCGAACTCCGA |
| 64 | impEW Y-3 | TTCGCTTCCTTGTATACGGTGTCGGCTTGGGCTTTG |

After selecting the colonies transformed with the vector into which the target gene was inserted, the plasmids were obtained using a conventionally known plasmid extraction method. The plasmids were named pDZ-impE2(S387T, M413T, N458K), pDZ-impE2(F123C), pDZ-impE2 (I243V), pDZ-impE2(F405Y), pDZ-impE2(S387T), pDZ-impE2(M413T), and pDZ-impE2(N458K), according to the mutation inserted into impE2 of each plasmid.

Example 11: Preparation of Strains Introduced with impE2 Mutation Based on Wild-Type impE 1, impE2 and Comparison of their Abilities to Produce IMP The four kinds of vectors prepared in Example 10 for introducing novel mutations (i.e., pDZ-impE2(S387T, M413T, N458K), pDZ-impE2(F123C), pDZ-impE(I243V), and pDZ-impE2(F405Y)) were transformed by a two-step recombination of homologous chromosomes into the CJI0323_impE1E2(WT) strain, in which the impE1E2 of *Corynebacterium stationis* CJI0323 (an IMP-producing strain prepared in Example 4) was recovered to WT. Then, strains in which the impE2 mutations were introduced on the chromosome were selected by sequence analysis of the polynucleotides, and the strains were named CJI0323_impE1E2(WT) impE2(S387T, M413T, N458K), CJI0323_impE1E2(WT) impE2(F123C), CJI0323_impE1E2(WT) impE2(I243V), and CJI0323_impE1E2(WT) impE2(F405Y), respectively.

The *Corynebacterium stationis* CJI032_impE1E2(WT)_impE2(F123C), *Corynebacterium stationis* CJI0323_impE1E2(WT)_impE2(I243V), and *Corynebacterium stationis* CJI0323_impE1E2(WT)_impE2(F405Y) strains were deposited on Nov. 2, 2018, to the Korean Culture Center of Microorganisms (KCCM), an international depositary authority under the Budapest Treaty, and assigned Accession Numbers KCCM12362P, KCCM12363P, and KCCM12365P, respectively.

The strains were cultured in the same manner as in Example 7 and their IMP concentrations were analyzed. After 48 hours of culture, the concentrations were measured (Table 16).

TABLE 16

Concentration of IMP produced by strains introduced with impE2 mutations (g/L)

| Strain | Average IMP |
|---|---|
| CJI0323_impE1E2(WT) | 2.32 |
| CJI0323_impE1E2(WT)_impE2(S387T, M413T, N458K) | 3.35 |
| CJI0323_impE1E2(WT)_impE2(F123C) | 2.62 |
| CJI0323_impE1E2(WT)_impE2(I243V) | 2.74 |
| CJI0323_impE1E2(WT)_impE2(F405Y) | 2.90 |

With respect to IMP concentration, it was confirmed that the four novel modified strains showed a maximum increase of 44% compared to that of the CJI0323_impE1E2(WT) strain. The increase in the amount of IMP production due to mutations of the ImpE protein of the present disclosure can be interpreted to be very meaningful.

Example 12: Preparation of Strains Introduced with impE2 Mutation Based on CJI0323::impE2(G64D) and Comparison of Abilities to Produce IMP The four kinds of vectors prepared in Example 10 for introducing novel mutations (i.e., pDZ-impE2(S387T, M413T, N458K), pDZ-impE2(F123C), pDZ-impE(I243V), and pDZ-impE2(F405Y)) were transformed into the CJI0323_impE2(G64D) strain (i.e., an IMP-producing strain) by a two-step recombination of homologous chromosomes. Then, strains in which the impE2 mutations were introduced on the chromosome were selected by sequence analysis of the polynucleotides, and the strains were named CJI0323::impE2(G64D) impE2(S387T, M413T, N458K), CJI0323::impE2(G64D) impE2(F123C), CJI0323::impE2(G64D) impEp(I243V), and CJI0323::impE2(G64D) impE2p(F405Y), respectively, according to the inserted impE2 mutation.

The strains were cultured in the same manner as in Example 7 and their IMP concentrations were analyzed (Table 17).

TABLE 17

Concentration of IMP produced by strains introduced with impE2 mutations (g/L)

| Strain | Average IMP |
|---|---|
| CJI0323::impE2(G64D) | 11.53 |
| CJI0323::impE2(G64D)_impE2(S387T, M413T, N458K) | 13.47 |
| CJI0323::impE2(G64D)_impE2(F123C) | 12.90 |
| CJI0323::impE2(G64D)_impE2(I243V) | 13.17 |
| CJI0323::impE2(G64D)_impE2(F405Y) | 12.70 |

With respect to IMP concentration, it was confirmed that the four novel modified strains showed a maximum increase of 17% compared to that of the CJI0323::impE2(G64D) strain. The increase in the amount of IMP production due to mutations of the ImpE protein of the present disclosure can be interpreted to be very meaningful.

Then, the seven kinds of vectors prepared above (i.e., pDZ-impE2(S387T, M413T, N458K), pDZ-impE2(F123C), pDZ-impE(I243V), pDZ-impE2(F405Y), pDZ-impE2(S387T), pDZ-impE2(M413T), and pDZ-impE2(N458K)), alone or in combination, were transformed into the CJI0323_impE1E2(WT) strain or CJI0323::impE2(G64D) strain. The prepared strains were named CJI0323_impE1E2(WT)_impE2(S387T), CJI0323_impE1E2(WT)_impE2(M413T), CJI0323_impE1E2(WT)_impE2(N458K), CJI0323_impE1E2(WT)_impE2(F123C, I243V, S387T, F405Y, M413T, N458K)) CJI0323::impE2(G64D) impE2(S387T), CJI0323::impE2(G64D) impE2(M413T), CJI0323::impE2(G64D) impE2(N458K), CJI0323::impE2(G64D) impE2(I243V, S387T, M413T, N458K), CJI0323::impE2(G64D) impE2(S387T, F405Y, M413T, N458K), CJI0323::impE2(G64D) impE2(I243V, S387T, F405Y, M413T, N458K), CJI0323::impE2(G64D) impE2(F123C, S387T, M413T, N458K), and CJI0323::impE2(G64D) impE2(F123C, I243V, S387T, F405Y, M413T, N458K), and their abilities to produce IMP were measured in the same manner as described above (Table 18).

The *Corynebacterium stationis* CJI0323_impE1E2(WT)_impE2(S387T), *Corynebacterium stationis* CJI0323_impE1E2(WT)_impE2(M413T), and CJI0323_impE1E2(WT)_impE2(N458K) strains were deposited on Nov. 2, 2018, to the Korean Culture Center of Microorganisms (KCCM), an international depositary authority under the Budapest Treaty, and assigned Accession Numbers KCCM12364P, KCCM12366P, and KCCM12367P, respectively.

TABLE 18

Concentration of IMP produced by strains with a single impE2 mutation and strains introduced with combined impE2 mutations (g/L)

| Strain | Average IMP |
|---|---|
| CJI0323_impE1E2(WT) | 2.32 |
| CJI0323::impE2(G64D) | 11.52 |
| CJI0323_impE1E2(WT)_impE2(S387T) | 2.7 |
| CJI0323_impE1E2(WT)_impE2(M413T) | 3.1 |
| CJI0323_impE1E2(WT)_impE2(N458K) | 3.0 |
| CJI0323_impE1E2(WT)_impE2(F123C, I243V, S387T, F405Y, M413T, N458K) | 4.7 |
| CJI0323::impE2(G64D)_impE2(S387T) | 12.94 |
| CJI0323::impE2(G64D)_impE (M413T) | 13.0 |
| CJI0323::impE2(G64D)_impE2(N458K) | 13.1 |
| CJI0323::impE2(G64D)_impE2(I243V, S387T, M413T, N458K) | 13.6 |
| CJI0323::impE2(G64D)_impE2(S387T, F405Y, M413T, N458K) | 13.7 |
| CJI0323::impE2(G64D)_impE2(F123C, S387T, M413T, N458K) | 13.82 |
| CJI0323::impE2(G64D)_impE2(I243V, S387T, F405Y, M413T, N458K), | 14.0 |
| CJI0323::impE2(G64D)_impE2(F123C, I243V, S387T, F405Y, M413T, N458K) | 14.27 |

As shown in the above tables, it was confirmed that single mutations (i.e., impE2(S3877), impE2(M4137), and impE2(N458K)) showed a maximum increase of 33.6% compared to that of the wild-type strain, and all of the strains with a combination of novel mutations showed a maximum increase of 102.5%. Additionally, when a novel mutation alone was introduced into the CJI0323::impE2(G64D) strain, the ability to produce IMP was increased as shown in Tables 17 and 18, whereas when a combination of mutations was introduced into the strain, the strain was shown to have a more improved ability to produce IMP. In particular, when both a mutation of the CJI0323::impE2(G64D) strain and a novel mutation(s) are integrated into the strain, the ability to produce IMP was increased about 515% compared to that of the wild-type strain, while showing an about 24% increase compared to that of the CJI0323::impE2(G64D) strain. It was also confirmed that the novel mutations discovered in the present disclosure were shown to increase the ability to produce IMP even by a single mutation, and when these mutations were introduced in combination, the ability to produce IMP was increased even further.

Example 13: Enhancement of impE2 Based on IMP-Producing Strains

Example 13-1: Preparation of Strains Introduced with impE2 Mutation Based on IMP-Producing Strain To confirm the effects of introducing an impE2 mutation into strain, An IMP-producing strain was prepared in which the activities of adenylosuccinate synthetase and IMP dehydrogenase corresponding to the degradation pathway of IMP in the ATCC6872 strain were attenuated. The initiation codon was changed by changing the first base from 'a' to 't' in each nucleotide sequence of the two genes *purA* and *guaB*, which encode the two enzymes. The strain in which the expression of the two genes was attenuated in the ATCC6872 strain was named CJI9088. The pDZ-impE2 (S387T, M413T, N458K), pDZ-impE2(F123C), pDZ-impE (I243V), and pDZ-impE2(F405Y) vectors prepared in Example 10 were transformed into the CJI9088 strain, either alone or in combination, by electroporation. Then, the strains in which the vectors were inserted into the chromosome by recombination of the homologous sequences were selected on a medium containing kanamycin (25 mg/L). The selected primary strains were subjected to a second crossover, and the strains in which the modification of a target gene was introduced were selected. The introduction of the modification in the finally transformed strains was confirmed by performing PCR using the primer pair of SEQ ID NOS: 13 and 14, followed by nucleotide sequencing analysis.

The ability of the prepared strains (i.e., CJI9088, CJI9088_impE2(S387T, M413T, N458K), CJI9088_impE2 (F123C), CJI9088_impE2(I243V), CJI9088_impE2 (F405Y), and CJI9088_impE2(F123C, I243V, S387T, F405Y, M413T, N458K) to produce IMP was evaluated. Upon completion of the culture, the amount of IMP production was measured by HPLC and the results are shown in Table 19 below.

TABLE 19

| Strain | IMP (g/L) |
|---|---|
| CJI9088 | 0.52 |
| CJI9088_impE2(S387T, M413T, N458K) | 3.75 |
| CJI9088_impE2(F123C) | 0.94 |
| CJI9088_impE2(I243V) | 1.07 |
| CJI9088_impE2(F405Y) | 1.21 |
| CJI9088_impE2(F123C, I243V, S387T, F405Y, M413T, N458K) | 4.32 |

Upon confirming the amount of IMP accumulated in the culture medium, it was confirmed that these strains showed an increase of IMP production by at least 80%, and a maximum increase of 730%, compared to the parent strain, CJI9088. Accordingly, the increase in the amount of IMP production due to mutations of the ImpE protein of the present disclosure can be interpreted to be very meaningful.

From the foregoing, a skilled person in the art to which the present disclosure pertains will be able to understand that the present disclosure may be embodied in other specific forms without modifying the technical concepts or essential characteristics of the present disclosure. In this regard, the exemplary embodiments disclosed herein are only for illustrative purposes and should not be construed as limiting the scope of the present disclosure. On the contrary, the present disclosure is intended to cover not only the exemplary embodiments but also various alternatives, mutations, equivalents, and other embodiments that may be included within the spirit and scope of the present disclosure as defined by the appended claims.

SEQUENCE LISTING

```
Sequence total quantity: 156
SEQ ID NO: 1            moltype = AA  length = 222
FEATURE                 Location/Qualifiers
REGION                  1..222
                        note = ImpE1
source                  1..222
                        mol_type = protein
                        organism = unidentified
SEQUENCE: 1
LHAVQEVNDN EEDSLPGSDL GLREQKRLAT KHRIEDAATR LVDESSFDKV TIEEICEAAG 60
ISRRTFFNYF STKESAVIGA SSEPLTEKQR NDFLNADASN LLQLMVEQIK QHLESSHQSQ 120
AIHDRRQRIF ADPDVAVRAM AFRKERSRET MELIAQRLRE HPEEQRAPEL DPETEAMLLS 180
GFIREATWMA ISRPDRDCAL PVGDRIYRAM ELVKNYTKGL EW                 222

SEQ ID NO: 2            moltype = AA  length = 549
FEATURE                 Location/Qualifiers
REGION                  1..549
                        note = ImpE2
source                  1..549
                        mol_type = protein
                        organism = unidentified
SEQUENCE: 2
MVAKNSTPST AGHASAHTAE EFPVANAEMA TPSAIDPNHG KKTADNVGII FAALMLTMLM 60
SSLGQMIFGS ALPTIVGELG GVDQMSWVIS AFMVTMTIAM PLAGQLGDRM GRKWVYISGI 120
```

-continued

```
SIFVIGSTLG GFANGMGMLI TGRAIQGFGA GIMMISSQSI VAEVVSARER GKFMGIMGGV    180
FGVSSVLGPV LGGWFTDGPG WRWGLWINIP LGLLAIIVCA FVLKLRVGEQ GFKGFDWMGF    240
AAIAITTSTL ILLTTWGGSE YEWTSPTILS MAAVVIVGAL LTVFIESRAS QPLIPVQLFK    300
NRNMVLTTLA GTVLGLAMMG VLGYMPTYLQ MVHTLTPTEA GLMMIPMMVG MIGVSTGVGF    360
IIAKTGNYKY YPIAGLAITA FALWWMSQMT VETSLTGIGV RFLVFGVGLG FVMQVLVLIV    420
QNSFPVSQVG TATAANNFFR QIGSALGASI VGSMFIHNMQ NEMATRLPDA LASLGKEGAA    480
ISQQFQGADA ANSLTPHAVA ELPDVLRDAI LNSYNDGLTP VIGMMVPLAI VAMLILFPLR    540
QERLKETIE                                                           549

SEQ ID NO: 3           moltype = DNA  length = 669
FEATURE                Location/Qualifiers
source                 1..669
                       mol_type = other DNA
                       note = ImpE1
                       organism = unidentified
SEQUENCE: 3
ttgcatgctg tgcaagaagt taatgacaat gaagaagact ccctccctgg cagtgacctc    60
gggttaaggg agcagaagcg attggcaacc aagcatcgca tcgaagacgc cgcgacacgg   120
ttggttgatg aatcgagctt tgacaaagta acaattgaag aaatttgcga agccgccggg   180
atttcccgac gcacctttt taattatttc agcacgaaag aaagcgccgt tattggcgcg   240
tcctcggaac cgttgacgga aaagcaacgc aatgacttct tgaatgctga cgccagcaat   300
ctcctgcagc tgatggttga gcagatcaaa caacacttgg agtcttctca ccagagtcaa   360
gcgattcacg accgtcgtca gcgaatcttt gcggatccgg atgtcgcggt acgtgcaatg   420
gcgtttcgca aggaacgctc acgggaaacc atggagctaa tcgctcaacg tcttcggag    480
catcctgaag aacaacgcgc cccagaattg gatccgaaa cagaggcgat gctgctgagc   540
ggattcattc gcgaagccac ctggatggct atctcacgac ccgatcgtga ttgtgcactg   600
ccagtgggtg accgcatcta tcgcgcgatg gaattggtaa agaattacac gaaaggactg   660
gaatggtag                                                           669

SEQ ID NO: 4           moltype = DNA  length = 1650
FEATURE                Location/Qualifiers
misc_feature           1..1650
                       note = ImpE2
source                 1..1650
                       mol_type = other DNA
                       organism = unidentified
SEQUENCE: 4
atggtagcta aaaactccac cccaagcacg gccggccacg ccagtgctca cactgcggaa    60
gaattcccag tggccaatgc tgaaatggca acgccttcag caatcgaccc aaaccacggt   120
aaaaagaccg cggataacgt cggcattatc ttcgctgcct tgatgctcac catgctgatg   180
agctctttgg ggcagatgat tttcggttcc gctctgccaa ccatcgtcgg cgagctcggc   240
ggcgtggacc agatgagctg gtaatttca gcatttatgg tcaccatgac cattgctatg   300
ccactagccg gtcagctcgg tgaccgcatg ggccgcaagt ctcaggtatc   360
tccattttcg ttattggctc gacgctcggt ggctttgcca atggcatggg catgctgatc   420
accggacgtg caatccaggg cttcggtgcc ggcatcatga tgatttcctc gcagtcgatt   480
gtggctgagg ttgtctccgc acgtgagcgc ggcaagttca tgggtattat gggcggcgtc   540
tttggcgtct cctccgtact gggtccagtt ctcggtggcc ggttcaccga tggtcccagt   600
tggcgttggg gcctcgtggat caacattcca ctgggtctgc tggcaattat tgtctgcgct   660
ttcgtactga agctgcgcgt gggcgagcaa ggctttaagg gctttgactg gatgggtttt   720
gcggccatcg caatcacgac cagcaccctg attctgctca ccacttgggg cggaagcgaa   780
tacgagtgga cttccccaac tattttgtcc atggctgcca tagtcatcgt cggtcgcgtg   840
ctcaccgtgt tcattgagtc gcgtgcatcc cagccgctga tccggttca gctatttaag   900
aaccgcaaca tggttttgac caccctcgcc ggtactgttt gggtctgggc catgatgggc   960
gtgctcggct acatgccaac ctacctgcag atggtgcaca ccctgacgcc aactgaagca  1020
ggcttgatga tgatcccgat gatggtcggc atgatcggtg tctccactgg tgttggcttc  1080
atcatcgcta agaccggcaa ctacaagtac taccccatcg cgggcctggc catcacgacg  1140
tttgcttttgt ggtggatgtc ccagatgacc gttgagactt cattgaccgg tatcggagtt  1200
cgcttccttg tattcggtgt cggcttgggc tttgtcatgc aggtactggt gctgattgtt  1260
caaaactcct tccctgtatc gcaggtcggt actgccacgg cggctaataa cttcttccgc  1320
cagattggtt cggcattggg tgcttccatc gtggggttcga tgttcattca caatatgcag  1380
aatgagatgg ctaccgtttt gcctgatgcc cttgcatcgt tgggcaagga aggcgccgct  1440
atttcgcagc agttccaagg tgcagatgcc gccaactcct tgactccgca cgcagtcgca  1500
gagcttcccg atgtcctccg tgacgctatc ttaaattcct acaatgacgg tctgaccccc  1560
gtgattggca tgatggtgcc actggccatt gttgcaatgc tgattttgtt cccactgcgc  1620
caagagcgct tgaaggaaac catcgaataa                                  1650

SEQ ID NO: 5           moltype = DNA  length = 29
FEATURE                Location/Qualifiers
misc_feature           1..29
                       note = Primer impE1 kop-1
source                 1..29
                       mol_type = other DNA
                       organism = synthetic construct
SEQUENCE: 5
gctctagacg agaaagctaa agccggtga                                      29

SEQ ID NO: 6           moltype = DNA  length = 36
FEATURE                Location/Qualifiers
misc_feature           1..36
```

```
SEQ ID NO: 6          moltype = DNA  length = 36
FEATURE               Location/Qualifiers
misc_feature          1..36
                      note = Primer impE1 kop-2
source                1..36
                      mol_type = other DNA
                      organism = synthetic construct
SEQUENCE: 6
gtttttagct accattgtta caccccgtgc aagttt                                36

SEQ ID NO: 7          moltype = DNA  length = 36
FEATURE               Location/Qualifiers
misc_feature          1..36
                      note = Primer impE1 kop-3
source                1..36
                      mol_type = other DNA
                      organism = synthetic construct
SEQUENCE: 7
gcacggggtg taacaatggt agctaaaaac tccacc                                36

SEQ ID NO: 8          moltype = DNA  length = 29
FEATURE               Location/Qualifiers
misc_feature          1..29
                      note = Primer impE1 kop-4
source                1..29
                      mol_type = other DNA
                      organism = synthetic construct
SEQUENCE: 8
gctctagaaa tagttgggga agtccactc                                        29

SEQ ID NO: 9          moltype = DNA  length = 29
FEATURE               Location/Qualifiers
misc_feature          1..29
                      note = Primer impE2 kop-1
source                1..29
                      mol_type = other DNA
                      organism = synthetic construct
SEQUENCE: 9
gctctagact tggatgacct ggtggaaaa                                        29

SEQ ID NO: 10         moltype = DNA  length = 36
FEATURE               Location/Qualifiers
misc_feature          1..36
                      note = Primer impE2 kop-2
source                1..36
                      mol_type = other DNA
                      organism = synthetic construct
SEQUENCE: 10
cttggagaaa atttcctacc attccagtcc tttcgt                                36

SEQ ID NO: 11         moltype = DNA  length = 36
FEATURE               Location/Qualifiers
misc_feature          1..36
                      note = Primer impE2 kop-3
source                1..36
                      mol_type = other DNA
                      organism = synthetic construct
SEQUENCE: 11
ggactggaat ggtaggaaat tttctccaag ggaaat                                36

SEQ ID NO: 12         moltype = DNA  length = 29
FEATURE               Location/Qualifiers
misc_feature          1..29
                      note = Primer impE2 kop-4
source                1..29
                      mol_type = other DNA
                      organism = synthetic construct
SEQUENCE: 12
ggactagtgg attgtgttga cgcacgatg                                        29

SEQ ID NO: 13         moltype = DNA  length = 21
FEATURE               Location/Qualifiers
misc_feature          1..21
                      note = Primer impE1E2 seqF
source                1..21
                      mol_type = other DNA
                      organism = synthetic construct
SEQUENCE: 13
gaacggagtc atctcctttg c                                                21

SEQ ID NO: 14         moltype = DNA  length = 22
FEATURE               Location/Qualifiers
```

```
                                    -continued misc_feature            1..22
                        note = Primer impE1E2 seqR
source                  1..22
                        mol_type = other DNA
                        organism = synthetic construct
SEQUENCE: 14
ccaaacgctc tgcaagaaac tg                                              22

SEQ ID NO: 15           moltype = DNA   length = 30
FEATURE                 Location/Qualifiers
misc_feature            1..30
                        note = Primer XbaI-impE2 64 1F
source                  1..30
                        mol_type = other DNA
                        organism = synthetic construct
SEQUENCE: 15
gggtctagaa aagagcttaa ggcagctgct                                      30

SEQ ID NO: 16           moltype = DNA   length = 27
FEATURE                 Location/Qualifiers
misc_feature            1..27
                        note = Primer impE2 64-R 1R
source                  1..27
                        mol_type = other DNA
                        organism = synthetic construct
SEQUENCE: 16
gaaaatcatc tggcgcaaag agctcat                                         27

SEQ ID NO: 17           moltype = DNA   length = 27
FEATURE                 Location/Qualifiers
misc_feature            1..27
                        note = Primer impE2 64-H 1R
source                  1..27
                        mol_type = other DNA
                        organism = synthetic construct
SEQUENCE: 17
gaaaatcatc tggtgcaaag agctcat                                         27

SEQ ID NO: 18           moltype = DNA   length = 27
FEATURE                 Location/Qualifiers
misc_feature            1..27
                        note = Primer impE2 64-D 1R
source                  1..27
                        mol_type = other DNA
                        organism = synthetic construct
SEQUENCE: 18
gaaaatcatc tggtccaaag agctcat                                         27

SEQ ID NO: 19           moltype = DNA   length = 27
FEATURE                 Location/Qualifiers
misc_feature            1..27
                        note = Primer impE2 64-K 1R
source                  1..27
                        mol_type = other DNA
                        organism = synthetic construct
SEQUENCE: 19
gaaaatcatc tgcttcaaag agctcat                                         27

SEQ ID NO: 20           moltype = DNA   length = 27
FEATURE                 Location/Qualifiers
misc_feature            1..27
                        note = Primer impE2 64-S 1R
source                  1..27
                        mol_type = other DNA
                        organism = synthetic construct
SEQUENCE: 20
gaaaatcatc tgggacaaag agctcat                                         27

SEQ ID NO: 21           moltype = DNA   length = 27
FEATURE                 Location/Qualifiers
misc_feature            1..27
                        note = Primer impE2 64-T 1R
source                  1..27
                        mol_type = other DNA
                        organism = synthetic construct
SEQUENCE: 21
gaaaatcatc tgggtcaaag agctcat                                         27

SEQ ID NO: 22           moltype = DNA   length = 27
```

```
FEATURE                 Location/Qualifiers
misc_feature            1..27
                        note = Primer impE2 64-N 1R
source                  1..27
                        mol_type = other DNA
                        organism = synthetic construct
SEQUENCE: 22
gaaaatcatc tggttcaaag agctcat                                              27

SEQ ID NO: 23           moltype = DNA  length = 27
FEATURE                 Location/Qualifiers
misc_feature            1..27
                        note = Primer impE2 64-Q 1R
source                  1..27
                        mol_type = other DNA
                        organism = synthetic construct
SEQUENCE: 23
gaaaatcatc tgctgcaaag agctcat                                              27

SEQ ID NO: 24           moltype = DNA  length = 27
FEATURE                 Location/Qualifiers
misc_feature            1..27
                        note = Primer impE2 64-C 1R
source                  1..27
                        mol_type = other DNA
                        organism = synthetic construct
SEQUENCE: 24
gaaaatcatc tggcacaaag agctcat                                              27

SEQ ID NO: 25           moltype = DNA  length = 27
FEATURE                 Location/Qualifiers
misc_feature            1..27
                        note = Primer impE2 64-P 1R
source                  1..27
                        mol_type = other DNA
                        organism = synthetic construct
SEQUENCE: 25
gaaaatcatc tgtggcaaag agctcat                                              27

SEQ ID NO: 26           moltype = DNA  length = 27
FEATURE                 Location/Qualifiers
misc_feature            1..27
                        note = Primer impE2 64-A 1R
source                  1..27
                        mol_type = other DNA
                        organism = synthetic construct
SEQUENCE: 26
gaaaatcatc tgagccaaag agctcat                                              27

SEQ ID NO: 27           moltype = DNA  length = 27
FEATURE                 Location/Qualifiers
misc_feature            1..27
                        note = Primer impE2 64-V 1R
source                  1..27
                        mol_type = other DNA
                        organism = synthetic construct
SEQUENCE: 27
gaaaatcatc tggaccaaag agctcat                                              27

SEQ ID NO: 28           moltype = DNA  length = 27
FEATURE                 Location/Qualifiers
misc_feature            1..27
                        note = Primer impE2 64-I 1R
source                  1..27
                        mol_type = other DNA
                        organism = synthetic construct
SEQUENCE: 28
gaaaatcatc tggatcaaag agctcat                                              27

SEQ ID NO: 29           moltype = DNA  length = 27
FEATURE                 Location/Qualifiers
misc_feature            1..27
                        note = Primer impE2 64-L 1R
source                  1..27
                        mol_type = other DNA
                        organism = synthetic construct
SEQUENCE: 29
gaaaatcatc tgcagcaaag agctcat                                              27
```

| | | |
|---|---|---|
| SEQ ID NO: 30<br>FEATURE<br>misc_feature<br><br>source | moltype = DNA   length = 27<br>Location/Qualifiers<br>1..27<br>note = Primer impE2 64-M 1R<br>1..27<br>mol_type = other DNA<br>organism = synthetic construct | |
| SEQUENCE: 30<br>gaaaatcatc tgcatcaaag agctcat | | 27 |
| SEQ ID NO: 31<br>FEATURE<br>misc_feature<br><br>source | moltype = DNA   length = 27<br>Location/Qualifiers<br>1..27<br>note = Primer impE2 64-F 1R<br>1..27<br>mol_type = other DNA<br>organism = synthetic construct | |
| SEQUENCE: 31<br>gaaaatcatc tggaacaaag agctcat | | 27 |
| SEQ ID NO: 32<br>FEATURE<br>misc_feature<br><br>source | moltype = DNA   length = 27<br>Location/Qualifiers<br>1..27<br>note = Primer impE2 64-Y 1R<br>1..27<br>mol_type = other DNA<br>organism = synthetic construct | |
| SEQUENCE: 32<br>gaaaatcatc tggtacaaag agctcat | | 27 |
| SEQ ID NO: 33<br>FEATURE<br>misc_feature<br><br>source | moltype = DNA   length = 27<br>Location/Qualifiers<br>1..27<br>note = Primer impE2 64-W 1R<br>1..27<br>mol_type = other DNA<br>organism = synthetic construct | |
| SEQUENCE: 33<br>gaaaatcatc tgccacaaag agctcat | | 27 |
| SEQ ID NO: 34<br>FEATURE<br>misc_feature<br><br>source | moltype = DNA   length = 30<br>Location/Qualifiers<br>1..30<br>note = Primer XbaI-impE2 64 2R<br>1..30<br>mol_type = other DNA<br>organism = synthetic construct | |
| SEQUENCE: 34<br>gggtctagac ggtcaatgaa gtctcaacgg | | 30 |
| SEQ ID NO: 35<br>FEATURE<br>misc_feature<br><br>source | moltype = DNA   length = 27<br>Location/Qualifiers<br>1..27<br>note = Primer impE2 64-R 2F<br>1..27<br>mol_type = other DNA<br>organism = synthetic construct | |
| SEQUENCE: 35<br>atgagctctt tgcgccagat gattttc | | 27 |
| SEQ ID NO: 36<br>FEATURE<br>misc_feature<br><br>source | moltype = DNA   length = 27<br>Location/Qualifiers<br>1..27<br>note = Primer impE2 64-H 2F<br>1..27<br>mol_type = other DNA<br>organism = synthetic construct | |
| SEQUENCE: 36<br>atgagctctt tgcaccagat gattttc | | 27 |
| SEQ ID NO: 37<br>FEATURE<br>misc_feature<br><br>source | moltype = DNA   length = 27<br>Location/Qualifiers<br>1..27<br>note = Primer impE2 64-D 2F<br>1..27<br>mol_type = other DNA<br>organism = synthetic construct | |
| SEQUENCE: 37<br>atgagctctt tggaccagat gattttc | | 27 |

```
SEQ ID NO: 38           moltype = DNA   length = 27
FEATURE                 Location/Qualifiers
misc_feature            1..27
                        note = Primer impE2 64-K 2F
source                  1..27
                        mol_type = other DNA
                        organism = synthetic construct
SEQUENCE: 38
atgagctctt tgaagcagat gattttc                                           27

SEQ ID NO: 39           moltype = DNA   length = 27
FEATURE                 Location/Qualifiers
misc_feature            1..27
                        note = Primer impE2 64-S 2F
source                  1..27
                        mol_type = other DNA
                        organism = synthetic construct
SEQUENCE: 39
atgagctctt tgtcccagat gattttc                                           27

SEQ ID NO: 40           moltype = DNA   length = 27
FEATURE                 Location/Qualifiers
misc_feature            1..27
                        note = Primer impE2 64-T 2F
source                  1..27
                        mol_type = other DNA
                        organism = synthetic construct
SEQUENCE: 40
atgagctctt tgacccagat gattttc                                           27

SEQ ID NO: 41           moltype = DNA   length = 27
FEATURE                 Location/Qualifiers
misc_feature            1..27
                        note = Primer impE2 64-N 2F
source                  1..27
                        mol_type = other DNA
                        organism = synthetic construct
SEQUENCE: 41
atgagctctt tgaaccagat gattttc                                           27

SEQ ID NO: 42           moltype = DNA   length = 27
FEATURE                 Location/Qualifiers
misc_feature            1..27
                        note = Primer impE2 64-Q 2F
source                  1..27
                        mol_type = other DNA
                        organism = synthetic construct
SEQUENCE: 42
atgagctctt tgcagcagat gattttc                                           27

SEQ ID NO: 43           moltype = DNA   length = 27
FEATURE                 Location/Qualifiers
misc_feature            1..27
                        note = Primer impE2 64-C 2F
source                  1..27
                        mol_type = other DNA
                        organism = synthetic construct
SEQUENCE: 43
atgagctctt tgtgccagat gattttc                                           27

SEQ ID NO: 44           moltype = DNA   length = 27
FEATURE                 Location/Qualifiers
misc_feature            1..27
                        note = Primer impE2 64-P 2F
source                  1..27
                        mol_type = other DNA
                        organism = synthetic construct
SEQUENCE: 44
atgagctctt tgccacagat gattttc                                           27

SEQ ID NO: 45           moltype = DNA   length = 27
FEATURE                 Location/Qualifiers
misc_feature            1..27
                        note = Primer impE2 64-A 2F
source                  1..27
                        mol_type = other DNA
                        organism = synthetic construct
SEQUENCE: 45
```

```
atgagctctt tggctcagat gattttc                                          27

SEQ ID NO: 46           moltype = DNA   length = 27
FEATURE                 Location/Qualifiers
misc_feature            1..27
                        note = Primer impE2 64-V 2F
source                  1..27
                        mol_type = other DNA
                        organism = synthetic construct
SEQUENCE: 46
atgagctctt tggtccagat gattttc                                          27

SEQ ID NO: 47           moltype = DNA   length = 27
FEATURE                 Location/Qualifiers
misc_feature            1..27
                        note = Primer impE2 64-I 2F
source                  1..27
                        mol_type = other DNA
                        organism = synthetic construct
SEQUENCE: 47
atgagctctt tgatccagat gattttc                                          27

SEQ ID NO: 48           moltype = DNA   length = 27
FEATURE                 Location/Qualifiers
misc_feature            1..27
                        note = Primer impE2 64-L 2F
source                  1..27
                        mol_type = other DNA
                        organism = synthetic construct
SEQUENCE: 48
atgagctctt tgctgcagat gattttc                                          27

SEQ ID NO: 49           moltype = DNA   length = 27
FEATURE                 Location/Qualifiers
misc_feature            1..27
                        note = Primer impE2 64-M 2F
source                  1..27
                        mol_type = other DNA
                        organism = synthetic construct
SEQUENCE: 49
atgagctctt tgatgcagat gattttc                                          27

SEQ ID NO: 50           moltype = DNA   length = 27
FEATURE                 Location/Qualifiers
misc_feature            1..27
                        note = Primer impE2 64-F 2F
source                  1..27
                        mol_type = other DNA
                        organism = synthetic construct
SEQUENCE: 50
atgagctctt tgttccagat gattttc                                          27

SEQ ID NO: 51           moltype = DNA   length = 27
FEATURE                 Location/Qualifiers
misc_feature            1..27
                        note = Primer impE2 64-Y 2F
source                  1..27
                        mol_type = other DNA
                        organism = synthetic construct
SEQUENCE: 51
atgagctctt tgtaccagat gattttc                                          27

SEQ ID NO: 52           moltype = DNA   length = 27
FEATURE                 Location/Qualifiers
misc_feature            1..27
                        note = Primer impE2 64-W 2F
source                  1..27
                        mol_type = other DNA
                        organism = synthetic construct
SEQUENCE: 52
atgagctctt tgtggcagat gattttc                                          27

SEQ ID NO: 53           moltype = DNA   length = 22
FEATURE                 Location/Qualifiers
misc_feature            1..22
                        note = Primer impE lib F
source                  1..22
                        mol_type = other DNA
                        organism = synthetic construct
```

```
SEQUENCE: 53
cagatgattt tcggttccgc tc                                              22

SEQ ID NO: 54          moltype = DNA   length = 23
FEATURE                Location/Qualifiers
misc_feature           1..23
                       note = Primer impE lib R
source                 1..23
                       mol_type = other DNA
                       organism = synthetic construct
SEQUENCE: 54
gaccgagaca aaaacgccaa acg                                             23

SEQ ID NO: 55          moltype = DNA   length = 29
FEATURE                Location/Qualifiers
misc_feature           1..29
                       note = Primer impE mt - R
source                 1..29
                       mol_type = other DNA
                       organism = synthetic construct
SEQUENCE: 55
catctagacc gagacaaaaa cgccaaacg                                       29

SEQ ID NO: 56          moltype = DNA   length = 29
FEATURE                Location/Qualifiers
misc_feature           1..29
                       note = Primer impEW mt - 1
source                 1..29
                       mol_type = other DNA
                       organism = synthetic construct
SEQUENCE: 56
gctctagacc gcggataacg tcggcatta                                       29

SEQ ID NO: 57          moltype = DNA   length = 21
FEATURE                Location/Qualifiers
misc_feature           1..21
                       note = Primer impEW ttk - 2
source                 1..21
                       mol_type = other DNA
                       organism = synthetic construct
SEQUENCE: 57
catccaccac aaagcaaacg c                                               21

SEQ ID NO: 58          moltype = DNA   length = 36
FEATURE                Location/Qualifiers
misc_feature           1..36
                       note = Primer impEW ttk - 3
source                 1..36
                       mol_type = other DNA
                       organism = synthetic construct
SEQUENCE: 58
ctttgtggtg gatgacccag atgaccgttg agactt                               36

SEQ ID NO: 59          moltype = DNA   length = 21
FEATURE                Location/Qualifiers
misc_feature           1..21
                       note = Primer impEW C - 2
source                 1..21
                       mol_type = other DNA
                       organism = synthetic construct
SEQUENCE: 59
aaatggagat acctgagatg t                                               21

SEQ ID NO: 60          moltype = DNA   length = 36
FEATURE                Location/Qualifiers
misc_feature           1..36
                       note = Primer impEW C - 3
source                 1..36
                       mol_type = other DNA
                       organism = synthetic construct
SEQUENCE: 60
caggtatctc catttgcgtt attggctcga cgctcg                               36

SEQ ID NO: 61          moltype = DNA   length = 21
FEATURE                Location/Qualifiers
misc_feature           1..21
                       note = Primer impEW v - 2
source                 1..21
                       mol_type = other DNA
```

```
                                organism = synthetic construct
SEQUENCE: 61
ggccgcaaaa cccatccagt c                                              21

SEQ ID NO: 62           moltype = DNA  length = 36
FEATURE                 Location/Qualifiers
misc_feature            1..36
                        note = Primer impEW v - 3
source                  1..36
                        mol_type = other DNA
                        organism = synthetic construct
SEQUENCE: 62
atgggttttg cggccgtcgc aatcacgacc agcacc                              36

SEQ ID NO: 63           moltype = DNA  length = 21
FEATURE                 Location/Qualifiers
misc_feature            1..21
                        note = Primer impEW y - 2
source                  1..21
                        mol_type = other DNA
                        organism = synthetic construct
SEQUENCE: 63
atacaaggaa gcgaactccg a                                              21

SEQ ID NO: 64           moltype = DNA  length = 36
FEATURE                 Location/Qualifiers
misc_feature            1..36
                        note = Primer impEW y - 3
source                  1..36
                        mol_type = other DNA
                        organism = synthetic construct
SEQUENCE: 64
ttcgcttcct tgtatacggt gtcggcttgg gctttg                              36

SEQ ID NO: 65           moltype = DNA  length = 36
FEATURE                 Location/Qualifiers
misc_feature            1..36
                        note = Primer impE1E2 kop-2
source                  1..36
                        mol_type = other DNA
                        organism = synthetic construct
SEQUENCE: 65
cttggagaaa atttctgtta caccccgtgc aagttt                              36

SEQ ID NO: 66           moltype = DNA  length = 36
FEATURE                 Location/Qualifiers
misc_feature            1..36
                        note = Primer impE1E2 kop-3
source                  1..36
                        mol_type = other DNA
                        organism = synthetic construct
SEQUENCE: 66
gcacggggtg taacagaaat tttctccaag ggaaat                              36

SEQ ID NO: 67           moltype = DNA  length = 21
FEATURE                 Location/Qualifiers
misc_feature            1..21
                        note = Primer impEW 387t - 2
source                  1..21
                        mol_type = other DNA
                        organism = synthetic construct
SEQUENCE: 67
catccaccac aaagcaaacg c                                              21

SEQ ID NO: 68           moltype = DNA  length = 36
FEATURE                 Location/Qualifiers
misc_feature            1..36
                        note = Primer impEW 387t - 3
source                  1..36
                        mol_type = other DNA
                        organism = synthetic construct
SEQUENCE: 68
ctttgtggtg gatgacccag atgaccgttg agactt                              36

SEQ ID NO: 69           moltype = DNA  length = 21
FEATURE                 Location/Qualifiers
misc_feature            1..21
                        note = Primer impEW 413t - 2
source                  1..21
```

```
                              mol_type = other DNA
                              organism = synthetic construct
SEQUENCE: 69
tgacaaagcc caagccgaca c                                                  21

SEQ ID NO: 70           moltype = DNA   length = 36
FEATURE                 Location/Qualifiers
misc_feature            1..36
                        note = Primer impEW 413t - 3
source                  1..36
                        mol_type = other DNA
                        organism = synthetic construct
SEQUENCE: 70
cttgggcttt gtcacgcagg tactggtgct gattgt                                  36

SEQ ID NO: 71           moltype = DNA   length = 21
FEATURE                 Location/Qualifiers
misc_feature            1..21
                        note = Primer impEW 458k- 2
source                  1..21
                        mol_type = other DNA
                        organism = synthetic construct
SEQUENCE: 71
ttgtgaatga acatcgaacc c                                                  21

SEQ ID NO: 72           moltype = DNA   length = 36
FEATURE                 Location/Qualifiers
misc_feature            1..36
                        note = Primer impEW 458k- 3
source                  1..36
                        mol_type = other DNA
                        organism = synthetic construct
SEQUENCE: 72
atgttcattc acaaaatgca gaatgagatg gctacc                                  36

SEQ ID NO: 73           moltype = AA   length = 549
FEATURE                 Location/Qualifiers
REGION                  1..549
                        note = impE2(F123C)
source                  1..549
                        mol_type = protein
                        organism = unidentified
SEQUENCE: 73
MVAKNSTPST AGHASAHTAE EFPVANAEMA TPSAIDPNHG KKTADNVGII FAALMLTMLM          60
SSLGQMIFGS ALPTIVGELG GVDQMSWVIS AFMVTMTIAM PLAGQLGDRM GRKWVYISGI         120
SICVIGSTLG GFANGMGMLI TGRAIQGFGA GIMMISSQSI VAEVVSARER GKFMGIMGGV         180
FGVSSVLGPV LGGWFTDGPG WRWGLWINIP LGLLAIIVCA FVLKLRVGEQ GFKGFDWMGF         240
AAIAITTSTL ILLTTWGGSE YEWTSPTILS MAAVVIVGAL LTVFIESRAS QPLIPVQLFK         300
NRNMVLTTLA GTVLGLAMMG VLGYMPTYLQ MVHTLTPTEA GLMMIPMMVG MIGVSTGVGF         360
IIAKTGNYKY YPIAGLAITA FALWWMSQMT VETSLTGIGV RFLVFGVGLG FVMQVLVLIV         420
QNSFPVSQVG TATAANNFFR QIGSALGASI VGSMFIHNMQ NEMATRLPDA LASLGKEGAA         480
ISQQFQGADA ANSLTPHAVA ELPDVLRDAI LNSYNDGLTP VIGMMVPLAI VAMLILFPLR         540
QERLKETIE                                                                549

SEQ ID NO: 74           moltype = AA   length = 549
FEATURE                 Location/Qualifiers
REGION                  1..549
                        note = impE2(I243V)
source                  1..549
                        mol_type = protein
                        organism = unidentified
SEQUENCE: 74
MVAKNSTPST AGHASAHTAE EFPVANAEMA TPSAIDPNHG KKTADNVGII FAALMLTMLM          60
SSLGQMIFGS ALPTIVGELG GVDQMSWVIS AFMVTMTIAM PLAGQLGDRM GRKWVYISGI         120
SIFVIGSTLG GFANGMGMLI TGRAIQGFGA GIMMISSQSI VAEVVSARER GKFMGIMGGV         180
FGVSSVLGPV LGGWFTDGPG WRWGLWINIP LGLLAIIVCA FVLKLRVGEQ GFKGFDWMGF         240
AAVAITTSTL ILLTTWGGSE YEWTSPTILS MAAVVIVGAL LTVFIESRAS QPLIPVQLFK         300
NRNMVLTTLA GTVLGLAMMG VLGYMPTYLQ MVHTLTPTEA GLMMIPMMVG MIGVSTGVGF         360
IIAKTGNYKY YPIAGLAITA FALWWMSQMT VETSLTGIGV RFLVFGVGLG FVMQVLVLIV         420
QNSFPVSQVG TATAANNFFR QIGSALGASI VGSMFIHNMQ NEMATRLPDA LASLGKEGAA         480
ISQQFQGADA ANSLTPHAVA ELPDVLRDAI LNSYNDGLTP VIGMMVPLAI VAMLILFPLR         540
QERLKETIE                                                                549

SEQ ID NO: 75           moltype = AA   length = 549
FEATURE                 Location/Qualifiers
REGION                  1..549
                        note = impE2(S387T)
source                  1..549
                        mol_type = protein
```

```
                                       organism = unidentified
SEQUENCE: 75
MVAKNSTPST AGHASAHTAE EFPVANAEMA TPSAIDPNHG KKTADNVGII FAALMLTMLM    60
SSLGQMIFGS ALPTIVGELG GVDQMSWVIS AFMVTMTIAM PLAGQLGDRM GRKWVYISGI   120
SIFVIGSTLG GFANGMGMLI TGRAIQGFGA GIMMISSQSI VAEVVSARER GKFMGIMGGV   180
FGVSSVLGPV LGGWFTDGPG WRWGLWINIP LGLLAIIVCA FVLKLRVGEQ GFKGFDWMGF   240
AAIAITTSTL ILLTTWGGSE YEWTSPTILS MAAVVIVGAL LTVFIESRAS QPLIPVQLFK   300
NRNMVLTTLA GTVLGLAMMG VLGYMPTYLQ MVHTLTPTEA GLMMIPMMVG MIGVSTGVGF   360
IIAKTGNYKY YPIAGLAITA FALWWMTQMT VETSLTGIGV RFLVFGVGLG FVMQVLVLIV   420
QNSFPVSQVG TATAANNFFR QIGSALGASI VGSMFIHNMQ NEMATRLPDA LASLGKEGAA   480
ISQQFQGADA ANSLTPHAVA ELPDVLRDAI LNSYNDGLTP VIGMMVPLAI VAMLILFPLR   540
QERLKETIE                                                         549

SEQ ID NO: 76            moltype = AA  length = 549
FEATURE                  Location/Qualifiers
REGION                   1..549
                         note = impE2(F405Y)
source                   1..549
                         mol_type = protein
                         organism = unidentified
SEQUENCE: 76
MVAKNSTPST AGHASAHTAE EFPVANAEMA TPSAIDPNHG KKTADNVGII FAALMLTMLM    60
SSLGQMIFGS ALPTIVGELG GVDQMSWVIS AFMVTMTIAM PLAGQLGDRM GRKWVYISGI   120
SIFVIGSTLG GFANGMGMLI TGRAIQGFGA GIMMISSQSI VAEVVSARER GKFMGIMGGV   180
FGVSSVLGPV LGGWFTDGPG WRWGLWINIP LGLLAIIVCA FVLKLRVGEQ GFKGFDWMGF   240
AAIAITTSTL ILLTTWGGSE YEWTSPTILS MAAVVIVGAL LTVFIESRAS QPLIPVQLFK   300
NRNMVLTTLA GTVLGLAMMG VLGYMPTYLQ MVHTLTPTEA GLMMIPMMVG MIGVSTGVGF   360
IIAKTGNYKY YPIAGLAITA FALWWMSQMT VETSLTGIGV RFLVYGVGLG FVMQVLVLIV   420
QNSFPVSQVG TATAANNFFR QIGSALGASI VGSMFIHNMQ NEMATRLPDA LASLGKEGAA   480
ISQQFQGADA ANSLTPHAVA ELPDVLRDAI LNSYNDGLTP VIGMMVPLAI VAMLILFPLR   540
QERLKETIE                                                         549

SEQ ID NO: 77            moltype = AA  length = 549
FEATURE                  Location/Qualifiers
REGION                   1..549
                         note = impE2(M413T)
source                   1..549
                         mol_type = protein
                         organism = unidentified
SEQUENCE: 77
MVAKNSTPST AGHASAHTAE EFPVANAEMA TPSAIDPNHG KKTADNVGII FAALMLTMLM    60
SSLGQMIFGS ALPTIVGELG GVDQMSWVIS AFMVTMTIAM PLAGQLGDRM GRKWVYISGI   120
SIFVIGSTLG GFANGMGMLI TGRAIQGFGA GIMMISSQSI VAEVVSARER GKFMGIMGGV   180
FGVSSVLGPV LGGWFTDGPG WRWGLWINIP LGLLAIIVCA FVLKLRVGEQ GFKGFDWMGF   240
AAIAITTSTL ILLTTWGGSE YEWTSPTILS MAAVVIVGAL LTVFIESRAS QPLIPVQLFK   300
NRNMVLTTLA GTVLGLAMMG VLGYMPTYLQ MVHTLTPTEA GLMMIPMMVG MIGVSTGVGF   360
IIAKTGNYKY YPIAGLAITA FALWWMSQMT VETSLTGIGV RFLVFGVGLG FVTQVLVLIV   420
QNSFPVSQVG TATAANNFFR QIGSALGASI VGSMFIHNMQ NEMATRLPDA LASLGKEGAA   480
ISQQFQGADA ANSLTPHAVA ELPDVLRDAI LNSYNDGLTP VIGMMVPLAI VAMLILFPLR   540
QERLKETIE                                                         549

SEQ ID NO: 78            moltype = AA  length = 549
FEATURE                  Location/Qualifiers
REGION                   1..549
                         note = impE2(N458K)
source                   1..549
                         mol_type = protein
                         organism = unidentified
SEQUENCE: 78
MVAKNSTPST AGHASAHTAE EFPVANAEMA TPSAIDPNHG KKTADNVGII FAALMLTMLM    60
SSLGQMIFGS ALPTIVGELG GVDQMSWVIS AFMVTMTIAM PLAGQLGDRM GRKWVYISGI   120
SIFVIGSTLG GFANGMGMLI TGRAIQGFGA GIMMISSQSI VAEVVSARER GKFMGIMGGV   180
FGVSSVLGPV LGGWFTDGPG WRWGLWINIP LGLLAIIVCA FVLKLRVGEQ GFKGFDWMGF   240
AAIAITTSTL ILLTTWGGSE YEWTSPTILS MAAVVIVGAL LTVFIESRAS QPLIPVQLFK   300
NRNMVLTTLA GTVLGLAMMG VLGYMPTYLQ MVHTLTPTEA GLMMIPMMVG MIGVSTGVGF   360
IIAKTGNYKY YPIAGLAITA FALWWMSQMT VETSLTGIGV RFLVFGVGLG FVMQVLVLIV   420
QNSFPVSQVG TATAANNFFR QIGSALGASI VGSMFIHKMQ NEMATRLPDA LASLGKEGAA   480
ISQQFQGADA ANSLTPHAVA ELPDVLRDAI LNSYNDGLTP VIGMMVPLAI VAMLILFPLR   540
QERLKETIE                                                         549

SEQ ID NO: 79            moltype = DNA  length = 1650
FEATURE                  Location/Qualifiers
misc_feature             1..1650
                         note = impE2(F123C)
source                   1..1650
                         mol_type = other DNA
                         organism = unidentified
SEQUENCE: 79
atggtagcta aaaactccac cccaagcacg gccggccacg ccagtgctca cactgcggaa    60
```

```
gaattcccag tggccaatgc tgaaatggca acgccttcag caatcgaccc aaaccacggt    120
aaaaagaccg cggataacgt cggcattatc ttcgctgcct tgatgctcac catgctgatg    180
agctctttgg ggcagatgat tttcggttcc gctctgccaa ccatcgtcgg cgagctcggc    240
ggcgtggacc agatgagctg ggtaatttca gcatttatgg tcaccatgac cattgctatg    300
ccactagccg gtcagctcgg tgaccgcatg ggccgcaagt gggtctacat ctcaggtatc    360
tccatttgcg ttattggctc gacgctcggt ggctttgcca atggcatggg catgctgatc    420
accgacgtg caatccaggg cttcggtgcc ggcatcatga tgatttcctc gcagtcgatt    480
gtggctgagg ttgtctccgc acgtgagcgc ggcaagttca tgggtattat gggcggcgtc    540
tttggcgtct cctccgtact gggtccagtt ctcggtggct ggttcaccga tggtcccggt    600
tggcgttggg gcctgtggat caacattcca ctgggtctgc tggcaattat tgtctgcgct    660
ttcgtactga agctgcgcgt gggcgagcaa ggctttaagg ctttgactg atgggtttt    720
gcggccatcg caatcacgac cagcaccctg attctgctca ccacttgggg cggaagcgaa    780
tacgagtgga cttcccaac tattttgtcc atggctgccg tagtcatcgt cggcgcgctg    840
ctcaccgtgt tcattgagtc gcgtgcatcc cagccgctga tcccggttca gctatttaag    900
aaccgcaaca tggttttgac caccctcgcc ggtactgttt tgggtctggc catgatgggc    960
gtgctcggct acatgccaac ctacctgcag atggtgcaca ccctgacgcc aactgaagca   1020
ggcttgatga tgatcccgat gatggtcggc atgatcggtg tctccactgg tgttggcttc   1080
atcatcgcta agaccggcaa ctacaagtac taccccatcg cgggcctggc catcacgcg   1140
tttgctttgt ggtggatgtc ccagatgacc gttgagactt cattgaccgg tatcggagtt   1200
cgcttccttg tattcggtgt cggcttgggc tttgtcatgc aggtactggt gctgattgtt   1260
caaaactcct ccctgtatc gcaggtcggt actgccacgg cggctaataa cttcttccgc   1320
cagattggtt cggcattggg tgcttccatc gtgggttcga tgttcattca caatatgcag   1380
aatgagatgg ctaccgtttt gcctgatgcc cttgcatcgt tgggcaagga aggcgccgct   1440
atttcgcagc agttccaagg tgcagatgcc gccaactcct tgactccgca cgcagtcgca   1500
gagcttcccg catgtcctccg tgacgctatc ttaaattcct acaatgacgg tctgaccccc   1560
gtgattggca tgatggtgcc actggccatt gttgcaatgc tgattttgtt cccactcgcg   1620
caagagcgct tgaaggaaac catcgaataa                                    1650

SEQ ID NO: 80          moltype = DNA  length = 1650
FEATURE                Location/Qualifiers
misc_feature           1..1650
                       note = impE2(F123C)
source                 1..1650
                       mol_type = other DNA
                       organism = unidentified
SEQUENCE: 80
atggtagcta aaaactccac cccaagcacg gccggccacg ccagtgctca cactgcggaa     60
gaattcccag tggccaatgc tgaaatggca acgccttcag caatcgaccc aaaccacggt    120
aaaaagaccg cggataacgt cggcattatc ttcgctgcct tgatgctcac catgctgatg    180
agctctttgg ggcagatgat tttcggttcc gctctgccaa ccatcgtcgg cgagctcggc    240
ggcgtggacc agatgagctg ggtaatttca gcatttatgg tcaccatgac cattgctatg    300
ccactagccg gtcagctcgg tgaccgcatg ggccgcaagt gggtctacat ctcaggtatc    360
tccatttcg ttattggctc gacgctcggt ggctttgcca atggcatggg catgctgatc    420
accgacgtg caatccaggg cttcggtgcc ggcatcatga tgatttcctc gcagtcgatt    480
gtggctgagg ttgtctccgc acgtgagcgc ggcaagttca tgggtattat gggcggcgtc    540
tttggcgtct cctccgtact gggtccagtt ctcggtggct ggttcaccga tggtcccggt    600
tggcgttggg gcctgtggat caacattcca ctgggtctgc tggcaattat tgtctgcgct    660
ttcgtactga agctgcgcgt gggcgagcaa ggctttaagg ctttgactg atgggtttt    720
gcggccgtcg caatcacgac cagcaccctg attctgctca ccacttgggg cggaagcgaa    780
tacgagtgga cttcccaac tattttgtcc atggctgccg tagtcatcgt cggcgcgctg    840
ctcaccgtgt tcattgagtc gcgtgcatcc cagccgctga tcccggttca gctatttaag    900
aaccgcaaca tggttttgac caccctcgcc ggtactgttt tgggtctggc catgatgggc    960
gtgctcggct acatgccaac ctacctgcag atggtgcaca ccctgacgcc aactgaagca   1020
ggcttgatga tgatcccgat gatggtcggc atgatcggtg tctccactgg tgttggcttc   1080
atcatcgcta agaccggcaa ctacaagtac taccccatcg cgggcctggc catcacgcg   1140
tttgctttgt ggtggatgtc ccagatgacc gttgagactt cattgaccgg tatcggagtt   1200
cgcttccttg tattcggtgt cggcttgggc tttgtcatgc aggtactggt gctgattgtt   1260
caaaactcct ccctgtatc gcaggtcggt actgccacgg cggctaataa cttcttccgc   1320
cagattggtt cggcattggg tgcttccatc gtgggttcga tgttcattca caatatgcag   1380
aatgagatgg ctaccgtttt gcctgatgcc cttgcatcgt tgggcaagga aggcgccgct   1440
atttcgcagc agttccaagg tgcagatgcc gccaactcct tgactccgca cgcagtcgca   1500
gagcttcccg catgtcctccg tgacgctatc ttaaattcct acaatgacgg tctgaccccc   1560
gtgattggca tgatggtgcc actggccatt gttgcaatgc tgattttgtt cccactcgcg   1620
caagagcgct tgaaggaaac catcgaataa                                    1650

SEQ ID NO: 81          moltype = DNA  length = 1650
FEATURE                Location/Qualifiers
misc_feature           1..1650
                       note = impE2(S387T)
source                 1..1650
                       mol_type = other DNA
                       organism = unidentified
SEQUENCE: 81
atggtagcta aaaactccac cccaagcacg gccggccacg ccagtgctca cactgcggaa     60
gaattcccag tggccaatgc tgaaatggca acgccttcag caatcgaccc aaaccacggt    120
aaaaagaccg cggataacgt cggcattatc ttcgctgcct tgatgctcac catgctgatg    180
agctctttgg ggcagatgat tttcggttcc gctctgccaa ccatcgtcgg cgagctcggc    240
ggcgtggacc agatgagctg ggtaatttca gcatttatgg tcaccatgac cattgctatg    300
ccactagccg gtcagctcgg tgaccgcatg ggccgcaagt gggtctacat ctcaggtatc    360
```

-continued

```
tccattttcg ttattggctc gacgctcggt ggctttgcca atggcatggg catgctgatc    420
accggacgtg caatccaggg cttcggtgcc ggcatcatga tgatttcctc gcagtcgatt    480
gtggctgagg ttgtctccgc acgtgagcgc ggcaagttca tgggtattat gggcggcgtc    540
tttggcgtct cctccgtact gggtccagtt ctcggtggct ggttcaccga tggtcccggt    600
tggcgttggg gcctgtggat caacattcca ctgggtctgc tggcaattat tgtctgcgct    660
ttcgtactga agctgcgcgt gggcgagcaa ggctttaagg gctttgactg gatgggtttt    720
gcggccatcg caatcacgac cagcaccctg attctgctca ccacttgggg cggaagcgaa    780
tacgagtgga cttccccaac tattttgtcc atggctgccg tagtcatcgt cggcgcgctg    840
ctcaccgtgt tcattgagtc gcgtgcatcc cagccgctga tcccggttca gctatttaag    900
aaccgcaaca tggttttgac caccctcgcc ggtactgttt tgggtctggc catgatgggc    960
gtgctcggct acatgccaac ctacctgcag atggtgcaca ccctgacgcc aactgaagca   1020
ggcttgatga tgatcccgat gatggtcggc atgatcggtg tctccactgg tgttggcttc   1080
atcatcgcta agaccggcaa ctacaagtac taccccatcg cgggcctggc catcacgcg    1140
tttgctttgt ggtggatgac ccagatgacc gttgagactt cattgaccgg tatcggagtt   1200
cgcttccttg tattcggtgt cggcttgggc tttgtcatgc aggtactggt gctgattgtt   1260
caaaactcct tccctgtatc gcaggtcggt actgccacgg cggctaataa cttcttccgc   1320
cagattggtt cggcattggg tgcttccatc gtgggttcga tgttcattca caatatgcag   1380
aatgagatgg ctacccgttt gcctgatgcc cttgcatcgt tgggcaagga aggcgccgct   1440
atttcgcagc agttccaagg tgcagatgcc gccaactcct tgactccgca cgcagtcgca   1500
gagcttcccg atgtcctccg tgacgctatc ttaaattcct acaatgacgg tctgacccc    1560
gtgattggca tgatggtgcc actggccatt gttgcaatgc tgattttgtt cccactgcgc   1620
caagagcgct tgaaggaaac catcgaataa                                    1650
```

SEQ ID NO: 82        moltype = DNA   length = 1650
FEATURE              Location/Qualifiers
misc_feature         1..1650
                     note = impE2(F405Y)
source               1..1650
                     mol_type = other DNA
                     organism = unidentified
SEQUENCE: 82

```
atggtagcta aaaactccac cccaagcacg gccggccacg ccagtgctca cactgcggaa     60
gaattcccag tggccaatgc tgaaatggca acgccttcag caatcgaccc aaaccacggt    120
aaaaagaccg cggataacgt cggcattatc ttcgctgcct tgatgctcac catgctgatg    180
agctctttgg ggcagatgat tttcggttcc gctctgccaa ccatcgtcgg cgagctcggc    240
ggcgtggacc agatgagctg ggtaatttca gcatttatgg tcaccatgac cattgctatg    300
ccactagccg tcagctcggt gaccgcatg ggccgcaagt gggtctacat ctcaggtatc    360
tccattttcg ttattggctc gacgctcggt ggctttgcca atggcatggg catgctgatc    420
accggacgtg caatccaggg cttcggtgcc ggcatcatga tgatttcctc gcagtcgatt    480
gtggctgagg ttgtctccgc acgtgagcgc ggcaagttca tgggtattat gggcggcgtc    540
tttggcgtct cctccgtact gggtccagtt ctcggtggct ggttcaccga tggtcccggt    600
tggcgttggg gcctgtggat caacattcca ctgggtctgc tggcaattat tgtctgcgct    660
ttcgtactga agctgcgcgt gggcgagcaa ggctttaagg gctttgactg gatgggtttt    720
gcggccatcg caatcacgac cagcaccctg attctgctca ccacttgggg cggaagcgaa    780
tacgagtgga cttccccaac tattttgtcc atggctgccg tagtcatcgt cggcgcgctg    840
ctcaccgtgt tcattgagtc gcgtgcatcc cagccgctga tcccggttca gctatttaag    900
aaccgcaaca tggttttgac caccctcgcc ggtactgttt tgggtctggc catgatgggc    960
gtgctcggct acatgccaac ctacctgcag atggtgcaca ccctgacgcc aactgaagca   1020
ggcttgatga tgatcccgat gatggtcggc atgatcggtg tctccactgg tgttggcttc   1080
atcatcgcta agaccggcaa ctacaagtac taccccatcg cgggcctggc catcacgcg    1140
tttgctttgt ggtggatgtc ccagatgacc gttgagactt cattgaccgg tatcggagtt   1200
cgcttccttg tatacggtgt cggcttgggc tttgtcatgc aggtactggt gctgattgtt   1260
caaaactcct tccctgtatc gcaggtcggt actgccacgg cggctaataa cttcttccgc   1320
cagattggtt cggcattggg tgcttccatc gtgggttcga tgttcattca caatatgcag   1380
aatgagatgg ctacccgttt gcctgatgcc cttgcatcgt tgggcaagga aggcgccgct   1440
atttcgcagc agttccaagg tgcagatgcc gccaactcct tgactccgca cgcagtcgca   1500
gagcttcccg atgtcctccg tgacgctatc ttaaattcct acaatgacgg tctgacccc    1560
gtgattggca tgatggtgcc actggccatt gttgcaatgc tgattttgtt cccactgcgc   1620
caagagcgct tgaaggaaac catcgaataa                                    1650
```

SEQ ID NO: 83        moltype = DNA   length = 1650
FEATURE              Location/Qualifiers
misc_feature         1..1650
                     note = impE2(M413T)
source               1..1650
                     mol_type = other DNA
                     organism = unidentified
SEQUENCE: 83

```
atggtagcta aaaactccac cccaagcacg gccggccacg ccagtgctca cactgcggaa     60
gaattcccag tggccaatgc tgaaatggca acgccttcag caatcgaccc aaaccacggt    120
aaaaagaccg cggataacgt cggcattatc ttcgctgcct tgatgctcac catgctgatg    180
agctctttgg ggcagatgat tttcggttcc gctctgccaa ccatcgtcgg cgagctcggc    240
ggcgtggacc agatgagctg ggtaatttca gcatttatgg tcaccatgac cattgctatg    300
ccactagccg tcagctcggt gaccgcatg ggccgcaagt gggtctacat ctcaggtatc    360
tccattttcg ttattggctc gacgctcggt ggctttgcca atggcatggg catgctgatc    420
accggacgtg caatccaggg cttcggtgcc ggcatcatga tgatttcctc gcagtcgatt    480
gtggctgagg ttgtctccgc acgtgagcgc ggcaagttca tgggtattat gggcggcgtc    540
tttggcgtct cctccgtact gggtccagtt ctcggtggct ggttcaccga tggtcccggt    600
tggcgttggg gcctgtggat caacattcca ctgggtctgc tggcaattat tgtctgcgct    660
```

```
ttcgtactga agctgcgcgt gggcgagcaa ggctttaagg gctttgactg gatgggtttt    720
gcggccatcg caatcacgac cagcaccctg attctgctca ccacttgggg cggaagcgaa    780
tacgagtgga cttccccaac tattttgtcc atggctgccg tagtcatcgt cggcgcgctg    840
ctcaccgtgt tcattgagtc gcgtgcatcc cagccgctga tcccggttca gctatttaag    900
aaccgcaaca tggttttgac caccctcgcc ggtactgttt tgggtctggc catgatgggc    960
gtgctcggct acatgccaac ctacctgcag atggtgcaca ccctgacgcc aactgaagca   1020
ggcttgatga tgatcccgat gatggtcggc atgatcggtg tctccactgg tgttggcttc   1080
atcatcgcta agaccggcaa ctacaagtac taccccatcg cgggcctggc catcacggcc   1140
tttgctttgt ggtggatgtc ccagatgacc gttgagactt cattgaccgg tatcggagtt   1200
cgcttccttg tattcggtgt cggcttgggc tttgtcacgc aggtactggt gctgattgtt   1260
caaaactcct tccctgtatc gcaggtcggg actgccacgg cggctaataa cttcttccgc   1320
cagattggtt cggcattggg tgcttccatc gtgggttcga tgttcattca caatatgcag   1380
aatgagatgg ctacccgttt gcctgatgcc cttgcatcgt tgggcaagga aggcgccgct   1440
atttcgcagc agttccaagg tgcagatgcc gccaactcgt tgactccgca cgcagtgcaa   1500
gagcttcccg atgtcctccg tgacgctatc ttaaattcct acaatgacgg tctgaccccc   1560
gtgattggca tgatggtgcc actgccatt gttgcaatgc tgattttgtt cccactgcgc   1620
caagagcgct tgaaggaaac catcgaataa                                    1650

SEQ ID NO: 84          moltype = DNA   length = 1650
FEATURE                Location/Qualifiers
misc_feature           1..1650
                       note = impE2(N458K)
source                 1..1650
                       mol_type = other DNA
                       organism = unidentified
SEQUENCE: 84
atggtagcta aaaactccac cccaagcacg gccggccacg ccagtgctca cactgcggaa     60
gaattcccag tggccaatgc tgaaatggca acgccttcag caatcgaccc aaaccacggt    120
aaaaagaccg cggataacgt cggcattatc ttcgctgcct tgatgctcac catgctgatg    180
agctctttgg ggcagatgat ttfcggttcc gctctgccaa ccatcgtcgg cgagctcggc    240
ggcgtggacc agatgagctg ggtaatttca gcatttatgg tcaccatgac cattgctatg    300
ccactagccg tcagctcgg tgaccgcatg ggccgcaagt gggtctacat ctcaggtatc    360
tccattttcg ttattggctc gacgtcggg ggctttgcca atggcatggg catgctgatc    420
accggacgtg caatccaggg cttcggtgcc ggcatcatga tgatttcctc gcagtcgatt    480
gtggctgagg ttgtctccgc acgtgagcgc ggcaagttca tgggtattat gggcggcgtc    540
tttggcgtct cctccgtact gggtccagtt ctcggtggct ggttcaccga tggtcccggt    600
tggcgttggg gcctgtggat caacattcca ctgggtctgc tggcaattat tgtctgcgct    660
ttcgtactga agctgcgcgt gggcgagcaa ggctttaagg gctttgactg gatgggtttt    720
gcggccatcg caatcacgac cagcaccctg attctgctca ccacttgggg cggaagcgaa    780
tacgagtgga cttccccaac tattttgtcc atggctgccg tagtcatcgt cggcgcgctg    840
ctcaccgtgt tcattgagtc gcgtgcatcc cagccgctga tcccggttca gctatttaag    900
aaccgcaaca tggttttgac caccctcgcc ggtactgttt tgggtctggc catgatgggc    960
gtgctcggct acatgccaac ctacctgcag atggtgcaca ccctgacgcc aactgaagca   1020
ggcttgatga tgatcccgat gatggtcggc atgatcggtg tctccactgg tgttggcttc   1080
atcatcgcta agaccggcaa ctacaagtac taccccatcg cgggcctggc catcacggcc   1140
tttgctttgt ggtggatgtc ccagatgacc gttgagactt cattgaccgg tatcggagtt   1200
cgcttccttg tattcggtgt cggcttgggc tttgtcacgc aggtactggt gctgattgtt   1260
caaaactcct tccctgtatc gcaggtcggg actgccacgg cggctaataa cttcttccgc   1320
cagattggtt cggcattggg tgcttccatc gtgggttcga tgttcattca aaaatgcag   1380
aatgagatgg ctacccgttt gcctgatgcc cttgcatcgt tgggcaagga aggcgccgct   1440
atttcgcagc agttccaagg tgcagatgcc gccaactcgt tgactccgca cgcagtgcaa   1500
gagcttcccg atgtcctccg tgacgctatc ttaaattcct acaatgacgg tctgaccccc   1560
gtgattggca tgatggtgcc actgccatt gttgcaatgc tgattttgtt cccactgcgc   1620
caagagcgct tgaaggaaac catcgaataa                                    1650

SEQ ID NO: 85          moltype = AA    length = 221
FEATURE                Location/Qualifiers
REGION                 1..221
                       note = ImpE1 - CJI0323
source                 1..221
                       mol_type = protein
                       organism = unidentified
SEQUENCE: 85
LHAVQEVNDN EEDSLPGSDL GLREQKRLAT KHRIEDAATR LVDESSFDKV TIEEICEAAG     60
ISRRTFFNYF STKESAVIGA SSEPLTEKQR NDFLNADASN LLQLMVEQIK QHLESSHQSQ    120
AIHDRRQRIF ADPDVAVRAM AFRKERSRET MELIAQRLRE HPEKQRAPEL DPETEAMLLS    180
GFIREATWMA ISRPDRDCAL PVGDRIYRAM ELVKNYTKGL E                        221

SEQ ID NO: 86          moltype = AA    length = 549
FEATURE                Location/Qualifiers
REGION                 1..549
                       note = ImpE2 - CJI0323
source                 1..549
                       mol_type = protein
                       organism = unidentified
SEQUENCE: 86
MIAKNSTPST AGHASAHTAE EFPVANAEMA TPSAIDPNHG KKTADNVGII FAALMLTMLM     60
SSLEQMIFGS ALPTIVGELG GVDQMSWVIS AFMVTMTIAM PLAGQLGDRM GRKWVYISGI    120
SIFVIGSTLG GFANGMGMLI TGRAIQGFGA GIMMISSQSI VAEVVSARER GKFMGIMGGV    180
```

```
FGVSSVLGPV LGGWFTDGPG WRWGLWINIP LGLLAIIVCA FVLKLRVGEQ GFKGFDWMGF    240
AAIAITTSTL ILLTTWGGSE YEWTSPTILS MAAVVIVGAL LTVFIESRAS QPLIPVQLFK    300
NRNMVLTTLA GTVLGLAMMG VLGYMPTYLQ MVHTLTPTEA GLMMIPMMVG MIGVSTGVGF    360
IIAKTGNYKY YPIAGLAITA FALWWMSQMT VETSLTGIGV RFLVFGVGLG FVMQVLVLIV    420
QNSFPVSQVG TATAANNFFR QIGSALGASI VGSMFIHNMQ NEMATRLPDA LASLGKEGAA    480
ISQQFQGADA ANSLTPHAVA ELPDVLRDAI LNSYNDGLTP VIGMMVPLAI VAMLILFPLR    540
QERLKETIE                                                           549

SEQ ID NO: 87            moltype = DNA   length = 669
FEATURE                  Location/Qualifiers
misc_feature             1..669
                         note = ImpE1 NT - CJI0323
source                   1..669
                         mol_type = other DNA
                         organism = unidentified
SEQUENCE: 87
ttgcatgctg tgcaagaagt taatgacaat gaagaagact ccctccctgg cagtgacctc     60
gggttaaggg agcagaagcg attggcaacc aagcatcgca tcgaagacgc cgcgacacgg    120
ttggttgatg aatcgagctt tgacaaagta acaattgaag aaatttgcga agccgccggg    180
atttcccgac gcacctttt taattattc agcacgaaag aaagcgccgt tattggcgcg    240
tcctcggaac cgttgacgga aaagcaacgc aatgacttct gaatgctga cgccagcaat    300
ctcctgcagc tgatggttga gcagatcaaa caacacttgg agtcttctca ccagagtcaa    360
gcgattcacg accgtcgtca gcgaatcttt gcggatccgg atgtcgcggt acgtgcaatg    420
gcgtttcgca aggaacgctc acgggaaacc atggagctaa tcgctcaacg tcttcggag    480
catcctgaaa acaacgcgc cccagaattg atccggaaa cagaggcgat gctgctgagc    540
ggattcattc gcgaagccac ctggatggct atctcacgac ccgatcgtga ttgtgcactg    600
ccagtgggtg accgcatcta tcgcgcgatg gaattggtaa agaattacac gaaaggactg    660
gaatgatag                                                           669

SEQ ID NO: 88            moltype = DNA   length = 1650
FEATURE                  Location/Qualifiers
misc_feature             1..1650
                         note = ImpE2 NT - CJI0323
source                   1..1650
                         mol_type = other DNA
                         organism = unidentified
SEQUENCE: 88
atgatagcta aaaactccac cccaagcacg gccggccacg ccagtgctca cactgcggaa     60
gaattcccag tggccaatgc tgaaatggca acgccttcag caatcgaccc aaaccacggt    120
aaaaagaccg cggataacgt cggcattatc ttcgctgcct tgatgctcac catgctgatg    180
agctctttgg agcagatgat tttcggttcc gctctgccaa ccatcgtcgg cgagctcggc    240
ggcgtggacc agatgagctg gtaatttca gcatttatgg tcaccatgac cattgctatg    300
ccactagccg gtcagctcgg tgaccgcatg ggccgcaagt ctcaggtatc tccatttcg    360
ttattggctc gacgctcggg ggctttgcca atggcatggg catgctgatc    420
accgacgtg caatccaggg cttcggtgcc ggcatcatga tgatttcctc gcagtcgatt    480
gtggctgagg ttgtctccgc acgtgagcgc ggcaagttca tgggtattat gggcggcgtc    540
tttggctgtct cctccgtact gggtccagtt ctcggtggct ggttcaccga tgggtccgt    600
tggcgttggg gcctgtggat caacattcca ctgggtctgc tggcaattat tgtctgcgct    660
ttcgtactga agctgcgcgt gggcgagcaa ggctttaagg gctttgactg gatgggtttt    720
gcggccatcg caatcacgac cagcaccctg attctgctca ccacttgggg cggaagcgaa    780
tacgagtgga cttccccaac tatttttgtcc atggctgcca tagtcatcgt cggccgcgtc    840
ctcaccgtgt tcattgagtc gcgtgcatcc cagccgctga tcccggttca gctatttaag    900
aaccgcaaca tggttttgac caccctcgcc ggtactgttt tgggtctggc catgatgggc    960
gtgctcggct acatgccaac ctacctgcag atggtgcaca ccctgacgcc aactgaagca   1020
ggcttgatga tgatcccgat gatggtcggc atgatcggtg tctccactgg tgttggcttc   1080
atcatcgcta agaccggcaa ctacaagtac taccccatcg cgggcctggc catcacggcg   1140
tttgctttgt ggtggatgtc ccagatgacc gttgagactt cattgaccgg tatcggagtt   1200
cgcttccttg tattcggtgt cggcttgggc tttgtcatgc aggtactggt gctgattgtt   1260
caaaactcct tccctgtatc gcaggtcggt actgccacgg cggctaataa cttcttccgc   1320
cagattggtt cggcattggg tgcttccatc gtgggttcga tgttcattca caatatgcag   1380
aatgagatgg ctaccgtttt gcctgatgcc cttgcatcgt tgggcaagga aggcgccgct   1440
atttcgcagc agttccaagg tgcagatgcc gccaactcct tgactccgca cgcagtcgca   1500
gagcttcccg atgtcctccg tgacgctatc ttaaattcct acaatgacgg tctgacccc   1560
gtgattggca tgatggtgcc actggccatt gttgcaatgc tgattttgtt cccactgcgc   1620
caagagcgct tgaaggaaac catcgaataa                                    1650

SEQ ID NO: 89            moltype = DNA   length = 29
FEATURE                  Location/Qualifiers
misc_feature             1..29
                         note = Primer impE1E2 WT F
source                   1..29
                         mol_type = other DNA
                         organism = synthetic construct
SEQUENCE: 89
gctctagaga acggagtcat ctcctttgc                                       29

SEQ ID NO: 90            moltype = DNA   length = 30
FEATURE                  Location/Qualifiers
misc_feature             1..30
```

```
                        note        = Primer impE1E2 WT R
source                  1..30
                        mol_type    = other DNA
                        organism    = synthetic construct
SEQUENCE: 90
gctctagacc aaacgctctg caagaaactg                                        30

SEQ ID NO: 91           moltype = DNA  length = 29
FEATURE                 Location/Qualifiers
misc_feature            1..29
                        note        = Primer impE1 164K-1
source                  1..29
                        mol_type    = other DNA
                        organism    = synthetic construct
SEQUENCE: 91
gctctagact tggatgacct ggtggaaaa                                         29

SEQ ID NO: 92           moltype = DNA  length = 37
FEATURE                 Location/Qualifiers
misc_feature            1..37
                        note        = Primer impE1 164K-2
source                  1..37
                        mol_type    = other DNA
                        organism    = synthetic construct
SEQUENCE: 92
ctggggcgcg ttgtttttca ggatgctccc gaagacg                                37

SEQ ID NO: 93           moltype = DNA  length = 21
FEATURE                 Location/Qualifiers
misc_feature            1..21
                        note        = Primer impE1 164K-3
source                  1..21
                        mol_type    = other DNA
                        organism    = synthetic construct
SEQUENCE: 93
aacaacgcgc cccagaattg g                                                 21

SEQ ID NO: 94           moltype = DNA  length = 29
FEATURE                 Location/Qualifiers
misc_feature            1..29
                        note        = Primer impE1 164K-4
source                  1..29
                        mol_type    = other DNA
                        organism    = synthetic construct
SEQUENCE: 94
gctctagaaa tagttgggga agtccactc                                         29

SEQ ID NO: 95           moltype = DNA  length = 37
FEATURE                 Location/Qualifiers
misc_feature            1..37
                        note        = Primer impE2 V2I-2
source                  1..37
                        mol_type    = other DNA
                        organism    = synthetic construct
SEQUENCE: 95
tggagttttt agctatcatt ccagtccttt cgtgtaa                                37

SEQ ID NO: 96           moltype = DNA  length = 21
FEATURE                 Location/Qualifiers
misc_feature            1..21
                        note        = Primer impE2 V2I-3
source                  1..21
                        mol_type    = other DNA
                        organism    = synthetic construct
SEQUENCE: 96
tagctaaaaa ctccacccca a                                                 21

SEQ ID NO: 97           moltype = DNA  length = 37
FEATURE                 Location/Qualifiers
misc_feature            1..37
                        note        = Primer impE2 G64E-2
source                  1..37
                        mol_type    = other DNA
                        organism    = synthetic construct
SEQUENCE: 97
ccgaaaatca tctgctccaa agagctcatc agcatgg                                37

SEQ ID NO: 98           moltype = DNA  length = 21
FEATURE                 Location/Qualifiers
```

```
misc_feature            1..21
                        note = Primer impE2 G64E-3
source                  1..21
                        mol_type = other DNA
                        organism = synthetic construct
SEQUENCE: 98
gcagatgatt tcggttccg c                                                    21

SEQ ID NO: 99           moltype = AA  length = 549
FEATURE                 Location/Qualifiers
REGION                  1..549
                        note = impE2 CJI0323 64D
source                  1..549
                        mol_type = protein
                        organism = unidentified
SEQUENCE: 99
MIAKNSTPST AGHASAHTAE EFPVANAEMA TPSAIDPNHG KKTADNVGII FAALMLTMLM    60
SSLDQMIFGS ALPTIVGELG GVDQMSWVIS AFMVTMTIAM PLAGQLGDRM GRKWVYISGI   120
SIFVIGSTLG GFANGMGMLI TGRAIQGFGA GIMMISSQSI VAEVVSARER GKFMGIMGGV   180
FGVSSVLGPV LGGWFTDGPG WRWGLWINIP LGLLAIIVCA FVLKLRVGEQ GFKGFDWMGF   240
AAIAITTSTL ILLTTWGGSE YEWTSPTILS MAAVVIVGAL LTVFIESRAS QPLIPVQLFK   300
NRNMVLTTLA GTVLGLAMMG VLGYMPTYLQ MVHTLTPTEA GLMMIPMMVG MIGVSTGVGF   360
IIAKTGNYKY YPIAGLAITA FALWWMSQMT VETSLTGIGV RFLVFGVGLG FVMQVLVLIV   420
QNSFPVSQVG TATAANNFFR QIGSALGASI VGSMFIHNMQ NEMATRLPDA LASLGKEGAA   480
ISQQFQGADA ANSLTPHAVA ELPDVLRDAI LNSYNDGLTP VIGMMVPLAI VAMLILFPLR   540
QERLKETIE                                                            549

SEQ ID NO: 100          moltype = DNA  length = 1650
FEATURE                 Location/Qualifiers
misc_feature            1..1650
                        note = impE2 CJI0323 64D
source                  1..1650
                        mol_type = other DNA
                        organism = unidentified
SEQUENCE: 100
atgatagcta aaaactccac cccaagcacg gccggccacg ccagtgctca cactgcggaa      60
gaattcccag tggccaatgc tgaaatggca acgccttcag caatcgaccc aaaccacggt    120
aaaaagaccg cggataacgt cggcattatc ttcgctgcct tgatgctcac catgctgatg    180
agctctttgg accagatgat tttcggttcc gctctgccaa ccatcgtcgg cgagctgggt    240
ggcgtggacc agatgagctg ggtaatttca gcatttatgg tcaccatgac cattgctatg    300
ccactagccg gtcagctcgg tgaccgcatg ggccgcaagt gggtctacat ctcaggtatc    360
tccatttctg ttattggctc gacgctcggt ggctttgcca atggcatggg catgctgatc    420
accggacgtg caatccaggg cttcggtgcc ggcatcatga tgatttcctc gcagtcgatt    480
gtggctgagg ttgtctccgc acgtgagcgc ggcaagttca tgggtattat gggcggcgtc    540
tttggcgtct cctccgtact gggtccagtt ctcggtggct ggttcaccga tggtcccggt    600
tggcgttggg gcctgtggat caacattcca ctgggtctgc tggcaattat tgtctgcgct    660
ttcgtactga agctgcgcgt gggcgagcaa ggctttaagg gctttgactg gatgggtttt    720
gcggccatcg caatcacgac cagcaccctg attctgctca ccacttgggg cggaagcgaa    780
tacgagtgga cttccccaac tattttgtcc atggctgccg tagtcatcgt cggcgcgctg    840
ctcaccgtgt tcattgagtc gcgtgcatcc cagccgctga tccgggttca gctatttaag    900
aaccgcaaca tggttttgac caccctcgcc ggtactgttt tgggtctggc catgatgggt    960
gtgctcggct acatgccaac ctacctgcag atggtgcaca ccctgacgcc aactgaagca   1020
ggcttgatga tgatcccgat gatggtcggc atgatcggtg tctccactgg tgttggcttc   1080
atcatcgcta agaccggcaa ctacaagtac taccccatcg cgggcctggc catcacggcg   1140
tttgctttgt ggtggatgtc ccagatgacc gttgagctt cattgaccgg tatcggagtt   1200
cgcttccttg tattcggtgt cggcttgggc tttgtcatgc aggtactggt gctgattgtt   1260
caaaactcct tccctgtatc gcaggtcggt actgccacgg cggctaataa cttcttccgc   1320
cagattggtt cggcattggg tgcttccatc gtgggtcgga tgttcattca caatatgcag   1380
aatgagatgg ctacccgttt gcctgatgcc cttgcatcgt tgggcaagga aggcgccgct   1440
atttcgcagc agttccaagg tgcagatgcc gccaactcct tgactccgca cgcagtcgca   1500
gagcttcccg atgtcctccg tgacgctatc ttaaattcct acaatgacgg tctgacccc   1560
gtgattggca tgatggtgcc actggccatt gttgcaatgc tgatttttgt cccactgcgc   1620
caagagcgct tgaaggaaac catcgaataa                                    1650

SEQ ID NO: 101          moltype = AA  length = 549
FEATURE                 Location/Qualifiers
REGION                  1..549
                        note = impE2(S387T, M413T, N458K)
source                  1..549
                        mol_type = protein
                        organism = unidentified
SEQUENCE: 101
MVAKNSTPST AGHASAHTAE EFPVANAEMA TPSAIDPNHG KKTADNVGII FAALMLTMLM    60
SSLGQMIFGS ALPTIVGELG GVDQMSWVIS AFMVTMTIAM PLAGQLGDRM GRKWVYISGI   120
SIFVIGSTLG GFANGMGMLI TGRAIQGFGA GIMMISSQSI VAEVVSARER GKFMGIMGGV   180
FGVSSVLGPV LGGWFTDGPG WRWGLWINIP LGLLAIIVCA FVLKLRVGEQ GFKGFDWMGF   240
AAIAITTSTL ILLTTWGGSE YEWTSPTILS MAAVVIVGAL LTVFIESRAS QPLIPVQLFK   300
NRNMVLTTLA GTVLGLAMMG VLGYMPTYLQ MVHTLTPTEA GLMMIPMMVG MIGVSTGVGF   360
IIAKTGNYKY YPIAGLAITA FALWWMSQMT VETSLTGIGV RFLVFGVGLG FVTQVLVLIV   420
```

```
QNSFPVSQVG TATAANNFFR QIGSALGASI VGSMFIHKMQ NEMATRLPDA LASLGKEGAA    480
ISQQFQGADA ANSLTPHAVA ELPDVLRDAI LNSYNDGLTP VIGMMVPLAI VAMLILFPLR    540
QERLKETIE                                                           549

SEQ ID NO: 102          moltype = DNA   length = 1650
FEATURE                 Location/Qualifiers
misc_feature            1..1650
                        note = impE2(S387T, M413T, N458K)
source                  1..1650
                        mol_type = other DNA
                        organism = unidentified
SEQUENCE: 102
atggtagcta aaaactccac cccaagcacg gccggccacg ccagtgctca cactgcggaa    60
gaattcccag tggccaatgc tgaaatggca acgccttcag caatcgaccc aaaccacggt   120
aaaaagaccg cggataacgt cggcattatc ttcgctgcct tgatgctcac catgctgatg   180
agctctttgg ggcagatgat tttcggttcc gctctgccaa ccatcgtcgg cgagctcggc   240
ggcgtggacc agatgagctg gtaatttca gcatttatgg tcaccatgac cattgctatg   300
ccactagccg gtcagtcgg tgaccgcatg ggccgcatg ggtctacat ctcaggtatc      360
tccattttcg ttattggctc gacgctcggc ggctttgcca atggcatggg catgctgatc   420
accgacgtg caatccaggg cttcggtgcc ggcatcatga tgatttcctc gcagtcgatt   480
gtggctgagg ttgtctccgc acgtgagcgc ggcaagttca tgggtattat gggcggcgtc   540
tttggcgtct cctccgtact gggtccagtt ctcggtggct ggttcaccga tggtcccggt   600
tggcgttggg gcctgtggat caacattcca ctgggtctgc tggcaattat tgtctgcgct   660
ttcgtactga agctgcgcgt gggcgagcaa ggctttaagg ctttgactg gatgggtttt   720
gcggccatcg caatcacgac cagcaccctg attctgctca ccacttgggg cggaagcgaa   780
tacgagtgga cttcccaac tatttgtcc atggctgacg tagtcatcgt cggcgcgctg    840
ctcaccgtgt tcattgagtc gcgtgcatcc cagccgctga tcccggttca gctatttaag   900
aaccgcaaca tggttttgac caccctcgcc ggtactgttt tgggtctggc catgatgggc   960
gtgctcggct acatgccaac ctacctgcag atggtgcaca ccctgacgcc aactgaagca  1020
ggcttgatga tgatcccgat gatggtcggc atgatcagtg gctccactgg tgttggcttc  1080
atcatcgcta agaccggcaa ctacaagtac taccccatcg cgggcctggc catcacgacg  1140
tttgctttgt ggtggatgac ccagatgacc gttgagactt cattgaccgg tatcggagtt  1200
cgcttccttg tattcggtgt cggcttgggc tttgtcacgc aggtactggt gctgattgtt  1260
caaaactcct ccctgtatc gcaggtcggt actgccacgg cggctaataa cttcttccgc  1320
cagattggtt cggcattggg tgcttccatc gtgggttcga tgttcattca caaatgcag   1380
aatgagatgg ctaccgtttt gcctgatgcc cttgcatcgt tgggcaagga aggcgccgct  1440
atttcgcagc agttccaagg tgcagatgcc gccaactcct tgactccgca cgcagtcgca  1500
gagcttcccg atgtcctccg tgacgctatc ttaaattcct acaatgacgg tctgaccccc  1560
gtgattggca tgatggtgcc actgccatt ttgcaatgc tgattttgtt cccactcgcg    1620
caagagcgct tgaaggaaac catcgaataa                                   1650

SEQ ID NO: 103          moltype = AA    length = 549
FEATURE                 Location/Qualifiers
REGION                  1..549
                        note = impE2(G64D, S387T, M413T, N458K)
source                  1..549
                        mol_type = protein
                        organism = unidentified
SEQUENCE: 103
MVAKNSTPST AGHASAHTAE EFPVANAEMA TPSAIDPNHG KKTADNVGII FAALMLTMLM    60
SSLDQMIFGS ALPTIVGELG GVDQMSWVIS AFMVTMTIAM PLAGQLGDRM GRKWVYISGI   120
SIFVIGSTLG GFANGMGMLI TGRAIQGFGA GIMMISSQSI VAEVVSARER GKFMGIMGGV   180
FGVSSVLGPV LGGWFTDGPG WRWGLWINIP LGLLAIIVCA FVLKLRVGEQ GFKGFDWMGF   240
AAIAITTSTL ILLTTWGGSE YEWTSPTILS MAAVVIVGAL LTVFIESRAS QPLIPVQLFK   300
NRNMVLTTLA GTVLGLAMMG VLGYMPTYLQ MVHTLTPTEA GLMMIPMMVG MIGVSTGVGF   360
IIAKTGNYKY YPIAGLAITA FALWWMTQMT VETSLTGIGV RFLVFGVGLG FVTQVLVLIV   420
QNSFPVSQVG TATAANNFFR QIGSALGASI VGSMFIHKMQ NEMATRLPDA LASLGKEGAA   480
ISQQFQGADA ANSLTPHAVA ELPDVLRDAI LNSYNDGLTP VIGMMVPLAI VAMLILFPLR   540
QERLKETIE                                                          549

SEQ ID NO: 104          moltype = DNA   length = 1650
FEATURE                 Location/Qualifiers
misc_feature            1..1650
                        note = impE2(G64D, S387T, M413T, N458K)
source                  1..1650
                        mol_type = other DNA
                        organism = unidentified
SEQUENCE: 104
atggtagcta aaaactccac cccaagcacg gccggccacg ccagtgctca cactgcggaa    60
gaattcccag tggccaatgc tgaaatggca acgccttcag caatcgaccc aaaccacggt   120
aaaaagaccg cggataacgt cggcattatc ttcgctgcct tgatgctcac catgctgatg   180
agctctttgg accagatgat tttcggttcc gctctgccaa ccatcgtcgg cgagctcggc   240
ggcgtggacc agatgagctg gtaatttca gcatttatgg tcaccatgac cattgctatg   300
ccactagccg gtcagtcgg tgaccgcatg ggccgcatg ggtctacat ctcaggtatc      360
tccattttcg ttattggctc gacgctcggc ggctttgcca atggcatggg catgctgatc   420
accgacgtg caatccaggg cttcggtgcc ggcatcatga tgatttcctc gcagtcgatt   480
gtggctgagg ttgtctccgc acgtgagcgc ggcaagttca tgggtattat gggcggcgtc   540
tttggcgtct cctccgtact gggtccagtt ctcggtggct ggttcaccga tggtcccggt   600
tggcgttggg gcctgtggat caacattcca ctgggtctgc tggcaattat tgtctgcgct   660
```

```
ttcgtactga agctgcgcgt gggcgagcaa ggctttaagg gctttgactg gatgggtttt    720
gcggccatcg caatcacgac cagcacccta attctgctca ccacttgggg cggaagcgaa    780
tacgagtgga cttccccaac tattttgtcc atggctgccg tagtcatcgt cggcgcgctg    840
ctcaccgtgt tcattgagtc gcgtgcatcc cagccgctga tcccggttca gctatttaag    900
aaccgcaaca tggttttgac caccctcgcc ggtactgttt tgggtctggc catgatgggc    960
gtgctcggct acatgccaac ctacctgcag atggtgcaca ccctgacgcc aactgaagca   1020
ggcttgatga tgatcccgat gatggtcggc atgatcggtg tctccactgg tgttggcttc   1080
atcatcgcta agaccggcaa ctacaagtac taccccatcg cgggcctggc catcacggcg   1140
tttgctttgt ggtggatgtc ccagatgacc gttgagactt cattgaccgg tatcggagtt   1200
cgcttccttg tattcggtgt cggcttgggc tttgtcacgc aggtactggt gctgattgtt   1260
caaaactcct tccctgtatc gcaggtcggt actgccacgg cggctaataa cttcttccgc   1320
cagattggtt cggcattggg tgcttccatc gtgggttcga tgttcattca caaatgcag    1380
aatgagatgg ctacccgttt gcctgatgcc cttgcatcgt tgggcaagga aggcgccgct   1440
atttcgcagc agttccaagg tgcagatgcc gccaactcct tgactccgca cgcagtcgca   1500
gagcttcccg atgtcctccg tgacgctatc ttaaattcct acaatgacgg tctgacccc    1560
gtgattggca tgatggtgcc actggccatt gttgcaatgc tgattttgtt cccactgcgc   1620
caagagcgct tgaaggaaac catcgaataa                                     1650

SEQ ID NO: 105             moltype = AA  length = 549
FEATURE                    Location/Qualifiers
REGION                     1..549
                           note = impE2(G64D, F123C)
source                     1..549
                           mol_type = protein
                           organism = unidentified
SEQUENCE: 105
MVAKNSTPST AGHASAHTAE EFPVANAEMA TPSAIDPNHG KKTADNVGII FAALMLTMLM      60
SSLDQMIFGS ALPTIVGELG GVDQMSWVIS AFMVTMTIAM PLAGQLGDRM GRKWVYISGI    120
SICVIGSTLG GFANGMGMLI TGRAIQGFGA GIMMISSQSI VAEVVSARER GKFMGIMGGV    180
FGVSSVLGPV LGGWFTDGPG WRWGLWINIP LGLLAIIVCA FVLKLRVGEQ GFKGFDWMGF    240
AAIAITTSTL ILLTTWGGSE YEWTSPTILS MAAVVIVGAL LTVFIESRAS QPLIPVQLFK    300
NRNMVLTTLA GTVLGLAMMG VLGYMPTYLQ MVHTLTPTEA GLMMIPMMVG MIGVSTGVGF    360
IIAKTGNYKY YPIAGLAITA FALWWMSQMT VETSLTGIGV RFLVFGVGLG FVMQVLVLIV    420
QNSFPVSQVG TATAANNFFR QIGSALGASI VGSMFIHNMQ NEMATRLPDA LASLGKEGAA    480
ISQQFQGADA ANSLTPHAVA ELPDVLRDAI LNSYNDGLTP VIGMMVPLAI VAMLILFPLR    540
QERLKETIE                                                            549

SEQ ID NO: 106             moltype = DNA  length = 1650
FEATURE                    Location/Qualifiers
misc_feature               1..1650
                           note = impE2(G64D, F123C)
source                     1..1650
                           mol_type = other DNA
                           organism = unidentified
SEQUENCE: 106
atggtagcta aaaactccac cccaagcacg gccggccacg ccagtgctca cactgcggaa     60
gaattcccag tggccaatgc tgaaatggca acgccttcag caatcgaccc aaaccacggt    120
aaaaagaccg cggataacgt cggcattatc ttcgctgcct tgatgctcac catgctgatg    180
agctctttgg accagatgat tttcggttcc gctctgccaa ccatcgtcgg cgagctcggc    240
ggcgtggacc agatgagctg ggtaatttca gcatttatgg tcaccatgac cattgctatg    300
ccactagccg gtcagctcgg tgaccgcatg ggccgcaagt gggtctacat ctcaggtatc    360
tccatttgcg ttattggctc gacgctcggg ggctttgcca atggcatggg catgctgatc    420
accggacgtg caatccaggg cttcggtgcc ggcatcatga tgatttcctc gcagtcgatt    480
gtggctgagg ttgtctccgc acgtgagcgc ggcaagttca tgggtattat gggcggcgtc    540
tttggcgtct cctccgtact gggtccagtt ctcggtggct ggttcaccga tggtcccggt    600
tggcgttggg gcctgtggat caacattcca ctgggtctgc tggcaattat tgtctgcgct    660
ttcgtactga agctgcgcgt gggcgagcaa ggctttaagg gctttgactg gatgggtttt    720
gcggccatcg caatcacgac cagcacccta attctgctca ccacttgggg cggaagcgaa    780
tacgagtgga cttccccaac tattttgtcc atggctgccg tagtcatcgt cggcgcgctg    840
ctcaccgtgt tcattgagtc gcgtgcatcc cagccgctga tcccggttca gctatttaag    900
aaccgcaaca tggttttgac caccctcgcc ggtactgttt tgggtctggc catgatgggc    960
gtgctcggct acatgccaac ctacctgcag atggtgcaca ccctgacgcc aactgaagca   1020
ggcttgatga tgatcccgat gatggtcggc atgatcggtg tctccactgg tgttggcttc   1080
atcatcgcta agaccggcaa ctacaagtac taccccatcg cgggcctggc catcacggcg   1140
tttgctttgt ggtggatgtc ccagatgacc gttgagactt cattgaccgg tatcggagtt   1200
cgcttccttg tattcggtgt cggcttgggc tttgtcacgc aggtactggt gctgattgtt   1260
caaaactcct tccctgtatc gcaggtcggt actgccacgg cggctaataa cttcttccgc   1320
cagattggtt cggcattggg tgcttccatc gtgggttcga tgttcattca caatatgcag   1380
aatgagatgg ctacccgttt gcctgatgcc cttgcatcgt tgggcaagga aggcgccgct   1440
atttcgcagc agttccaagg tgcagatgcc gccaactcct tgactccgca cgcagtcgca   1500
gagcttcccg atgtcctccg tgacgctatc ttaaattcct acaatgacgg tctgacccc    1560
gtgattggca tgatggtgcc actggccatt gttgcaatgc tgattttgtt cccactgcgc   1620
caagagcgct tgaaggaaac catcgaataa                                     1650

SEQ ID NO: 107             moltype = AA  length = 549
FEATURE                    Location/Qualifiers
REGION                     1..549
                           note = impE2(G64D, I243V)
source                     1..549
```

```
                        mol_type = protein
                        organism = unidentified
SEQUENCE: 107
MVAKNSTPST AGHASAHTAE EFPVANAEMA TPSAIDPNHG KKTADNVGII FAALMLTMLM    60
SSLDQMIFGS ALPTIVGELG GVDQMSWVIS AFMVTMTIAM PLAGQLGDRM GRKWVYISGI   120
SIFVIGSTLG GFANGMGMLI TGRAIQGFGA GIMMISSQSI VAEVVSARER GKFMGIMGGV   180
FGVSSVLGPV LGGWFTDGPG WRWGLWINIP LGLLAIIVCA FVLKLRVGEQ GFKGFDWMGF   240
AAVAITTSTL ILLTTWGGSE YEWTSPTILS MAAVVIVGAL LTVFIESRAS QPLIPVQLFK   300
NRNMVLTTLA GTVLGLAMMG VLGYMPTYLQ MVHTLTPTEA GLMMIPMMVG MIGVSTGVGF   360
IIAKTGNYKY YPIAGLAITA FALWWMSQMT VETSLTGIGV RFLVFGVGLG FVMQVLVLIV   420
QNSFPVSQVG TATAANNFFR QIGSALGASI VGSMFIHNMQ NEMATRLPDA LASLGKEGAA   480
ISQQFQGADA ANSLTPHAVA ELPDVLRDAI LNSYNDGLTP VIGMMVPLAI VAMLILFPLR   540
QERLKETIE                                                          549

SEQ ID NO: 108          moltype = DNA  length = 1650
FEATURE                 Location/Qualifiers
misc_feature            1..1650
                        note = impE2(G64D, I243V)
source                  1..1650
                        mol_type = other DNA
                        organism = unidentified
SEQUENCE: 108
atggtagcta aaaactccac cccaagcacg gccggccacg ccagtgctca cactgcggaa     60
gaattcccag tggccaatgc tgaaatggca acgccttcag caatcgaccc aaaccacggt    120
aaaaagaccg cggataacgt cggcattatc ttcgctgcct tgatgctcac catgctgatg    180
agctctttgg accagatgat tttcggttcc gctctgccaa ccatcgtcgg cgagctcggc    240
ggcgtggacc agatgagctg gtaatttca gcatttatgg tcaccatgac cattgctatg    300
ccactagccg gtcagctcgg tgaccgcatg gccgcaagt gggtctacat ctcaggtatc    360
tccatttcg ttattggctc gacgctcggt ggctttgcca atggcatggg catgctgatc    420
accggacgtg caatccaggg cttcggtgcc ggcatcatga tgatttcctc gcagtgatc    480
gtggctgagg ttgtctccgc acgtgagcgc ggcaagttca tgggtattat gggcggcgtc    540
tttggcgtct cctccgtact gggtccagtt ctcggtggct ggttcaccga tggtcccggt    600
tggcgttggg gcctgtggat caacattcca ctgggtctgc tggcaattat tgtctgcgct    660
ttcgtactga agctgcgcgt gggcgagcaa ggctttaagg gctttgactg gatgggtttt    720
gcggccgtcg caatcacgac cagcaccctg attctgctca ccacttgggg cggaagcgaa    780
tacgagtgga cttccccaac tattttgtcc atggctgccg tagtcatcgt cggcgcgctg    840
ctcaccgtgt tcattgagtc gcgtgcatcc cagccgctga tccggttca gctatttaag    900
aaccgcaaca tggttttgac cacccctgcc ggtactgttt tgggtctggc catgatgggc    960
gtgctcggct acatgccaac ctacctgcag atggtgcaca ccctgacgcc aactgaagca   1020
ggcttgatga tgatcccgat gatggtcggc atgatcggtg tctccactgg tgttggcttc   1080
atcatcgcta agaccggcaa ctacaagtac tacccatcg cgggcctggc catcacggcg   1140
tttgcttgtg ggtggatgtc ccagatgacc gttgagactt cattgaccgg tatcggagtt   1200
cgcttccttg tattcggtgt cggcttgggc tttgtcatgc aggtactggt gctgattgtt   1260
caaaactcct tccctgtatc gcaggtcggt actgccacgg cggctaataa cttcttccgc   1320
cagattggtt cggcattggg tgcttccatc gtggggttcga tgttcattca caatatgcag   1380
aatgagatgg ctaccgtttt gcctgatgcc cttgcatcgt tgggcaagga aggcgccgct   1440
atttcgcagc agttccaagg tgcagatgcc gccaactcgt tgactccgca cgcagtcgca   1500
gagcttcccg atgtcctccg tgacgctatc ttaaattcct acaatgacgg tctgaccccc   1560
gtgattggca tgatggtgcc actgccatt gttgcaatgc tgattttgtt cccactgcgc   1620
caagagcgct tgaaggaaac catcgaataa                                    1650

SEQ ID NO: 109          moltype = AA  length = 549
FEATURE                 Location/Qualifiers
REGION                  1..549
                        note = impE2(G64D, F405Y)
source                  1..549
                        mol_type = protein
                        organism = unidentified
SEQUENCE: 109
MVAKNSTPST AGHASAHTAE EFPVANAEMA TPSAIDPNHG KKTADNVGII FAALMLTMLM    60
SSLDQMIFGS ALPTIVGELG GVDQMSWVIS AFMVTMTIAM PLAGQLGDRM GRKWVYISGI   120
SIFVIGSTLG GFANGMGMLI TGRAIQGFGA GIMMISSQSI VAEVVSARER GKFMGIMGGV   180
FGVSSVLGPV LGGWFTDGPG WRWGLWINIP LGLLAIIVCA FVLKLRVGEQ GFKGFDWMGF   240
AAIAITTSTL ILLTTWGGSE YEWTSPTILS MAAVVIVGAL LTVFIESRAS QPLIPVQLFK   300
NRNMVLTTLA GTVLGLAMMG VLGYMPTYLQ MVHTLTPTEA GLMMIPMMVG MIGVSTGVGF   360
IIAKTGNYKY YPIAGLAITA FALWWMSQMT VETSLTGIGV RFLVYGVGLG FVMQVLVLIV   420
QNSFPVSQVG TATAANNFFR QIGSALGASI VGSMFIHNMQ NEMATRLPDA LASLGKEGAA   480
ISQQFQGADA ANSLTPHAVA ELPDVLRDAI LNSYNDGLTP VIGMMVPLAI VAMLILFPLR   540
QERLKETIE                                                          549

SEQ ID NO: 110          moltype = DNA  length = 1650
FEATURE                 Location/Qualifiers
misc_feature            1..1650
                        note = impE2(G64D, F405Y)
source                  1..1650
                        mol_type = other DNA
                        organism = unidentified
SEQUENCE: 110
atggtagcta aaaactccac cccaagcacg gccggccacg ccagtgctca cactgcggaa     60
```

-continued

```
gaattcccag tggccaatgc tgaaatggca acgccttcag caatcgaccc aaaccacggt    120
aaaaagaccg cggataacgt cggcattatc ttcgctgcct tgatgctcac catgctgatg    180
agctctttgg accagatgat tttcggttcc gctctgccaa ccatcgtcgg cgagctcggc    240
ggcgtggacc agatgagctg ggtaatttca gcatttatgg tcaccatgac cattgctatg    300
ccactagccg gtcagctcgg tgaccgcatg ggccgcaagt gggtctacat ctcaggtatc    360
tccattttcg ttattggctc gacgctcggc ggctttgcca atggcatggg catgctgatc    420
accggacgtg caatccaggg cttcggtgcc ggcatcatga tgatttcctc gcagtcgatt    480
gtggctgagg ttgtctccgc acgtgagcgc ggcaagttca tgggtattat gggcggcgtc    540
tttggcgtct cctccgtact gggtccagtt ctcggtggct ggttcaccga tggtcccggt    600
tggcgttggg gcctgtggat caacattcca ctgggtctgc tggcaattat tgtctgcgct    660
ttcgtactga agctgcgcgt gggcgagcaa ggctttaagg ctttgactg gatgggtttt    720
gcggccatcg caatcacgac cagcaccctg attctgctca ccacttgggg cggaagcgaa    780
tacgagtgga cttccccaac tattttgtcc atggctgccg tagtcatcgt cggcgcgctg    840
ctcaccgtgt tcattgagtc gcgtgcatcc cagccgctga tcccggttca gctatttaag    900
aaccgcaaca tggttttgac caccctcgcc ggtactgttt tgggtctggc catgatgggc    960
gtgctcggct acatgccaac ctacctgcag atggtgcaca ccctgacgcc aactgaagca   1020
ggcttgatga tgatcccgat gatggtcggc atgatcggtg tctccactgg tgttggcttc   1080
atcatcgcta agaccggcaa ctacaagtac taccccatcg cgggcctggc catcacgggc   1140
tttgctttgt ggtggatgtc ccagatgacc gttgagactt cattgaccgg tatcggagtt   1200
cgcttccttg tatacggtgt cggcttgggc tttgtcatgc aggtactggt gctgattgtt   1260
caaaactcct tccctgtatc gcaggtcggt actgccacgg cggctaataa cttcttccgc   1320
cagattggtt cggcattggg tgcttccatc gtgggttcga tgttcattca caaatgcag   1380
aatgagatgg ctaccgtttt gcctgatgcc cttgcatcgt tgggcaagga aggcgccgct   1440
atttcgcagc agttccaagg tcagatgcc gccaactcct tgactccgca cgcagtcgca   1500
gagcttcccg atgtcctccg tgacgctatc ttaaattcct acaatgacgg tctgacccc   1560
gtgattggca tgatggtgcc actggccatt gttgcaatgc tgattttgtt cccactgcgc   1620
caagagcgct tgaaggaaac catcgaataa                                   1650
```

SEQ ID NO: 111          moltype = AA  length = 549
FEATURE                 Location/Qualifiers
REGION                  1..549
                        note = impE2(F123C, I243V, S387T, F405Y, M413T, N458K)
source                  1..549
                        mol_type = protein
                        organism = unidentified
SEQUENCE: 111
MVAKNSTPST AGHASAHTAE EFPVANAEMA TPSAIDPNHG KKTADNVGII FAALMLTMLM    60
SSLGQMIFGS ALPTIVGELG GVDQMSWVIS AFMVTMTIAM PLAGQLGDRM GRKWVYISGI   120
SICVIGSTLG GFANGMGMLI TGRAIQGFGA GIMMISSQSI VAEVVSARER GKFMGIMGGV   180
FGVSSVLGPV LGGWFTDGPG WRWGLWINIP LGLLAIIVCA FVLKLRVGEQ GFKGFDWMGF   240
AAVAITTSTL ILLTTWGGSE YEWTSPTILS MAAVVIVGAL LTVFIESRAS QPLIPVQLFK   300
NRNMVLTTLA GTVLGLAMMG VLGYMPTYLQ MVHTLTPEA GLMMIPMMVG MIGVSTGVGF   360
IIAKTGNYKY YPIAGLAITA FALWWMTQMT VETSLTGIGV RFLVYGVGLG FVTQVLVLIV   420
QNSFPVSQVG TATAANNFFR QIGSALGASI VGSMFIHKMQ NEMATRLPDA LASLGKEGAA   480
ISQQFQGADA ANSLTPHAVA ELPDVLRDAI LNSYNDGLTP VIGMMVPLAI VAMLILFPLR   540
QERLKETIE                                                         549

SEQ ID NO: 112          moltype = DNA  length = 1650
FEATURE                 Location/Qualifiers
misc_feature            1..1650
                        note = impE2(F123C, I243V, S387T, F405Y, M413T, N458K)
source                  1..1650
                        mol_type = other DNA
                        organism = unidentified
SEQUENCE: 112
```
```
atggtagcta aaaactccac cccaagcacg gccggccacg ccagtgctca cactgcggaa     60
gaattcccag tggccaatgc tgaaatggca acgccttcag caatcgaccc aaaccacggt    120
aaaaagaccg cggataacgt cggcattatc ttcgctgcct tgatgctcac catgctgatg    180
agctctttgg ggcagatgat tttcggttcc gctctgccaa ccatcgtcgg cgagctcggc    240
ggcgtggacc agatgagctg ggtaatttca gcatttatgg tcaccatgac cattgctatg    300
ccactagccg gtcagctcgg tgaccgcatg ggccgcaagt gggtctacat ctcaggtatc    360
tccatttgcg ttattggctc gacgctcggc ggctttgcca atggcatggg catgctgatc    420
accggacgtg caatccaggg cttcggtgcc ggcatcatga tgatttcctc gcagtcgatt    480
gtggctgagg ttgtctccgc acgtgagcgc ggcaagttca tgggtattat gggcggcgtc    540
tttggcgtct cctccgtact gggtccagtt ctcggtggct ggttcaccga tggtcccggt    600
tggcgttggg gcctgtggat caacattcca ctgggtctgc tggcaattat tgtctgcgct    660
ttcgtactga agctgcgcgt gggcgagcaa ggctttaagg ctttgactg gatgggtttt    720
gcggccgtcg caatcacgac cagcaccctg attctgctca ccacttgggg cggaagcgaa    780
tacgagtgga cttccccaac tattttgtcc atggctgccg tagtcatcgt cggcgcgctg    840
ctcaccgtgt tcattgagtc gcgtgcatcc cagccgctga tcccggttca gctatttaag    900
aaccgcaaca tggttttgac caccctcgcc ggtactgttt tgggtctggc catgatgggc    960
gtgctcggct acatgccaac ctacctgcag atggtgcaca ccctgacgcc aactgaagca   1020
ggcttgatga tgatcccgat gatggtcggc atgatcggtg tctccactgg tgttggcttc   1080
atcatcgcta agaccggcaa ctacaagtac taccccatcg cgggcctggc catcacgggc   1140
tttgctttgt ggtggatgac ccagatgacc gttgagactt cattgaccgg tatcggagtt   1200
cgcttccttg tatacggtgt cggcttgggc tttgtcacgc aggtactggt gctgattgtt   1260
caaaactcct tccctgtatc gcaggtcggt actgccacgg cggctaataa cttcttccgc   1320
cagattggtt cggcattggg tgcttccatc gtgggttcga tgttcattca caaaatgcag   1380
aatgagatgg ctaccgtttt gcctgatgcc cttgcatcgt tgggcaagga aggcgccgct   1440
```

```
atttcgcagc agttccaagg tgcagatgcc gccaactcct tgactccgca cgcagtcgca 1500
gagcttcccg atgtcctccg tgacgctatc ttaaattcct acaatgacgg tctgaccccc 1560
gtgattggca tgatggtgcc actggccatt gttgcaatgc tgattttgtt cccactgcgc 1620
caagagcgct tgaaggaaac catcgaataa                                  1650

SEQ ID NO: 113          moltype = AA   length = 549
FEATURE                 Location/Qualifiers
REGION                  1..549
                        note = impE2(G64D, S387T)
source                  1..549
                        mol_type = protein
                        organism = unidentified
SEQUENCE: 113
MVAKNSTPST AGHASAHTAE EFPVANAEMA TPSAIDPNHG KKTADNVGII FAALMLTMLM  60
SSLDQMIFGS ALPTIVGELG GVDQMSWVIS AFMVTMTIAM PLAGQLGDRM GRKWVYISGI 120
SIFVIGSTLG GFANGMGMLI TGRAIQGFGA GIMMISSQSI VAEVVSARER GKFMGIMGGV 180
FGVSSVLGPV LGGWFTDGPG WRWGLWINIP LGLLAIIVCA FVLKLRVGGE QGFKGFDWMGF 240
AAIAITTSTL ILLTTWGGSE YEWTSPTILS MAAVVIVGAL LTVFIESRAS QPLIPVQLFK 300
NRNMVLTTLA GTVLGLAMMG VLGYMPTYLQ MVHTLTPTEA GLMMIPMMVG MIGVSTGVGF 360
IIAKTGNYKY YPIAGLAITA FALWWMTQMT VETSLTGIGV RFLVFGVGLG FVMQVLVLIV 420
QNSFPVSQVG TATAANNFFR QIGSALGASI VGSMFIHNMQ NEMATRLPDA LASLGKEGAA 480
ISQQFQGADA ANSLTPHAVA ELPDVLRDAI LNSYNDGLTP VIGMMVPLAI VAMLILFPLR 540
QERLKETIE                                                         549

SEQ ID NO: 114          moltype = DNA   length = 1650
FEATURE                 Location/Qualifiers
misc_feature            1..1650
                        note = impE2(G64D, S387T)
source                  1..1650
                        mol_type = other DNA
                        organism = unidentified
SEQUENCE: 114
atggtagcta aaaactccac cccaagcacg gccggccacg ccagtgctca cactgcggaa  60
gaattcccag tggccaatgc tgaaatggca acgccttcag caatcgaccc aaaccacggt 120
aaaaagaccg cggataacgt cggcattatc ttcgctgcct tgatgctcac catgctgatg 180
agctctttgg accagatgat tttcggttcc gctctgccaa ccatcgtcgg cgagctcggc 240
ggcgtggacc agatgagctg ggtaatttca gcatttatgg tcaccatgac cattgctatg 300
ccactagccg gtcagctcgg tgaccgcatg ggccgcaagt gggtctacat ctcaggtatc 360
tccattttcg ttattggctc gacgctcggt ggctttgcca atggcatggg catgctgatc 420
accggacgtg caatccaggg cttcggtgcc ggcatcatga tgatttcctc gcagtcgatt 480
gtggctgagg ttgtctccgc acgtgagcgc ggcaagttca tgggtattat gggcggcgtc 540
tttggcgtct cctccgtact gggtccagtt ctcggtggct ggttcaccga tggtcccggt 600
tggcgttggg gcctgtggat caacattcca ctgggtctgc tggcaattat tgtctgcgct 660
ttcgtactga agctgcgcgt gggcgagcaa ggctttaagg gctttgactg gatgggtttt 720
gcggccatcg caatcacgac cagcaccctg attctgctca ccacttgggg cggaagcgaa 780
tacgagtgga cttccccaac tatttttgtcc atggctgccg tagtcatcgt cggcgcgctg 840
ctcaccgtgt tcattgagtc gcgtgcatcc cagccgctga tccccggttca gctatttaag 900
aaccgcaaca tggttttgac cacccctcgcc ggtactgttt tgggtctggc catgatgggc 960
gtgctcggct acatgccaac ctacctgcag atggtgcaca ccctgacgcc aactgaagca 1020
ggcttgatga tgatcccgat gatggtcggc atgatcggtg tctccactgg tgttggcttc 1080
atcatcgcta agaccggcaa ctacaagtac taccccatcg cgggcctggc catcacggcg 1140
tttgcttttgt ggtggatgac ccagatgacc gttgagactt cattgaccgg tatcggagtt 1200
cgcttccttg tattcggtgt cggcttgggc tttgtcatgc aggtactggt gctgattgtt 1260
caaaactcct ccctgtatc gcaggtcggt actgccacgg cggctaataa cttcttccgc 1320
cagattggtt cggcattggg tgcttccatc gtggggttga tgttcattca caatatgcag 1380
aatgagatgg ctaccgtttt gcctgatgcc cttgcatcgt tgggcaagga aggcgccgct 1440
atttcgcagc agttccaagg tgcagatgcc gccaactcct tgactccgca cgcagtcgca 1500
gagcttcccg atgtcctccg tgacgctatc ttaaattcct acaatgacgg tctgaccccc 1560
gtgattggca tgatggtgcc actggccatt gttgcaatgc tgattttgtt cccactgcgc 1620
caagagcgct tgaaggaaac catcgaataa                                  1650

SEQ ID NO: 115          moltype = AA   length = 549
FEATURE                 Location/Qualifiers
REGION                  1..549
                        note = impE2(G64D, M413T)
source                  1..549
                        mol_type = protein
                        organism = unidentified
SEQUENCE: 115
MVAKNSTPST AGHASAHTAE EFPVANAEMA TPSAIDPNHG KKTADNVGII FAALMLTMLM  60
SSLDQMIFGS ALPTIVGELG GVDQMSWVIS AFMVTMTIAM PLAGQLGDRM GRKWVYISGI 120
SIFVIGSTLG GFANGMGMLI TGRAIQGFGA GIMMISSQSI VAEVVSARER GKFMGIMGGV 180
FGVSSVLGPV LGGWFTDGPG WRWGLWINIP LGLLAIIVCA FVLKLRVGGE QGFKGFDWMGF 240
AAIAITTSTL ILLTTWGGSE YEWTSPTILS MAAVVIVGAL LTVFIESRAS QPLIPVQLFK 300
NRNMVLTTLA GTVLGLAMMG VLGYMPTYLQ MVHTLTPTEA GLMMIPMMVG MIGVSTGVGF 360
IIAKTGNYKY YPIAGLAITA FALWWMSQMT VETSLTGIGV RFLVFGVGLG FVTQVLVLIV 420
QNSFPVSQVG TATAANNFFR QIGSALGASI VGSMFIHNMQ NEMATRLPDA LASLGKEGAA 480
ISQQFQGADA ANSLTPHAVA ELPDVLRDAI LNSYNDGLTP VIGMMVPLAI VAMLILFPLR 540
QERLKETIE                                                         549
```

SEQ ID NO: 116         moltype = DNA   length = 1650
FEATURE                Location/Qualifiers
misc_feature           1..1650
                       note = impE2(G64D, M413T)
source                 1..1650
                       mol_type = other DNA
                       organism = unidentified
SEQUENCE: 116
atggtagcta aaaactccac cccaagcacg gccggccacg ccagtgctca cactgcggaa    60
gaattcccag tggccaatgc tgaaatggca acgccttcag caatcgaccc aaaccacggt   120
aaaaagaccg cggataacgt cggcattatc ttcgctgcct tgatgctcac catgctgatg   180
agctctttgg accagatgat tttcggttcc gctctgccaa ccatcgtcgg cgagctcggc   240
ggcgtggacc agatgagctg ggtaaattca gcatttgtga tcaccatgac cattgctatg   300
ccactagccg gtcagctcgg tgaccgcatg ggccgcaagt gggtctacat ctcaggtatc   360
tccattttcg ttattggctc gacgctcggt ggctttgcca atggcatggg catgctgatc   420
accggacgtg caatccaggg cttcggtgcc ggcatcatga tgatttcctc gcagtcgatt   480
gtggctgagg ttgtctccgc acgtgagcgc ggcaagttca tgggtattat gggcggcgtc   540
tttggcgtct cctccgtact gggtccagtt ctcggtggct ggttcaccga tggtcccggt   600
tggcgttggg gcctgtggat caacattcca ctgggtctgc tggcaattat tgtctgcgct   660
ttcgtactga agctgcgcgt gggcgagcaa ggctttaagg gctttgactg gatgggtttt   720
gcggccatcg caatcacgac cagcaccctg attctgctca ccacttgggg cggaagcgaa   780
tacgagtgga cttccccaac tatttttgtcc atggctgccg tagtcatcgt cggcgcgctg   840
ctcaccgtgt tcattgagtc gcgtgcatcc cagccgctga tcccggttca gctatttaag   900
aaccgcaaca tggttttgac caccctcgcc ggtactgttt gggtctggc catgatgggc   960
gtgctggct acatgccaac ctacctgcag atggtgcaca ccctgacgcc aactgaagca  1020
ggcttgatga tgatcccgat gatggtcggc atgatcggtg tctccactgg tgttggcttc  1080
atcatcgcta agaccggcaa ctacaagtac taccccatcg cgggcctggc catcacggcg  1140
tttgctttgt ggtggatgtc ccagatgacc gttgagactt cattgaccgg tatcggagtt  1200
cgcttccttg tattcggtgt cggcttgggc tttgtcacgc aggtactggt gctgattgtt  1260
caaaactcct tccctgtatc gcaggtcggt actgccacgg cggctaataa cttcttccgc  1320
cagattggtt cggcattggg tgcttccatc gtgggttcga tgttcattca caatatgcag  1380
aatgagatgg ctacccgttt gcctgatgcc cttgcatcgt gggcaagga aggcgccgct  1440
atttcgcagc agttccaagg tgcagatgcc gccaactcct tgactccgca cgcagtgca  1500
gagcttcccg atgtcctccg tgacgctatc taaattcct acaatgacgg tctgacccc  1560
gtgattggca tgatggtgcc actgccatt gttcaatgc tgatttgtt cccactgcgc  1620
caagagcgct tgaaggaaac catcgaataa                                  1650

SEQ ID NO: 117         moltype = AA    length = 549
FEATURE                Location/Qualifiers
REGION                 1..549
                       note = impE2(G64D, N458K)
source                 1..549
                       mol_type = protein
                       organism = unidentified
SEQUENCE: 117
MVAKNSTPST AGHASAHTAE EFPVANAEMA TPSAIDPNHG KKTADNVGII FAALMLTMLM    60
SSLDQMIFGS ALPTIVGELG GVDQMSWVIS AFMVTMTIAM PLAGQLGDRM GRKWVYISGI   120
SIFVIGSTLG GFANGMGMLI TGRAIQGFGA GIMMISSQSI VAEVVSARER GKFMGIMGGV   180
FGVSSVLGPV LGGWFTDGPG WRWGLWINIP LGLLAIIVCA FVLKLRVGEQ GFKGFDWMGF   240
AAIAITTSTL ILLTTWGGSE YEWTSPTILS MAAVVIVGAL LTVFIESRAS QPLIPVQLFK   300
NRNMVLTTLA GTVLGLAMMG VLGYMPTYLQ MVHTLTPTEA GLMMIPMMVG MIGVSTGVGF   360
IIAKTGNYKY YPIAGLAITA FALWWMSQMT VETSLTGIGV RFLVFGVGLG FVMQVLVLIV   420
QNSFPVSQVG TATAANNFFR QIGSALGASI VGSMFIHKMQ NEMATRLPDA LASLGKEGAA   480
ISQQFQGADA ANSLTPHAVA ELPDVLRDAI LNSYNDGLTP VIGMMVPLAI VAMLILFPLR   540
QERLKETIE                                                          549

SEQ ID NO: 118         moltype = DNA   length = 1650
FEATURE                Location/Qualifiers
misc_feature           1..1650
                       note = impE2(G64D, N458K)
source                 1..1650
                       mol_type = other DNA
                       organism = unidentified
SEQUENCE: 118
atggtagcta aaaactccac cccaagcacg gccggccacg ccagtgctca cactgcggaa    60
gaattcccag tggccaatgc tgaaatggca acgccttcag caatcgaccc aaaccacggt   120
aaaaagaccg cggataacgt cggcattatc ttcgctgcct tgatgctcac catgctgatg   180
agctctttgg accagatgat tttcggttcc gctctgccaa ccatcgtcgg cgagctcggc   240
ggcgtggacc agatgagctg ggtaaattca gcatttatgg tcaccatgac cattgctatg   300
ccactagccg gtcagctcgg tgaccgcatg ggccgcaagt gggtctacat ctcaggtatc   360
tccattttcg ttattggctc gacgctcggt ggctttgcca atggcatggg catgctgatc   420
accggacgtg caatccaggg cttcggtgcc ggcatcatga tgatttcctc gcagtcgatt   480
gtggctgagg ttgtctccgc acgtgagcgc ggcaagttca tgggtattat gggcggcgtc   540
tttggcgtct cctccgtact gggtccagtt ctcggtggct ggttcaccga tggtcccggt   600
tggcgttggg gcctgtggat caacattcca ctgggtctgc tggcaattat tgtctgcgct   660
ttcgtactga agctgcgcgt gggcgagcaa ggctttaagg gctttgactg gatgggtttt   720
gcggccatcg caatcacgac cagcaccctg attctgctca ccacttgggg cggaagcgaa   780
tacgagtgga cttccccaac tatttttgtcc atggctgccg tagtcatcgt cggcgcgctg   840

```
ctcaccgtgt tcattgagtc gcgtgcatcc cagccgctga tcccggttca gctatttaag    900
aaccgcaaca tggttttgac caccctcgcc ggtactgttt tgggtctggc catgatgggc    960
gtgctcggct acatgccaac ctacctgcag atggtgcaca ccctgacgcc aactgaagca   1020
ggcttgatga tgatcccgat gatggtcggc atgatcggtg tctccactgg tgttggcttc   1080
atcatcgcta agaccggcaa ctacaagtac taccccatcg cgggcctggc catcacggcg   1140
tttgctttgt ggtggatgtc ccagatgacc gttgagactt cattgaccgg tatcggagtt   1200
cgcttccttg tattcggtgt cggcttgggc tttgtcatgc aggtactggt gctgattgtt   1260
caaaactcct ccctgtatc gcaggtcggt actgccacgg cggctaataa cttcttccgc    1320
cagattggtt cggcattggg tgcttccatc gtgggttcga tgttcattca caaaatgcag   1380
aatgagatgg ctaccgtttt gcctgatgcc cttgcatcgt tgggcaagga aggcgccgct   1440
atttcgcagc agttccaagg tgcagatgcc gccaactcct tgactccgca cgcagtcgca   1500
gagcttcccg atgtcctccg tgacgctatc ttaaattcct acaatgacgg tctgaccccc   1560
gtgattggca tgatggtgcc actggccatt gttgcaatgc tgattttgtt cccactgcgc   1620
caagagcgct tgaaggaaac catcgaataa                                    1650

SEQ ID NO: 119         moltype = AA  length = 549
FEATURE                Location/Qualifiers
REGION                 1..549
                       note = impE2(G64D, I243V, S387T, M413T, N458K)
source                 1..549
                       mol_type = protein
                       organism = unidentified
SEQUENCE: 119
MVAKNSTPST AGHASAHTAE EFPVANAEMA TPSAIDPNHG KKTADNVGII FAALMLTMLM     60
SSLDQMIFGS ALPTIVGELG GVDQMSWVIS AFMVTMTIAM PLAGQLGDRM GRKWVYISGI    120
SIFVIGSTLG GFANGMGMLI TGRAIQGFGA GIMMISSQSI VAEVVSARER GKFMGIMGGV    180
FGVSSVLGPV LGGWFTDGPG WRWGLWINIP LGLLAIIVCA FVLKLRVGEQ GFKGFDWMGF    240
AAVAITTSTL ILLTTWGGSE YEWTSPTILS MAAVVIVGAL LTVFIESRAS QPLIPVQLFK    300
NRNMVLTTLA GTVLGLAMMG VLGYMPTYLQ MVHTLTPTEA GLMMIPMMVG MIGVSTGVGF    360
IIAKTGNYKY YPIAGLAITA FALWWMTQMT VETSLTGIGV RFLVFGVGLG FVTQVLVLIV    420
QNSFPVSQVG TATAANNFFR QIGSALGASI VGSMFIHKMQ NEMATRLPDA LASLGKEGAA    480
ISQQFQGADA ANSLTPHAVA ELPDVLRDAI LNSYNDGLTP VIGMMVPLAI VAMLILFPLR    540
QERLKETIE                                                            549

SEQ ID NO: 120         moltype = DNA  length = 1650
FEATURE                Location/Qualifiers
misc_feature           1..1650
                       note = impE2(G64D, I243V, S387T, M413T, N458K)
source                 1..1650
                       mol_type = other DNA
                       organism = unidentified
SEQUENCE: 120
atggtagcta aaaactccac cccaagcacg gccggccacg ccagtgctca cactgcggaa     60
gaattcccag tggccaatgc tgaaatggca acgccttcag caatcgaccc aaaccacggt    120
aaaaagaccg cggataacgt cggcattatc ttcgctgcct tgatgctcac catgctgatg    180
agctctttgg accagatgat tttcggttcc gctctgccaa ccatcgtcgg cgagctcggc    240
ggcgtggacc agatgagctg ggtaatttca gcatttatgg tcaccatgac cattgctatg    300
ccactagccg gtcagctcgg tgaccgcatg ggccgcaagt gggtctacat ctcaggtatc    360
tccattttcg ttattggctc gacgctcggt ggctttgcca atggcatggg catgctgatc    420
accggacgtg caatccaggg cttcggtgcc ggcatcatga tgatttcctc gcagtcgatt    480
gtggctgagg ttgtctccgc acgtgagcgc ggcaagttca tgggtattat gggcggcgtc    540
tttggcgtct cctccgtact gggtccagtt ctcggtggct ggttcaccga tggtcccggt    600
tggcgttggg gcctgtggat caacattcca ctgggtctgc tggcaattat tgtctgcgct    660
ttcgtactga agctgcgcgt gggcgagcaa ggctttaagg gctttgactg gatgggtttt    720
gcggccgtcg caatcacgac cagcaccctg atctgctcca ccacttgggg cggaagcgaa    780
tacgagtgga cttccccaac tatttttgtc atggctgccg tagtcatcgt cggcgcgctg    840
ctcaccgtgt tcattgagtc gcgtgcatcc cagccgctga tcccggttca gctatttaag    900
aaccgcaaca tggttttgac caccctcgcc ggtactgttt tgggtctggc catgatgggc    960
gtgctcggct acatgccaac ctacctgcag atggtgcaca ccctgacgcc aactgaagca   1020
ggcttgatga tgatcccgat gatggtcggc atgatcggtg tctccactgg tgttggcttc   1080
atcatcgcta agaccggcaa ctacaagtac taccccatcg cgggcctggc catcacggcg   1140
tttgctttgt ggtggatgac ccagatgacc gttgagactt cattgaccgg tatcggagtt   1200
cgcttccttg tattcggtgt cggcttgggc tttgtcacgc aggtactggt gctgattgtt   1260
caaaactcct ccctgtatc gcaggtcggt actgccacgg cggctaataa cttcttccgc    1320
cagattggtt cggcattggg tgcttccatc gtgggttcga tgttcattca caaaatgcag   1380
aatgagatgg ctaccgtttt gcctgatgcc cttgcatcgt tgggcaagga aggcgccgct   1440
atttcgcagc agttccaagg tgcagatgcc gccaactcct tgactccgca cgcagtcgca   1500
gagcttcccg atgtcctccg tgacgctatc ttaaattcct acaatgacgg tctgaccccc   1560
gtgattggca tgatggtgcc actggccatt gttgcaatgc tgattttgtt cccactgcgc   1620
caagagcgct tgaaggaaac catcgaataa                                    1650

SEQ ID NO: 121         moltype = AA  length = 549
FEATURE                Location/Qualifiers
REGION                 1..549
                       note = impE2(G64D, S387T, F405Y, M413T, N458K)
source                 1..549
                       mol_type = protein
                       organism = unidentified
SEQUENCE: 121
```

```
MVAKNSTPST AGHASAHTAE EFPVANAEMA TPSAIDPNHG KKTADNVGII FAALMLTMLM   60
SSLDQMIFGS ALPTIVGELG GVDQMSWVIS AFMVTMTIAM PLAGQLGDRM GRKWVYISGI  120
SIFVIGSTLG GFANGMGMLI TGRAIQGFGA GIMMISSQSI VAEVVSARER GKFMGIMGGV  180
FGVSSVLGPV LGGWFTDGPG WRWGLWINIP LGLLAIIVCA FVLKLRVGEQ GFKGFDWMGF  240
AAIAITTSTL ILLTTWGGSE YEWTSPTILS MAAVVIVGAL LTVFIESRAS QPLIPVQLFK  300
NRNMVLTTLA GTVLGLAMMG VLGYMPTYLQ MVHTLTPTEA GLMMIPMMVG MIGVSTGVGF  360
IIAKTGNYKY YPIAGLAITA FALWWMTQMT VETSLTGIGV RFLVYGVGLG FVTQVLVLIV  420
QNSFPVSQVG TATAANNFFR QIGSALGASI VGSMFIHKMQ NEMATRLPDA LASLGKEGAA  480
ISQQFQGADA ANSLTPHAVA ELPDVLRDAI LNSYNDGLTP VIGMMVPLAI VAMLILFPLR  540
QERLKETIE                                                         549

SEQ ID NO: 122          moltype = DNA  length = 1650
FEATURE                 Location/Qualifiers
misc_feature            1..1650
                        note = impE2(G64D, S387T, F405Y, M413T, N458K)
source                  1..1650
                        mol_type = other DNA
                        organism = unidentified
SEQUENCE: 122
atggtagcta aaaactccac cccaagcacg gccggccacg ccagtgctca cactgcggaa    60
gaattcccag tggccaatgc tgaaatggca acgccttcag caatcgaccc aaaccacggt   120
aaaaagaccg cggataacgt cggcattatc ttcgctgcct tgatgctcac catgctgatg   180
agctctttgg accagatgat tttcggttcc gctctgccaa ccatcgtcgg cgagctcggc   240
ggcgtggacc agatgagctg ggtaattttca gcatttatgg tcaccatgac cattgctatg   300
ccactagccg gtcagctcgg tgaccgcatg gccgcaagtg gggtctacat ctcaggtatc   360
tccatttttcg ttattggctc gacgctcggt gctttgcaa atggcatggg catgctgatc   420
accggacgtg caatccaggg cttcggtgcc ggcatcatga tgatttcctc gcagtcgatt   480
gtggctgagg ttgtctccgc acgtgagcgc ggcaagttca tgggtattat gggcggcgtc   540
tttggcgtct cctccgtact gggtccagtt ctcggtggct ggttcaccga tggtcccggt   600
tggcgttggg gcctgtggat caacattcca ctgggtctgc tggcaattat tgtctgcgct   660
ttcgtactga agctgcgcgt gggcgagcaa ggctttaagg gctttgactg gatgggtttt   720
gcggccatcg caatcacgac cagcaccctg attctgctca ccacttgggg cggaagcgaa   780
tacgagtgga cttccccaac tattttgtcc atggctgccg tagtcatcgt cggcgcgctg   840
ctcaccgtgt tcattgagtc gcgtgcatcc cagccgctga tcccggttca gctatttaag   900
aaccgcaaca tggttttgac caccctcgcc ggtactgttt tgggtctggc catgatgggc   960
gtgctcggct acatgccaac ctacctgcag atggtgcaca ccctgacgcc aactgaagca  1020
ggcttgatga tgatcccgat gatggtcggc atgatcggtg tctccactgg tgttggcttc  1080
atcatcgcta agaccggcaa ctacaagtac taccccatcg cgggcctggc catcacgcg   1140
tttttgtttg gtggatgac ccagatgacc gttgagctt cattgaccgg tatcggagtt  1200
cgcttccttg tatacggtgt cggcttggc tttgtcacgc aggtactggt gctgattgtt  1260
caaaactcct ccctgtatc gcaggtcggt actgccacgg cggctaataa cttcttccgc  1320
cagattggtt cggcattggg tgcttccatc gtgggttcga tgttcattca aaaatgcag  1380
aatgagatgg ctacccgttt gcctgatgcc cttgcatcgt tgggcaagga aggcgccgct  1440
atttcgcagc agttccaagg tgcagatgcc gccaactcct tgactccgca cgcagtcgca  1500
gagcttcccg atgtcctccg tgacgctatc ttaaattcct acaatgacgg tctgacccc   1560
gtgattggca tgatggtgcc actggccatt gttgcaatgc tgattttgtt cccactgcgc  1620
caagagcgct tgaaggaaac catcgaataa                                   1650

SEQ ID NO: 123          moltype = AA  length = 549
FEATURE                 Location/Qualifiers
REGION                  1..549
                        note = impE2(G64D, F123C, S387T, M413T, N458K)
source                  1..549
                        mol_type = protein
                        organism = unidentified
SEQUENCE: 123
MVAKNSTPST AGHASAHTAE EFPVANAEMA TPSAIDPNHG KKTADNVGII FAALMLTMLM   60
SSLDQMIFGS ALPTIVGELG GVDQMSWVIS AFMVTMTIAM PLAGQLGDRM GRKWVYISGI  120
SICVIGSTLG GFANGMGMLI TGRAIQGFGA GIMMISSQSI VAEVVSARER GKFMGIMGGV  180
FGVSSVLGPV LGGWFTDGPG WRWGLWINIP LGLLAIIVCA FVLKLRVGEQ GFKGFDWMGF  240
AAIAITTSTL ILLTTWGGSE YEWTSPTILS MAAVVIVGAL LTVFIESRAS QPLIPVQLFK  300
NRNMVLTTLA GTVLGLAMMG VLGYMPTYLQ MVHTLTPTEA GLMMIPMMVG MIGVSTGVGF  360
IIAKTGNYKY YPIAGLAITA FALWWMTQMT VETSLTGIGV RFLVFGVGLG FVTQVLVLIV  420
QNSFPVSQVG TATAANNFFR QIGSALGASI VGSMFIHKMQ NEMATRLPDA LASLGKEGAA  480
ISQQFQGADA ANSLTPHAVA ELPDVLRDAI LNSYNDGLTP VIGMMVPLAI VAMLILFPLR  540
QERLKETIE                                                         549

SEQ ID NO: 124          moltype = DNA  length = 1650
FEATURE                 Location/Qualifiers
misc_feature            1..1650
                        note = impE2(G64D, F123C, S387T, M413T, N458K)
source                  1..1650
                        mol_type = other DNA
                        organism = unidentified
SEQUENCE: 124
atggtagcta aaaactccac cccaagcacg gccggccacg ccagtgctca cactgcggaa    60
gaattcccag tggccaatgc tgaaatggca acgccttcag caatcgaccc aaaccacggt   120
aaaaagaccg cggataacgt cggcattatc ttcgctgcct tgatgctcac catgctgatg   180
agctctttgg accagatgat tttcggttcc gctctgccaa ccatcgtcgg cgagctcggc   240
```

-continued

```
ggcgtggacc agatgagctg ggtaatttca gcatttatgg tcaccatgac cattgctatg  300
ccactagccg gtcagctcgg tgaccgcatg ggccgcaagt gggtctacat ctcaggtatc  360
tccatttgcg ttattggctc gacgctcggt ggctttgcca atggcatggg catgctgatc  420
accggacgtg caatccaggg cttcggtgcc ggcatcatga tgatttcctc gcagtcgatt  480
gtggctgagg ttgtctccgc acgtgagcgc ggcaagttca tgggtattat gggcggcgtc  540
tttggcgtct cctccgtact gggtccagtt ctcggtggct ggttcaccga tggtcccggt  600
tggcgttggg gcctgtggat caacattcca ctgggtctgc tggcaattat tgtctgcgct  660
ttcgtactga agctgcgcgt gggcgagcaa ggctttaagg gctttgactg gatgggtttt  720
gcggccgtcg caatcacgac cagcaccctg attctgctca ccacttgggg cggaagcgaa  780
tacgagtgga cttccccaac tattttgtcc atggctgccg tagtcatcgt cggcgcgctg  840
ctcaccgtgt tcattgagtc gcgtgcatcc cagccgctga tcccggttca gctatttaag  900
aaccgcaaca tggttttgac caccctcgcc ggtactgttt gggtctggc catgatgggc  960
gtgctcggct acatgccaac ctacctgcag atggtgcaca ccctgacgcc aactgaagca 1020
ggcttgatga tgatcccgat gatggtcggc atgatcggtg tctccactgg tgttggcttc 1080
atcatcgcta agaccggcaa ctacaagtac taccccatcg cgggcctggc catcacggcg 1140
tttgctttgt ggtggatgac ccagatgacc gttgagactt cattgaccgg tatcggagtt 1200
cgcttccttg tattcggtgt cggcttgggc tttgtcacgc aggtactggt gctgattgtt 1260
caaaactcct tccctgtatc gcaggtcggt actgccacgg cggctaataa cttcttccgc 1320
cagattggtt cggcattggg tgcttccatc gtgggttcga tgttcattca caaaatgcag 1380
aatgagatgg ctaccgtttt gcctgatgcc cttgcatcgt tgggcaagga aggcgccgct 1440
atttcgcagc agttccaagg tgcagatgcc gccaactcct tgactccgca cgcagtcgca 1500
gagcttcccg atgtcctccg tgacgctatc ttaaattcct acaatgacgg tctgacccc  1560
gtgattggca tgatggtgcc actggccatt gttgcaatgc tgatttttgtt cccactgcgc 1620
caagagcgct tgaaggaaac catcgaataa                                   1650
```

```
SEQ ID NO: 125         moltype = AA   length = 549
FEATURE                Location/Qualifiers
REGION                 1..549
                       note = impE2(G64D, I243V, S387T, F405Y, M413T, N458K)
source                 1..549
                       mol_type = protein
                       organism = unidentified
SEQUENCE: 125
MVAKNSTPST AGHASAHTAE EFPVANAEMA TPSAIDPNHG KKTADNVGII FAALMLTMLM  60
SSLDQMIFGS ALPTIVGELG GVDQMSWVIS AFMVTMTIAM PLAGQLGDRM GRKWVYISGI 120
SIFVIGSTLG GFANGMGMLI TGRAIQGFGA GIMMISSQSI VAEVVSARER GKFMGIMGGV 180
FGVSSVLGPV LGGWFTDGPG WRWGLWINIP LGLLAIIVCA FVLKLRVGEQ GFKGFDWMGF 240
AAVAITTSTL ILLTTWGGSE YEWTSPTILS MAAVVIVGAL LTVFIESRAS QPLIPVQLFK 300
NRNMVLTTLA GTVLGLAMMG VLGYMPTYLQ MVHTLTPTEA GLMMIPMMVG MIGVSTGVGF 360
IIAKTGNYKY YPIAGLAITA FALWWMTQMT VETSLTGIGV RFLVYGVGLG FVTQVLVLIV 420
QNSFPVSQVG TATAANNFFR QIGSALGASI VGSMFIHKMQ NEMATRLPDA LASLGKEGAA 480
ISQQFQGADA ANSLTPHAVA ELPDVLRDAI LNSYNDGLTP VIGMMVPLAI VAMLILFPLR 540
QERLKETIE                                                         549
```

```
SEQ ID NO: 126         moltype = DNA   length = 1650
FEATURE                Location/Qualifiers
misc_feature           1..1650
                       note = impE2(G64D, I243V, S387T, F405Y, M413T, N458K)
source                 1..1650
                       mol_type = other DNA
                       organism = unidentified
SEQUENCE: 126
atggtagcta aaaactccac cccaagcacg gccggccacg ccagtgctca cactgcggaa   60
gaattcccag tggccaatgc tgaaatggca acgcctcag caatcgaccc aaaccacggt  120
aaaaagaccg cggataacgt cggcattatc ttcgctgctc tgatgctcac catgctgatg  180
agctctttgg accagatgat tttcggttcc gctctgccaa ccatcgtcgg cgagctcggc  240
ggcgtggacc agatgagctg ggtaatttca gcatttatgg tcaccatgac cattgctatg  300
ccactagccg gtcagctcgg tgaccgcatg ggccgcaagt gggtctacat ctcaggtatc  360
tccattttcg ttattggctc gacgctcggt ggctttgcca atggcatggg catgctgatc  420
accggacgtg caatccaggg cttcggtgcc ggcatcatga tgatttcctc gcagtcgatt  480
gtggctgagg ttgtctccgc acgtgagcgc ggcaagttca tgggtattat gggcggcgtc  540
tttggcgtct cctccgtact gggtccagtt ctcggtggct ggttcaccga tggtcccggt  600
tggcgttggg gcctgtggat caacattcca ctgggtctgc tggcaattat tgtctgcgct  660
ttcgtactga agctgcgcgt gggcgagcaa ggctttaagg gctttgactg gatgggtttt  720
gcggccgtcg caatcacgac cagcaccctg attctgctca ccacttgggg cggaagcgaa  780
tacgagtgga cttccccaac tattttgtcc atggctgccg tagtcatcgt cggcgcgctg  840
ctcaccgtgt tcattgagtc gcgtgcatcc cagccgctga tcccggttca gctatttaag  900
aaccgcaaca tggttttgac caccctcgcc ggtactgttt gggtctggc catgatgggc  960
gtgctcggct acatgccaac ctacctgcag atggtgcaca ccctgacgcc aactgaagca 1020
ggcttgatga tgatcccgat gatggtcggc atgatcggtg tctccactgg tgttggcttc 1080
atcatcgcta agaccggcaa ctacaagtac taccccatcg cgggcctggc catcacggcg 1140
tttgctttgt ggtggatgac ccagatgacc gttgagactt cattgaccgg tatcggagtt 1200
cgcttccttg tatcggtgt cggcttgggc tttgtcacgc aggtactggt gctgattgtt 1260
caaaactcct tccctgtatc gcaggtcggt actgccacgg cggctaataa cttcttccgc 1320
cagattggtt cggcattggg tgcttccatc gtgggttcga tgttcattca caaaatgcag 1380
aatgagatgg ctaccgtttt gcctgatgcc cttgcatcgt tgggcaagga aggcgccgct 1440
atttcgcagc agttccaagg tgcagatgcc gccaactcct tgactccgca cgcagtcgca 1500
gagcttcccg atgtcctccg tgacgctatc ttaaattcct acaatgacgg tctgacccc  1560
gtgattggca tgatggtgcc actggccatt gttgcaatgc tgatttttgtt cccactgcgc 1620
```

```
caagagcgct tgaaggaaac catcgaataa                                        1650

SEQ ID NO: 127          moltype = AA  length = 549
FEATURE                 Location/Qualifiers
REGION                  1..549
                        note = impE2(G64D, F123C, I243V, S387T, F405Y, M413T, N458K)
source                  1..549
                        mol_type = protein
                        organism = unidentified
SEQUENCE: 127
MVAKNSTPST AGHASAHTAE EFPVANAEMA TPSAIDPNHG KKTADNVGII FAALMLTMLM    60
SSLDQMIFGS ALPTIVGELG GVDQMSWVIS AFMVTMTIAM PLAGQLGDRM GRKWVYISGI    120
SICVIGSTLG GFANGMGMLI TGRAIQGFGA GIMMISSQSI VAEVVSARER GKFMGIMGGV    180
FGVSSVLGPV LGGWFTDGPG WRWGLWINIP LGLLAIIVCA FVLKLRVGEQ GFKGFDWMGF    240
AAVAITTSTL ILLTTWGGSE YEWTSPTILS MAAVVIVGAL LTVFIESRAS QPLIPVQLFK    300
NRNMVLTTLA GTVLGLAMMG VLGYMPTYLQ MVHTLTPTEA GLMMIPMMVG MIGVSTGVGF    360
IIAKTGNYKY YPIAGLAITA FALWWMTQMT VETSLTGIGV RFLVYGVGLG FVTQVLVLIV    420
QNSFPVSQVG TATAANNFFR QIGSALGASI VGSMFIHKMQ NEMATRLPDA LASLGKEGAA    480
ISQQFQGADA ANSLTPHAVA ELPDVLRDAI LNSYNDGLTP VIGMMVPLAI VAMLILFPLR    540
QERLKETIE                                                            549

SEQ ID NO: 128          moltype = DNA  length = 1650
FEATURE                 Location/Qualifiers
misc_feature            1..1650
                        note = impE2(G64D, F123C, I243V, S387T, F405Y, M413T, N458K)
source                  1..1650
                        mol_type = other DNA
                        organism = unidentified
SEQUENCE: 128
atggtagcta aaaactccac cccaagcacg gccggccacg ccagtgctca cactgcggaa    60
gaattcccag tggccaatgc tgaaatggca acgccttcag caatcgaccc aaaccacggt    120
aaaaagaccg cggataacgt cggcattatc ttcgctgcct tgatgctcac catgctgatg    180
agctctttgg accagatgat tttcggttcc gctctgccaa ccatcgtcgg cgagctcggc    240
ggcgtggacc agatgagctg ggtaatttca gcatttatgg tcaccatgac cattgctatg    300
ccactagccg gtcagctcgg tgaccgcatg ggccgcaagt gggtctacat ctcaggtatc    360
tccatttgcg ttattggctc gacgctcggc ggctttgcca atggcatggg catgctgatc    420
accggacgtg caatccaggg cttcggtgcc ggcatcatga tgatttcctc gcagtcgatt    480
gtggctgagg ttgtctccgc acgtgagcgc ggcaagttca tgggtattat gggcggcgtc    540
tttggcgtct cctccgtact gggtccagtt ctcggtggct ggttcaccga tgggcccggt    600
tggcgttggg gcctgtggat caacattcca ctgggtctgc tggcaattat tgtctgcgct    660
ttcgtactga agctgcgcgt gggcgagcaa ggctttaagg gctttgactg gatgggttt    720
gcggccgtcg caatcacgac cagcaccctg attctgctca ccacttgggg cggaagcgaa    780
tacgagtgga cttccccaac tatttttgtcc atggctgccg tagtcatcgt cggcgcgttg    840
ctcaccgtgt tcattgagtc gcgtgcatcc cagccgctga tcccggttca gctatttaag    900
aaccgcaaca tggttttgac caccctcgcc ggtactgttt tgggtctggc catgatgggc    960
gtgctcggct acatgccaac ctacctgcag atggtgcaca ccctgacgcc aactgaagca    1020
ggcttgatga tgatcccgat gatgtcggc atgatcggta tctccactgg tgttggcttc    1080
atcatcgcta agaccggcaa ctacaagtac taccccatcg cgggcctggc catcacggcg    1140
tttgcttttg ggtggatgac ccagatgacc gttgagactt cattgaccgg tatcggagtt    1200
cgcttccttg tatacggtgt cggcttgggc tttgtcacgc aggtactggt gctgattgtt    1260
caaaactcct ccctgtatc gcaggtcggt actgccacgc taataacttc ttccgc      1320
cagattggtt cggcattggg tgcttccatc gtgggttcga tgttcattca caaatgcag    1380
aatgagatgg ctacccgttt gcctgatgcc cttgcatcgt tgggcaagga aggcgccgct    1440
atttcgcagc agttccaagg tgcagatgcc gccaactcct tgactccgca cgcagtgcga    1500
gagcttcccg atgtcctccg tgacgctatc ttaaattcct acaatgacgg tctgacccc    1560
gtgattggca tgatggtgcc actgccatt gttgcaatgc tgattttgtt cccactgcgc    1620
caagagcgct tgaaggaaac catcgaataa                                    1650

SEQ ID NO: 129          moltype = AA  length = 549
FEATURE                 Location/Qualifiers
REGION                  1..549
                        note = CJI0323 impE2(S387T, M413T, N458K)
source                  1..549
                        mol_type = protein
                        organism = unidentified
SEQUENCE: 129
MIAKNSTPST AGHASAHTAE EFPVANAEMA TPSAIDPNHG KKTADNVGII FAALMLTMLM    60
SSLGQMIFGS ALPTIVGELG GVDQMSWVIS AFMVTMTIAM PLAGQLGDRM GRKWVYISGI    120
SIFVIGSTLG GFANGMGMLI TGRAIQGFGA GIMMISSQSI VAEVVSARER GKFMGIMGGV    180
FGVSSVLGPV LGGWFTDGPG WRWGLWINIP LGLLAIIVCA FVLKLRVGEQ GFKGFDWMGF    240
AAIAITTSTL ILLTTWGGSE YEWTSPTILS MAAVVIVGAL LTVFIESRAS QPLIPVQLFK    300
NRNMVLTTLA GTVLGLAMMG VLGYMPTYLQ MVHTLTPTEA GLMMIPMMVG MIGVSTGVGF    360
IIAKTGNYKY YPIAGLAITA FALWWMTQMT VETSLTGIGV RFLVFGVGLG FVTQVLVLIV    420
QNSFPVSQVG TATAANNFFR QIGSALGASI VGSMFIHKMQ NEMATRLPDA LASLGKEGAA    480
ISQQFQGADA ANSLTPHAVA ELPDVLRDAI LNSYNDGLTP VIGMMVPLAI VAMLILFPLR    540
QERLKETIE                                                            549

SEQ ID NO: 130          moltype = DNA  length = 1650
FEATURE                 Location/Qualifiers
```

```
misc_feature            1..1650
                        note = CJI0323 impE2(S387T, M413T, N458K)
source                  1..1650
                        mol_type = other DNA
                        organism = unidentified
SEQUENCE: 130
atgatagcta aaaactccac cccaagcacg gccggccacg ccagtgctca cactgcggaa    60
gaattcccag tggccaatgc tgaaatggca acgccttcag caatcgaccc aaaccacggt   120
aaaaagaccg cggataacgt cggcattatc ttcgctgcct tgatgctcac catgctgatg   180
agctctttgg ggcagatgat tttcggttcc gctctgccaa ccatcgtcgg cgagctcggc   240
ggcgtggacc agatgagctg ggtaatttca gcatttatgg tcaccatgac cattgctatg   300
ccactagccg gtcagctcgg tgaccgcatg ggccgcaagt gggtctacat ctcaggtatc   360
tccatttttcg ttattggctc gacgctcggt ggctttgcca atggcatggg catgctgatc   420
accggacgtg caatccaggg cttcggtgcc ggcatcatga tgatttcctc gcagtcgatt   480
gtggctgagg ttgtctccgc acgtgagcgc ggcaagttca tgggtattat gggcggcgtc   540
tttggcgtct cctccgtact gggtccagtt ctcggtggct ggttcaccga tggtcccggt   600
tggcgttggg gcctgtggat caacattcca ctgggtctgc tggcaattat tgtctgcgct   660
ttcgtactga agctcgcgcgt gggcgagcaa ggctttaagg gctttgactg gatgggtttt   720
gcggccatcg caatcacgac cagcaccctg attctgctca ccacttgggg cggaagcgaa   780
tacgagtgga cttccccaac tattttgtcc atggctgccg tagtcatcgt cggcgcgctg   840
ctcaccgtgt tcattgagtc gcgtgcatcc cagccgctga tcccggttca gctatttaag   900
aaccgcaaca tggttttgac caccctcgcc ggtactgttt tgggtctggc catgatgggc   960
gtgctcggct acatgccaac ctacctgcag atggtgcaca ccctgacgcc aactgaagca  1020
ggcttgatga tgatcccgat gatggtcggc atgatcggtg tctccactgg tgttggcttc  1080
atcatcgcta agaccggcaa ctacaagtac taccccatcg cgggcctggc catcacggcg  1140
tttgcttttgt ggtggatgac ccagatgacc gttgagactt cattgaccgg tatcgaagtt  1200
cgcttccttg tattcggtgt cggcttgggc tttgtcacgc aggtactggt gctgattgtt  1260
caaaactcct tccctgtatc gcaggtcggt actgccacgg cggctaataa cttcttccgc  1320
cagattggtt cggcattggg tgcttccatc gtgggttcga tgttcattca aaaatgcag   1380
aatgagatgg ctacccgttt gcctgatgcc cttgcatcgt tgggcaagga aggcgccgct  1440
atttcgcagc agttccaagg tgcagatgcc gccaactcct tgactccgca cgcagtcgca  1500
gagcttcccg atgtcctccg tgacgctatc ttaaattcct acaatgacgg tctgacccc   1560
gtgattggca tgatggtgcc actggccatt gttgcaatgc tgattttgtt cccactgcgc  1620
caagagcgct tgaaggaaac catcgaataa                                    1650

SEQ ID NO: 131          moltype = AA  length = 549
FEATURE                 Location/Qualifiers
REGION                  1..549
                        note = CJI0323 impE2(G64D, S387T, M413T, N458K)
source                  1..549
                        mol_type = protein
                        organism = unidentified
SEQUENCE: 131
MIAKNSTPST AGHASAHTAE EFPVANAEMA TPSAIDPNHG KKTADNVGII FAALMLTMLM    60
SSLDQMIFGS ALPTIVGELG GVDQMSWVIS AFMVTMTIAM PLAGQLGDRM GRKWVYISGI   120
SIFVIGSTLG GFANGMGMLI TGRAIQGFGA GIMMISSQSI VAEVVSARER GKFMGIMGGV   180
FGVSSVLGPV LGGWFTDGPG WRWGLWINIP LGLLAIIVCA FVLKLRVGEQ GFKGFDWMGF   240
AAIAITTSTL ILLTTWGGSE YEWTSPTILS MAAVVIVGAL LTVFIESRAS QPLIPVQLFK   300
NRNMVLTTLA GTVLGLAMMG VLGYMPTYLQ MVHTLTPTEA GLMMIPMMVG MIGVSTGVGF   360
IIAKTGNYKY YPIAGLAITA FALWWMTQMT VETSLTGIGV RFLVFGVGLG FVTQVLVLIV   420
QNSFPVSQVG TATAANNFFR QIGSALGASI VGSMFIHKMQ NEMATRLPDA LASLGKEGAA   480
ISQQFQGADA ANSLTPHAVA ELPDVLRDAI LNSYNDGLTP VIGMMVPLAI VAMLILFPLR   540
QERLKETIE                                                           549

SEQ ID NO: 132          moltype = DNA  length = 1650
FEATURE                 Location/Qualifiers
misc_feature            1..1650
                        note = CJI0323 impE2(G64D, S387T, M413T, N458K)
source                  1..1650
                        mol_type = other DNA
                        organism = unidentified
SEQUENCE: 132
atgatagcta aaaactccac cccaagcacg gccggccacg ccagtgctca cactgcggaa    60
gaattcccag tggccaatgc tgaaatggca acgccttcag caatcgaccc aaaccacggt   120
aaaaagaccg cggataacgt cggcattatc ttcgctgcct tgatgctcac catgctgatg   180
agctctttgg accagatgat tttcggttcc gctctgccaa ccatcgtcgg cgagctcggc   240
ggcgtggacc agatgagctg ggtaatttca gcatttatgg tcaccatgac cattgctatg   300
ccactagccg gtcagctcgg tgaccgcatg ggccgcaagt gggtctacat ctcaggtatc   360
tccatttttcg ttattggctc gacgctcggt ggctttgcca atggcatggg catgctgatc   420
accggacgtg caatccaggg cttcggtgcc ggcatcatga tgatttcctc gcagtcgatt   480
gtggctgagg ttgtctccgc acgtgagcgc ggcaagttca tgggtattat gggcggcgtc   540
tttggcgtct cctccgtact gggtccagtt ctcggtggct ggttcaccga tggtcccggt   600
tggcgttggg gcctgtggat caacattcca ctgggtctgc tggcaattat tgtctgcgct   660
ttcgtactga agctcgcgcgt gggcgagcaa ggctttaagg gctttgactg gatgggtttt   720
gcggccatcg caatcacgac cagcaccctg attctgctca ccacttgggg cggaagcgaa   780
tacgagtgga cttccccaac tattttgtcc atggctgccg tagtcatcgt cggcgcgctg   840
ctcaccgtgt tcattgagtc gcgtgcatcc cagccgctga tcccggttca gctatttaag   900
aaccgcaaca tggttttgac caccctcgcc ggtactgttt tgggtctggc catgatgggc   960
gtgctcggct acatgccaac ctacctgcag atggtgcaca ccctgacgcc aactgaagca  1020
```

```
ggcttgatga tgatcccgat gatggtcggc atgatcggtg tctccactgg tgttggcttc    1080
atcatcgcta agaccggcaa ctacaagtac taccccatcg cgggcctggc catcacggcg    1140
tttgctttgt ggtggatgac ccagatgacc gttgagactt cattgaccgg tatcggagtt    1200
cgcttccttg tattcggtgt cggcttgggc tttgtcacgc aggtactggt gctgattgtt    1260
caaaactcct tccctgtatc gcaggtcggt actgccacgg cggctaataa cttcttccgc    1320
cagattggtt cggcattggg tgcttccatc gtgggttcga tgttcattca aaatatgcag    1380
aatgagatgg ctacccgttt gcctgatgcc cttgcatcgt gggcaagga aggcgccgct    1440
atttcgcagc agttccaagg tgcagatgcc gccaactcct tgactccgca cgcagtcgca    1500
gagcttcccg atgtcctccg tgacgctatc ttaaattcct acaatgacgg tctgacccc    1560
gtgattggca tgatggtgcc actggccatt gttgcaatgc tgatttttgtt cccactgcgc    1620
caagagcgct tgaaggaaac catcgaataa                                     1650

SEQ ID NO: 133           moltype = AA   length = 549
FEATURE                  Location/Qualifiers
REGION                   1..549
                         note = CJI0323 impE2(G64D, F123C)
source                   1..549
                         mol_type = protein
                         organism = unidentified
SEQUENCE: 133
MIAKNSTPST AGHASAHTAE EFPVANAEMA TPSAIDPNHG KKTADNVGII FAALMLTMLM     60
SSLDQMIFGS ALPTIVGELG GVDQMSWVIS AFMVTMTIAM PLAGQLGDRM GRKWVYISGI    120
SICVIGSTLG GFANGMGMLI TGRAIQGFGA GIMMISSQSI VAEVVSARER GKFMGIMGGV    180
FGVSSVLGPV LGGWFTDGPG WRWGLWINIP LGLLAIIVCA FVLKLRVGEQ GFKGFDWMGF    240
AAIAITTSTL ILLTTWGGSE YEWTSPTILS MAAVVIVGAL LTVFIESRAS QPLIPVQLFK    300
NRNMVLTTLA GTVLGLAMMG VLGYMPTYLQ MVHTLTPTEA GLMMIPMMVG MIGVSTGVGF    360
IIAKTGNYKY YPIAGLAITA FALWWMSQMT VETSLTGIGV RFLVFGVGLG FVMQVLVLIV    420
QNSFPVSQVG TATAANNFFR QIGSALGASI VGSMFIHNMQ NEMATRLPDA LASLGKEGAA    480
ISQQFQGADA ANSLTPHAVA ELPDVLRDAI LNSYNDGLTP VIGMMVPLAI VAMLILFPLR    540
QERLKETIE                                                            549

SEQ ID NO: 134           moltype = DNA   length = 1650
FEATURE                  Location/Qualifiers
misc_feature             1..1650
                         note = CJI0323 impE2(G64D, F123C)
source                   1..1650
                         mol_type = other DNA
                         organism = unidentified
SEQUENCE: 134
atgatagcta aaaactccac cccaagcacg gccggccacg ccagtgctca cactgcggaa      60
gaattcccag tggccaatgc tgaaatggca acgccttcag caatcgaccc aaaccacggt    120
aaaaagaccg cggataacgt cggcattatc ttcgctgcct tgatgctcac catgctgatg    180
agctctttgg accagatgat tttcggttcc gctctcccga tcgtcggcga gctgggc       240
ggcgtggacc agatgagctg ggtaatttca gcatttatgg tcaccatgac cattgctatg    300
ccactagccg gtcagctcgg tgaccgcatg gccgcaagtg gggtctacat ctcaggtatc    360
tccatttgcg ttattggctc gacgctcggt ggctttgcca atggcatggg catgctgatc    420
accggacgtg caatccaggg cttcggtgcc ggcatcatga tgatttcctc gcagtcgatt    480
gtggctgagg ttgtctccgc acgtgagcgc ggcaagttca tgggtattat gggcggcgtc    540
tttggcgtct cctccgtact gggtccagtt ctcggtggct ggttcaccga tggtcccggt    600
tggcgttggg gcctgtggat caacattcca ctgggtctgc tggcaattat tgtctgcgct    660
ttcgtactga agctgcgcgt gggcgagcaa ggctttaagg gctttgactg gatgggtttt    720
gcggccatcg caatcacgac cagcaccctg attctgctca ccacttgggg cggaagcgaa    780
tacgagtgga cttccccaac tattttgtcc atggctgccg tagtcatcgt cggcgcgctg    840
ctcaccgtgt tcattgagtc gcgtgcatcc cagccgctga tccgggttca gctatttaag    900
aaccgcaaca tggttttgac caccctcgcg ggtactgttt tgggtctggc catgatgggc    960
gtgctcggct acatgccaac ctacctgcag atggtgcaca ccctgacgcc aactgaagca   1020
ggcttgatga tgatcccgat gatggtcggc atgatcggtg tctccactgg tgttggcttc   1080
atcatcgcta agaccggcaa ctacaagtac taccccatcg cgggcctggc catcacggcg   1140
tttgctttgt ggtggatgtc ccagatgacc gttgagactt cattgaccgg tatcggagtt   1200
cgcttccttg tattcggtgt cggcttgggc tttgtcatgc aggtactggt gctgattgtt   1260
caaaactcct tccctgtatc gcaggtcggt actgccacgg cggctaataa cttcttccgc   1320
cagattggtt cggcattggg tgcttccatc gtgggttcga tgttcattca atatgcag    1380
aatgagatgg ctacccgttt gcctgatgcc cttgcatcgt gggcaagga aggcgccgct    1440
atttcgcagc agttccaagg tgcagatgcc gccaactcct tgactccgca cgcagtcgca   1500
gagcttcccg atgtcctccg tgacgctatc ttaaattcct acaatgacgg tctgacccc   1560
gtgattggca tgatggtgcc actggccatt gttgcaatgc tgatttttgtt cccactgcgc  1620
caagagcgct tgaaggaaac catcgaataa                                    1650

SEQ ID NO: 135           moltype = AA   length = 549
FEATURE                  Location/Qualifiers
REGION                   1..549
                         note = CJI0323 impE2(G64D, I243V)
source                   1..549
                         mol_type = protein
                         organism = unidentified
SEQUENCE: 135
MIAKNSTPST AGHASAHTAE EFPVANAEMA TPSAIDPNHG KKTADNVGII FAALMLTMLM     60
SSLDQMIFGS ALPTIVGELG GVDQMSWVIS AFMVTMTIAM PLAGQLGDRM GRKWVYISGI    120
SIFVIGSTLG GFANGMGMLI TGRAIQGFGA GIMMISSQSI VAEVVSARER GKFMGIMGGV    180
```

```
FGVSSVLGPV LGGWFTDGPG WRWGLWINIP LGLLAIIVCA FVLKLRVGEQ GFKGFDWMGF 240
AAVAITTSTL ILLTTWGGSE YEWTSPTILS MAAVVIVGAL LTVFIESRAS QPLIPVQLFK 300
NRNMVLTTLA GTVLGLAMMG VLGYMPTYLQ MVHTLTPTEA GLMMIPMMVG MIGVSTGVGF 360
IIAKTGNYKY YPIAGLAITA FALWWMSQMT VETSLTGIGV RFLVFGVGLG FVMQVLVLIV 420
QNSFPVSQVG TATAANNFFR QIGSALGASI VGSMFIHNMQ NEMATRLPDA LASLGKEGAA 480
ISQQFQGADA ANSLTPHAVA ELPDVLRDAI LNSYNDGLTP VIGMMVPLAI VAMLILFPLR 540
QERLKETIE                                                         549

SEQ ID NO: 136          moltype = DNA   length = 1650
FEATURE                 Location/Qualifiers
misc_feature            1..1650
                        note = CJI0323 impE2(G64D, I243V)
source                  1..1650
                        mol_type = other DNA
                        organism = unidentified
SEQUENCE: 136
atgatagcta aaaactccac cccaagcacg gccggccacg ccagtgctca cactgcggaa   60
gaattcccag tggccaatgc tgaaatggca acgccttcag caatcgaccc aaaccacggt  120
aaaaagaccg cggataacgt cggcattatc ttcgctgcct tgatgctcac catgctgatg  180
agctctttgg accagatgat tttcggttcc gctctgccaa ccatcgtcgg cgagctcggc  240
ggcgtggacc agatgagctg ggtaatttca gcatttatgg tcaccatgac cattgctatg  300
ccactagccg gtcagctcgg tgaccgcatg ggccgcaagt gggtctacat ctcaggtatc  360
tccattttcg ttattggctc gacgctcggt ggctttgcca atggcatggg catgctgatc  420
accggacgtg caatccaggg cttcggtgcc ggcatcatga tgatttcctc gcagtcgatt  480
gtggctgagg ttgtctccgc acgtgagcgc ggcaagttca tgggtattat gggcggcgtc  540
tttggcgtct cctccgtact gggtccagtt tcggtggcgg ttcaccgag tggtcccggt  600
tggcgttggg gcctgtggat caacattcca ctgggtctgc tggcaattat tgtctgcgct  660
ttcgtactga agctgcgcgt gggcgagcaa ggctttaagg gctttgactg gatgggtttt  720
gcggccgtcg caatcacgac cagcaccctg attctgctca ccacttgggg cggaagcgaa  780
tacgagtgga cttcccccaac tatttttgtcc atggctgacg tagtcatcgt ggcgcgcgta  840
ctcaccgtgt tcattgagtc gcgtgcatcc cagccgctga tcccggttca gctatttaag  900
aaccgcaaca tggttttgac caccctcgcc ggtactgttt gggtctggc catgatgggc  960
gtgctcggct acatgccaac ctacctgcag atggtgcaca ccctgacgcc aactgaagca 1020
ggcttgatga tgatcccgat gatggtcggc atgatcggtg tctccactgg tgttggcttc 1080
atcatcgcta agaccggcaa ctacaagtac tacccatcgc cgggcctggc catcacgcg 1140
tttgctttgt ggtggatgtc ccagatgacc gttgagactt cattgaccgg tatcggagtt 1200
cgcttccttg tattcggtgt cggcttgggc tttgtcatgc aggtactggt gctgattgtt 1260
caaaactcct tccctgtatc gcaggtcggt actgccacgg cggctaataa cttcttccgc 1320
cagattggtt cggcattggg tgcttccatc gtgggttcga tgttcattca caatatgcag 1380
aatgagatgg ctacccgttt gcctgatgcc cttgcatcgt tgggcaagga aggcgccgct 1440
atttcgcagc agttccaagg tgcagatgcc gccaactcct tgactccgca cgcagtcgca 1500
gagcttcccg atgtcctccg tgacgctatc ttaaattcct acaatgacgg tctgaccccc 1560
gtgattggca tgatggtgcc actggccatt gttgcaatgc tgattttgtt cccactgcgc 1620
caagagcgct tgaaggaaac catcgaataa                                  1650

SEQ ID NO: 137          moltype = AA   length = 549
FEATURE                 Location/Qualifiers
REGION                  1..549
                        note = CJI0323 impE2(G64D, F405Y)
source                  1..549
                        mol_type = protein
                        organism = unidentified
SEQUENCE: 137
MIAKNSTPST AGHASAHTAE EFPVANAEMA TPSAIDPNHG KKTADNVGII FAALMLTMLM   60
SSLDQMIFGS ALPTIVGELG GVDQMSWVIS AFMVTMTIAM PLAGQLGDRM GRKWVYISGI  120
SIFVIGSTLG GFANGMGMLI TGRAIQGFGA GIMMISSQSI VAEVVSARER GKFMGIMGGV  180
FGVSSVLGPV LGGWFTDGPG WRWGLWINIP LGLLAIIVCA FVLKLRVGEQ GFKGFDWMGF  240
AAIAITTSTL ILLTTWGGSE YEWTSPTILS MAAVVIVGAL LTVFIESRAS QPLIPVQLFK  300
NRNMVLTTLA GTVLGLAMMG VLGYMPTYLQ MVHTLTPTEA GLMMIPMMVG MIGVSTGVGF  360
IIAKTGNYKY YPIAGLAITA FALWWMSQMT VETSLTGIGV RFLVYGVGLG FVMQVLVLIV  420
QNSFPVSQVG TATAANNFFR QIGSALGASI VGSMFIHNMQ NEMATRLPDA LASLGKEGAA  480
ISQQFQGADA ANSLTPHAVA ELPDVLRDAI LNSYNDGLTP VIGMMVPLAI VAMLILFPLR  540
QERLKETIE                                                         549

SEQ ID NO: 138          moltype = DNA   length = 1650
FEATURE                 Location/Qualifiers
misc_feature            1..1650
                        note = CJI0323 impE2(G64D, F405Y)
source                  1..1650
                        mol_type = other DNA
                        organism = unidentified
SEQUENCE: 138
atgatagcta aaaactccac cccaagcacg gccggccacg ccagtgctca cactgcggaa   60
gaattcccag tggccaatgc tgaaatggca acgccttcag caatcgaccc aaaccacggt  120
aaaaagaccg cggataacgt cggcattatc ttcgctgcct tgatgctcac catgctgatg  180
agctctttgg accagatgat tttcggttcc gctctgccaa ccatcgtcgg cgagctcggc  240
ggcgtggacc agatgagctg ggtaatttca gcatttatgg tcaccatgac cattgctatg  300
ccactagccg gtcagctcgg tgaccgcatg ggccgcaagt gggtctacat ctcaggtatc  360
tccattttcg ttattggctc gacgctcggt ggctttgcca atggcatggg catgctgatc  420
```

```
accggacgtg caatccaggg cttcggtgcc ggcatcatga tgatttcctc gcagtcgatt    480
gtggctgagg ttgtctccgc acgtgagcgc ggcaagttca tgggtattat gggcggcgtc    540
tttggcgtct cctccgtact gggtccagtt ctcggtggct ggttcaccga tggtcccggt    600
tggcgttggg gcctgtggat caacattcca ctgggtctgc tggcaattat tgtctgcgct    660
ttcgtactga agctgcgcgt gggcgagcaa ggctttaagg gctttgactg gatgggtttt    720
gcggccatcg caatcacgac cagcaccctg attctgctca ccacttgggg cggaagcgaa    780
tacgagtgga cttccccaac tattttgtcc atggctgccg tagtcatcgt cggcgcgctg    840
ctcaccgtgt tcattgagtc gcgtgcatcc cagccgctga tcccggttca gctatttaag    900
aaccgcaaca tggttttgac caccctcgcc ggtactgttt gggtctggc catgatgggc     960
gtgctcggct acatgccaac ctacctgcag atggtgcaca ccctgacgcc aactgaagca    1020
ggcttgatga tgatcccgat gatggtcggc atgatcggtg tctccactgg tgttggcttc    1080
atcatcgcta agaccggcaa ctacaagtac taccccatcg cgggcctggc catcacggcg    1140
tttgctttgt ggtggatgtc ccagatgacc gttgagactt cattgaccgg tatcggagtt    1200
cgcttccttg tatacggtgt cggcttgggc tttgtcatgc aggtactggt gctgattgtt    1260
caaaactcct tccctgtatc gcaggtcggt actgccacgg cggctaataa cttcttccgc    1320
cagattggtt cggcattggg tgcttccatc gtgggttcga tgttcattca caatatgcag    1380
aatgagatgg ctacccgttt gcctgatgcc cttgcatcgt tgggcaagga aggcgccgct    1440
atttcgcagc agttccaagg tgcagatgcc gccaactcct tgactccgca cgcagtcgca    1500
gagcttcccg atgtcctccg tgacgctatc ttaaattcct acaatgacgg tctgaccccc    1560
gtgattggca tgatggtgcc actggccatt gttgcaatgc tgattttgtt cccactgcgc    1620
caagagcgct tgaaggaaac catcgaataa                                     1650
SEQ ID NO: 139         moltype = AA  length = 549
FEATURE                Location/Qualifiers
REGION                 1..549
                       note = CJI0323 impE2(F123C, I243V, S387T, F405Y, M413T,
                       N458K)
source                 1..549
                       mol_type = protein
                       organism = unidentified
SEQUENCE: 139
MIAKNSTPST AGHASAHTAE EFPVANAEMA TPSAIDPNHG KKTADNVGII FAALMLTMLM     60
SSLGQMIFGS ALPTIVGELG GVDQMSWVIS AFMVTMTIAM PLAGQLGDRM GRKWVYISGI    120
SICVIGSTLG GFANGMGMLI TGRAIQGFGA GIMMISSQSI VAEVVSARER GKFMGIMGGV    180
FGVSSVLGPV LGGWFTDGPG WRWGLWINIP LGLLAIIVCA FVLKLRVGEQ GFKGFDWMGF    240
AAVAITTSTL ILLTTWGGSE YEWTSPTILS MAAVVIVGAL LTVFIESRAS QPLIPVQLFK    300
NRNMVLTTLA GTVLGLAMMG VLGYMPTYLQ MVHTLTPTEA GLMMIPMMVG MIGVSTGVGF    360
IIAKTGNYKY YPIAGLAITA FALWWMTQMT VETSLTGIGV RFLVYGVGLG FVTQVLVLIV    420
QNSFPVSQVG TATAANNFFR QIGSALGASI VGSMFIHKMQ NEMATRLPDA LASLGKEGAA    480
ISQQFQGADA ANSLTPHAVA ELPDVLRDAI LNSYNDGLTP VIGMMVPLAI VAMLILFPLR    540
QERLKETIE                                                           549

SEQ ID NO: 140         moltype = DNA  length = 1650
FEATURE                Location/Qualifiers
misc_feature           1..1650
                       note = CJI0323 impE2(F123C, I243V, S387T, F405Y, M413T,
                       N458K)
source                 1..1650
                       mol_type = other DNA
                       organism = unidentified
SEQUENCE: 140
atgatagcta aaaactccac cccaagcacg gccggccacg ccagtgctca cactgcggaa     60
gaattcccag tggccaatgc tgaaatggca acgccttcag caatcgaccc aaaccacggt    120
aaaaagaccg cggataacgt cggcattatc ttcgctgcct tgatgctcac catgctgatg    180
agctctttgg ggcagatgat tttcggttcc gctctgccaa ccatcgtcgg cgagctcggc    240
ggcgtggacc agatgagctg ggtaatttca gcatttatgg tcaccatgac cattgctatg    300
ccactagccg gtcagctcgg tgaccgcatg ggccgcaagt gggtctacat ctcaggtatc    360
tccatttgcg ttattggctc gacgctcggt ggctttgcca atggcatggg catgctgatc    420
accggacgtg caatccaggg cttcggtgcc ggcatcatga tgatttcctc gcagtcgatt    480
gtggctgagg ttgtctccgc acgtgagcgc ggcaagttca tgggtattat gggcggcgtc    540
tttggcgtct cctccgtact gggtccagtt ctcggtggct ggttcaccga tggtcccggt    600
tggcgttggg gcctgtggat caacattcca ctgggtctgc tggcaattat tgtctgcgct    660
ttcgtactga agctgcgcgt gggcgagcaa ggctttaagg gctttgactg gatgggtttt    720
gcggccgtcg caatcacgac cagcaccctg attctgctca ccacttgggg cggaagcgaa    780
tacgagtgga cttccccaac tattttgtcc atggctgccg tagtcatcgt cggcgcgctg    840
ctcaccgtgt tcattgagtc gcgtgcatcc cagccgctga tcccggttca gctatttaag    900
aaccgcaaca tggttttgac caccctcgcc ggtactgttt gggtctggc catgatgggc     960
gtgctcggct acatgccaac ctacctgcag atggtgcaca ccctgacgcc aactgaagca    1020
ggcttgatga tgatcccgat gatggtcggc atgatcggtg tctccactgg tgttggcttc    1080
atcatcgcta agaccggcaa ctacaagtac taccccatcg cgggcctggc catcacggcg    1140
tttgctttgt ggtggatgac ccagatgacc gttgagactt cattgaccgg tatcggagtt    1200
cgcttccttg tatacggtgt cggcttgggc tttgtcacgc aggtactggt gctgattgtt    1260
caaaactcct tccctgtatc gcaggtcggt actgccacgg cggctaataa cttcttccgc    1320
cagattggtt cggcattggg tgcttccatc gtgggttcga tgttcattca caatatgcag    1380
aatgagatgg ctacccgttt gcctgatgcc cttgcatcgt tgggcaagga aggcgccgct    1440
atttcgcagc agttccaagg tgcagatgcc gccaactcct tgactccgca cgcagtcgca    1500
gagcttcccg atgtcctccg tgacgctatc ttaaattcct acaatgacgg tctgaccccc    1560
gtgattggca tgatggtgcc actggccatt gttgcaatgc tgattttgtt cccactgcgc    1620
caagagcgct tgaaggaaac catcgaataa                                     1650
```

```
SEQ ID NO: 141           moltype = AA  length = 549
FEATURE                  Location/Qualifiers
REGION                   1..549
                         note = CJI0323 impE2(G64D, S387T)
source                   1..549
                         mol_type = protein
                         organism = unidentified
SEQUENCE: 141
MIAKNSTPST AGHASAHTAE EFPVANAEMA TPSAIDPNHG KKTADNVGII FAALMLTMLM    60
SSLDQMIFGS ALPTIVGELG GVDQMSWVIS AFMVTMTIAM PLAGQLGDRM GRKWVYISGI   120
SIFVIGSTLG GFANGMGMLI TGRAIQGFGA GIMMISSQSI VAEVVSARER GKFMGIMGGV   180
FGVSSVLGPV LGGWFTDGPG WRWGLWINIP LGLLAIIVCA FVLKLRVGEQ GFKGFDWMGF   240
AAIAITTSTL ILLTTWGGSE YEWTSPTILS MAAVVIVGAL LTVFIESRAS QPLIPVQLFK   300
NRNMVLTTLA GTVLGLAMMG VLGYMPTYLQ MVHTLTPTEA GLMMIPMMVG MIGVSTGVGF   360
IIAKTGNYKY YPIAGLAITA FALWWMTQMT VETSLTGIGV RFLVFGVGLG FVMQVLVLIV   420
QNSFPVSQVG TATAANNFFR QIGSALGASI VGSMFIHNMQ NEMATRLPDA LASLGKEGAA   480
ISQQFQGADA ANSLTPHAVA ELPDVLRDAI LNSYNDGLTP VIGMMVPLAI VAMLILFPLR   540
QERLKETIE                                                          549

SEQ ID NO: 142           moltype = DNA  length = 1650
FEATURE                  Location/Qualifiers
misc_feature             1..1650
                         note = CJI0323 impE2(G64D, S387T)
source                   1..1650
                         mol_type = other DNA
                         organism = unidentified
SEQUENCE: 142
atgatagcta aaaactccac cccaagcacg gccggccacg ccagtgctca cactgcggaa     60
gaattcccag tggccaatgc tgaaatggca acgccttcga caatcgaccc aaaccacggt    120
aaaaagaccg cggataacgt cggcattatc ttcgctgcct tgatgctcac catgctgatg    180
agctctttgg accagatgat tttcggttcc gctctgccaa ccatcgtcgg cgagctcggc    240
ggcgtggacc agatgagctg ggtaatttca gcatttatgg tcaccatgac cattgctatg    300
ccactagccg gtcagctcgg tgaccgcatg ggccgcaagt gggtctacat ctcaggtatc    360
tccattttcg ttattggctc gacgctcggt ggctttgcca atggcatggg catgctgatc    420
accggacgtg caatccaggg cttcggtgcc ggcatcatga tgatttcctc gcagtcgatt    480
gtggctgagg ttgtctccgc acgtgagcgc ggcaagttca tgggtattat gggcggcgtc    540
tttggcgtct cctccgtact gggtccagtt ctcggtggct ggttcaccga tggtcccggt    600
tggcgttggg gcctgtggat caacattcca ctgggtctgc tggcaattat tgtctgcgct    660
ttcgtactga agctgcgcgt gggcgagcaa ggctttaagg gctttgactg gatgggtttt    720
gcggccatcg caatcacgac cagcaccctg attctgctca ccacttgggg cggaagcgaa    780
tacgagtgga cttccccaac tattttgtcc atggctgccg tagtcatcgt cggcgcgctg    840
ctcaccgtgt tcattgagtc gcgtgcatcc cagccgctga tcccgttca gctatttaag    900
aaccgcaaca tggttttgac caccctcgcc ggtactgttt tgggtctggc catgatgggc    960
gtgctcggct acatgccaac ctacctgcag atggtgcaca ccctgacgcc aactgaagca   1020
ggcttgatga tgatcccgat gatggtcggc atgatcggtg tctccactgg tgttggcttc   1080
atcatcgcta agaccggcaa ctacaagtac taccccatcg gggcctggc catcacggcg   1140
tttgctttgt ggtggatgac ccagatgacc gttgagactt cattgaccgg tatcggagtt   1200
cgcttccttg tattcggtgt cggcttgggc tttgtcatgc aggtactggt gctgattgtt   1260
caaaactcct ccctgtatc gcaggtcggt actgccacgg cggctaataa cttcttccgc   1320
cagattggtt cggcattggg tgcttccatc gtgggtttca tgttcattca caatgtgcag   1380
aatgagatgg ctacccgttt gcctgatgcc cttgcatcgt tgggcaagga aggcgccgct   1440
atttcgcagc agttccaagg tgcagatgcc gccaactcct tgactccgca cgcagtcgca   1500
gagcttcccg atgtcctccg tgacgctatc ttaaattcct acaatgacgg tctgacccc    1560
gtgattggca tgatggtgcc actggccatt gttgcaatgc tgattttgtt cccactgcgc   1620
caagagcgct tgaaggaaac catcgaataa                                    1650

SEQ ID NO: 143           moltype = AA  length = 549
FEATURE                  Location/Qualifiers
REGION                   1..549
                         note = CJI0323 impE2(G64D, M413T)
source                   1..549
                         mol_type = protein
                         organism = unidentified
SEQUENCE: 143
MIAKNSTPST AGHASAHTAE EFPVANAEMA TPSAIDPNHG KKTADNVGII FAALMLTMLM    60
SSLDQMIFGS ALPTIVGELG GVDQMSWVIS AFMVTMTIAM PLAGQLGDRM GRKWVYISGI   120
SIFVIGSTLG GFANGMGMLI TGRAIQGFGA GIMMISSQSI VAEVVSARER GKFMGIMGGV   180
FGVSSVLGPV LGGWFTDGPG WRWGLWINIP LGLLAIIVCA FVLKLRVGEQ GFKGFDWMGF   240
AAIAITTSTL ILLTTWGGSE YEWTSPTILS MAAVVIVGAL LTVFIESRAS QPLIPVQLFK   300
NRNMVLTTLA GTVLGLAMMG VLGYMPTYLQ MVHTLTPTEA GLMMIPMMVG MIGVSTGVGF   360
IIAKTGNYKY YPIAGLAITA FALWWMSQMT VETSLTGIGV RFLVFGVGLG FVTQVLVLIV   420
QNSFPVSQVG TATAANNFFR QIGSALGASI VGSMFIHNMQ NEMATRLPDA LASLGKEGAA   480
ISQQFQGADA ANSLTPHAVA ELPDVLRDAI LNSYNDGLTP VIGMMVPLAI VAMLILFPLR   540
QERLKETIE                                                          549

SEQ ID NO: 144           moltype = DNA  length = 1650
FEATURE                  Location/Qualifiers
misc_feature             1..1650
```

|   |   |   |
|---|---|---|
|   | note = | CJI0323 impE2(G64D, M413T) |
| source | 1..1650 |   |
|   | mol_type = other DNA |   |
|   | organism = unidentified |   |

SEQUENCE: 144

```
atgatagcta aaaactccac cccaagcacg gccggccacg ccagtgctca cactgcggaa   60
gaattcccag tggccaatgc tgaaatggca acgccttcag caatcgaccc aaaccacggt  120
aaaaagaccg cggataacgt cggcattatc ttcgctgcct tgatgctcac catgctgatg  180
agctctttgg accagatgat tttcggttcc gctctgccaa ccatcgtcgg cgagctcggc  240
ggcgtggacc agatgagctg ggtaatttca gcatttatgg tcaccatgac cattgctatg  300
ccactagccg gtcagctcgg tgaccgcatg ggccgcaagt gggtctacat ctcaggtatc  360
tccatttttg ttattggctc gacgctcggt ggctttgcca atggcatggg catgctgatc  420
accggacgtg caatccaggg cttcggtgcc ggcatcatga tgatttcctc gcagtcgatt  480
gtggctgagg ttgtctccgc acgtgagcgc ggcaagttca tgggtattat gggcggcgtc  540
tttggcgtct cctccgtact gggtccagtt ctcggtggct ggttcaccga tggtcccggt  600
tggcgttggg gcctgtggat caacattcca ctgggtctgc tggcaattat tgtctgcgct  660
ttcgtactga agctgcgcgt gggcgagcaa ggctttaagg ctttgactg gatgggtttt  720
gcggccatcg caatcacgac cagcaccctg attctgctca ccacttgggg cggaagcgaa  780
tacgagtgga cttccccaac tatttttgtcc atggctgccg tagtcatcgt cggcgcgctg  840
ctcaccgtgt tcattgagtc gcgtgcatcc cagccgctga tcccggttca gctatttaag  900
aaccgcaaca tggttttgac caccctcgcc ggtactgttt tgggtctggc catgatgggc  960
gtgctcggct acatgccaac ctacctgcag atggtgcaca ccctgacgcc aactgaagca 1020
ggcttgatga tgatcccgat gatggtcggc atgatcggtg tctccactgg tgttggcttc 1080
atcatcgcta agaccggcaa ctacaagtac tacccatcg cgggcctggc catcacggcg 1140
tttgctttgt ggtggatgtc ccagatgacc gttgagactt cattgaccgg tatcggagtt 1200
cgcttccttg tattcggtgt cggcttgggc tttgtcacgc aggtactggt gctgattgtt 1260
caaaactcct tccctgtatc gcaggtcggt actgccacgc cggctaataa cttcttccgc 1320
cagattggtt cggcattggg tgcttccatc gtgggttcga tgttcattca caatatgcag 1380
aatgagatgg ctacccgttt gcctgatgcc cttgcatcgt tgggcaagga aggcgccgct 1440
atttcgcagc agttccaagg tgcagatgcc gccaactcct tgactccgca cgcagtcgca 1500
gagcttcccg atgtcctccg tgacgctatc ttaaattcct acaatgacgg tctgacccca 1560
gtgattggca tgatggtgcc actggccatt gttgcaatgc tgattttgtt cccactgcgc 1620
caagagcgct tgaaggaaac catcgaataa                                  1650
```

| SEQ ID NO: 146 | moltype = DNA  length = 1650 |
|---|---|
| FEATURE | Location/Qualifiers |
| REGION | 1..549 |
|   | note = CJI0323 impE2(G64D, N458K) |
| source | 1..549 |
|   | mol_type = protein |
|   | organism = unidentified |

SEQUENCE: 145

```
MIAKNSTPST AGHASAHTAE EFPVANAEMA TPSAIDPNHG KKTADNVGII FAALMLTMLM   60
SSLDQMIFGS ALPTIVGELG GVDQMSWVIS AFMVTMTIAM PLAGQLGDRM GRKWVYISGI  120
SIFVIGSTLG GFANGMGMLI TGRAIQGFGA GIMMISSQSI VAEVVSARER GKFMGIMGGV  180
FGVSSVLGPV LGGWFTDGPG WRWGLWINIP LGLLAIIVCA FVLKLRVGEQ GFKGFDWMGF  240
AAIAITTSTL ILLTTWGGSE YEWTSPTILS MAAVVIVGAL LTVFIESRAS QPLIPVQLFK  300
NRNMVLTTLA GTVLGLAMMG VLGYMPTYLQ MVHTLTPTEA GLMMIPMMVG MIGVSTGVGF  360
IIAKTGNYKY YPIAGLAITA FALWWMSQMT VETSLTGIGV RFLVFGVGLG FVMQVLVLIV  420
QNSFPVSQVG TATAANNFFR QIGSALGASI VGSMFIHKMQ NEMATRLPDA LASLGKEGAA  480
ISQQFQGADA ANSLTPHAVA ELPDVLRDAI LNSYNDGLTP VIGMMVPLAI VAMLILFPLR  540
QERLKETIE                                                         549
```

| SEQ ID NO: 146 | moltype = DNA  length = 1650 |
|---|---|
| FEATURE | Location/Qualifiers |
| misc_feature | 1..1650 |
|   | note = CJI0323 impE2(G64D, N458K) |
| source | 1..1650 |
|   | mol_type = other DNA |
|   | organism = unidentified |

SEQUENCE: 146

```
atgatagcta aaaactccac cccaagcacg gccggccacg ccagtgctca cactgcggaa   60
gaattcccag tggccaatgc tgaaatggca acgccttcag caatcgaccc aaaccacggt  120
aaaaagaccg cggataacgt cggcattatc ttcgctgcct tgatgctcac catgctgatg  180
agctctttgg accagatgat tttcggttcc gctctgccaa ccatcgtcgg cgagctcggc  240
ggcgtggacc agatgagctg ggtaatttca gcatttatgg tcaccatgac cattgctatg  300
ccactagccg gtcagctcgg tgaccgcatg ggccgcaagt gggtctacat ctcaggtatc  360
tccatttttg ttattggctc gacgctcggt ggctttgcca atggcatggg catgctgatc  420
accggacgtg caatccaggg cttcggtgcc ggcatcatga tgatttcctc gcagtcgatt  480
gtggctgagg ttgtctccgc acgtgagcgc ggcaagttca tgggtattat gggcggcgtc  540
tttggcgtct cctccgtact gggtccagtt ctcggtggct ggttcaccga tggtcccggt  600
tggcgttggg gcctgtggat caacattcca ctgggtctgc tggcaattat tgtctgcgct  660
ttcgtactga agctgcgcgt gggcgagcaa ggctttaagg ctttgactg gatgggtttt  720
gcggccatcg caatcacgac cagcaccctg attctgctca ccacttgggg cggaagcgaa  780
tacgagtgga cttccccaac tatttttgtcc atggctgccg tagtcatcgt cggcgcgctg  840
ctcaccgtgt tcattgagtc gcgtgcatcc cagccgctga tcccggttca gctatttaag  900
aaccgcaaca tggttttgac caccctcgcc ggtactgttt tgggtctggc catgatgggc  960
gtgctcggct acatgccaac ctacctgcag atggtgcaca ccctgacgcc aactgaagca 1020
ggcttgatga tgatcccgat gatggtcggc atgatcggtg tctccactgg tgttggcttc 1080
```

```
atcatcgcta agaccggcaa ctacaagtac tacccaatcg cgggcctggc catcacggcg  1140
tttgctttgt ggtggatgtc ccagatgacc gttgagactt cattgaccgg tatcggagtt  1200
cgcttccttg tattcggtgt cggcttgggc tttgtcatgc aggtactggt gctgattgtt  1260
caaaactcct tccctgtatc gcaggtcggt actgccacgg cggctaataa cttcttccgc  1320
cagattggtt cggcattggg tgcttccatc gtggttcga tgttcattca caaaatgcag  1380
aatgagatgg ctacccgttt gcctgatgcc cttgcatcgt tgggcaagga aggcgccgct  1440
atttcgcagc agttccaagg tgcagatgcc gccaactcct tgactccgca cgcagtcgca  1500
gagcttcccg atgtcctccg tgacgctatc ttaaattcct acaatgacgg tctgaccccc  1560
gtgattggca tgatggtgcc actggccatt gttgcaatgc tgattttgtt cccactcgcg  1620
caagagcgct tgaaggaaac catcgaataa                                    1650

SEQ ID NO: 147         moltype = AA  length = 549
FEATURE                Location/Qualifiers
REGION                 1..549
                       note = CJI0323 impE2(G64D, I243V, S387T, M413T, N458K)
source                 1..549
                       mol_type = protein
                       organism = unidentified
SEQUENCE: 147
MIAKNSTPST AGHASAHTAE EFPVANAEMA TPSAIDPNHG KKTADNVGII FAALMLTMLM   60
SSLDQMIFGS ALPTIVGELG GVDQMSWVIS AFMVTMTIAM PLAGQLGDRM GRKWVYISGI  120
SIFVIGSTLG GFANGMGMLI TGRAIQGFGA GIMMISSQSI VAEVVSARER GKFMGIMGGV  180
FGVSSVLGPV LGGWFTDGPG WRWGLWINIP LGLLAIIVCA FVLKLRVGEQ GFKGFDWMGF  240
AAVAITTSTL ILLTTWGGSE YEWTSPTILS MAAVVIVGAL LTVFIESRAS QPLIPVQLFK  300
NRNMVLTTLA GTVLGLAMMG VLGYMPTYLQ MVHTLTPTEA GLMMIPMMVG MIGVSTGVGF  360
IIAKTGNYKY YPIAGLAITA FALWWMTQMT VETSLTGIGV RFLVFGVGLG FVTQVLVLIV  420
QNSFPVSQVG TATAANNFFR QIGSALGASI VGSMFIHKMQ NEMATRLPDA LASLGKEGAA  480
ISQQFQGADA ANSLTPHAVA ELPDVLRDAI LNSYNDGLTP VIGMMVPLAI VAMLILFPLR  540
QERLKETIE                                                          549

SEQ ID NO: 148         moltype = DNA  length = 1650
FEATURE                Location/Qualifiers
misc_feature           1..1650
                       note = CJI0323 impE2(G64D, I243V, S387T, M413T, N458K)
source                 1..1650
                       mol_type = other DNA
                       organism = unidentified
SEQUENCE: 148
atgatagcta aaaactccac cccaagcacg gccggccacg ccagtgctca cactgcggaa   60
gaattcccag tggccaatgc tgaaatggca acgccttcag caatcgaccc aaaccacggt  120
aaaaagaccg cggataacgt cggcattatc ttcgctgcct tgatgctcac catgctgatg  180
agctctttgg accagatgat ttccggttcc gctctgccaa ccatcgtcgg cgagctcggc  240
ggcgtggacc agatgagctg ggtaattca gcatttatgg tcaccatgac cattgctatg  300
ccactagccg gtcagctcgg tgaccgcatg ggccgcaagt gggtctacat ctcaggtatc  360
tccatttttg ttattggctc gacgctcggt ggctttgcca atggcatggg catgctgatc  420
accggacgtg caatccaggg cttcggtgcc ggcatcatga tgatttcctc gcagtcgatt  480
gtggctgagg ttgtctccgc acgtgagcgc ggcaagttca tggggatat gggcggcgtc  540
tttggcgtct cctccgtact gggtccagtt ctcggtggct ggttcaccga tggtcccggt  600
tggcgttggg gcctcgtggat caacattcca ctgggtctgc tggcaattat tgtctgcgct  660
ttcgtactga agctgcgcgt gggcgagcaa ggctttaagg gctttgactg gatgggtttt  720
gcggccgtcg caatcacgac cagcaccctg attctgctca ccacttgggg cggaagcgaa  780
tacgagtgga cttccccaac tattttgtcc atggctgccg tagtcatcgt cggcgcgctg  840
ctcaccgtgt tcattgagtc gcgtgcatcc cagccgctga tcccggttca gctatttaag  900
aaccgcaaca tggttttgac caccctcgcc ggtactgttt gggtctggc catgatgggc  960
gtgctcggct acatgccaac tacctgcag atggtgcaca ccctgacgcc aactgaagca 1020
ggcttgatga tgatcccgat gatggtcggc atgatcggtg tctccactgg tgttggcttc 1080
atcatcgcta agaccggcaa ctacaagtac tacccatcg cgggcctggc catcacggcg 1140
tttgctttgt ggtggatgac ccagatgacc gttgagactt cattgaccgg tatcggagtt 1200
cgcttccttg tattcggtgt cggcttgggc tttgtcacgc aggtactggt gctgattgtt 1260
caaaactcct tccctgtatc gcaggtcggt actgccacgg cggctaataa cttcttccgc 1320
cagattggtt cggcattggg tgcttccatc gtggttcgga tgttcattca caaaatgcag 1380
aatgagatgg ctacccgttt gcctgatgcc cttgcatcgt tgggcaagga aggcgccgct 1440
atttcgcagc agttccaagg tgcagatgcc gccaactcct tgactccgca cgcagtcgca 1500
gagcttcccg atgtcctccg tgacgctatc ttaaattcct acaatgacgg tctgaccccc 1560
gtgattggca tgatggtgcc actggccatt gttgcaatgc tgattttgtt cccactcgcg 1620
caagagcgct tgaaggaaac catcgaataa                                   1650

SEQ ID NO: 149         moltype = AA  length = 549
FEATURE                Location/Qualifiers
REGION                 1..549
                       note = CJI0323 impE2(G64D, S387T, F405Y, M413T, N458K)
source                 1..549
                       mol_type = protein
                       organism = unidentified
SEQUENCE: 149
MIAKNSTPST AGHASAHTAE EFPVANAEMA TPSAIDPNHG KKTADNVGII FAALMLTMLM   60
SSLDQMIFGS ALPTIVGELG GVDQMSWVIS AFMVTMTIAM PLAGQLGDRM GRKWVYISGI  120
SIFVIGSTLG GFANGMGMLI TGRAIQGFGA GIMMISSQSI VAEVVSARER GKFMGIMGGV  180
FGVSSVLGPV LGGWFTDGPG WRWGLWINIP LGLLAIIVCA FVLKLRVGEQ GFKGFDWMGF  240
```

```
AAIAITTSTL ILLTTWGGSE YEWTSPTILS MAAVVIVGAL LTVFIESRAS QPLIPVQLFK    300
NRNMVLTTLA GTVLGLAMMG VLGYMPTYLQ MVHTLTPTEA GLMMIPMMVG MIGVSTGVGF    360
IIAKTGNYKY YPIAGLAITA FALWWMTQMT VETSLTGIGV RFLVYGVGLG FVTQVLVLIV    420
QNSFPVSQVG TATAANNFFR QIGSALGASI VGSMFIHKMQ NEMATRLPDA LASLGKEGAA    480
ISQQFQGADA ANSLTPHAVA ELPDVLRDAI LNSYNDGLTP VIGMMVPLAI VAMLILFPLR    540
QERLKETIE                                                            549

SEQ ID NO: 150          moltype = DNA  length = 1650
FEATURE                 Location/Qualifiers
misc_feature            1..1650
                        note = CJI0323 impE2(G64D, S387T, F405Y, M413T, N458K)
source                  1..1650
                        mol_type = other DNA
                        organism = unidentified
SEQUENCE: 150
atgatagcta aaaactccac cccaagcacg gccggccacg ccagtgctca cactgcggaa    60
gaattcccag tggccaatgc tgaaatggca acgccttcag caatcgaccc aaaccacggt    120
aaaaagaccg cggataacgt cggcattatc ttcgctgcct tgatgctcac catgctgatg    180
agctcttttgg accagatgat tttcggttcc gctctgccaa ccatcgtcgg cgagctcggc    240
ggcgtggacc agatgagctg gtaatttca gcatttatgg tcaccatgac cattgctatg    300
ccactagccg gtcagctcgg tgaccgcatg ggccgcaagt gggtctacat ctcaggtatc    360
tccattttcg ttattggctc gacgctcggt ggctttgcca atggcatggg catgctgatc    420
accggacgtg caatccaggg cttcggtgcc ggcatcatga tgatttcctc gcagtcgatt    480
gtggctgagg ttgtctccgc acgtgagcgc ggcaagttca tgggtattat gggcggcgtc    540
tttgcgtcct cctccgtact gggtccagtt ctcggtggct ggttcaccga tggtcccggt    600
tggcgttggg gcctgtggat caacattcca ctgggtctgc tgcaattat tgtctgcgtt    660
ttcgtactga agctgcgcgt gggcgagcaa gctttaagg gctttgactg gatgggtttt    720
gcggccatcg caatcacgac cagcaccctg attctgctca ccacttgggg cggaagcgaa    780
tacgagtgga cttccccaac tatttttgtcc atggctgccg tagtcatcgt cggcgcgctg    840
ctcaccgtgt tcattgagtc gcgtgcatcc cagccgctga tcccggttca gctatttaag    900
aaccgcaaca tggttttgac caccctcgcc ggtactgttt ggggtctggc catgatgggc    960
gtgctcggct acatgccaac ctacctgcag atggtgcaca ccctgacgcc aactgaagca    1020
ggcttgatga tgatcccgat gatggtcggc atgatcggtg tctccactgg tgttggcttc    1080
atcatcgcta agaccggcaa ctacaagtac taccccatcg cgggcctggc catcacggcg    1140
tttgctttgt ggtggatgac ccagatgacc gttgagactt cattgaccgg tatcggagtt    1200
cgcttccttg tatacggtgt cggcttgggc tttgtcacgc aggtactggt gctgattgtt    1260
caaaactcct ccctgtatcg caggtcggt actgccacgg cggctaataa cttcttccgc    1320
cagattggtt cggcattggg tgcttccatc gtgggttcga tgttcattca caaaatgcag    1380
aatgagatgg ctacccgttt gcctgatgcc cttgcatcgt tgggcaagga aggcgccgct    1440
atttcgcagc agttccaagg tgcagatgcc gccaactcct tgactccgca cgcagtcgca    1500
gagcttcccg atgtcctccg tgacgctatc ttaaattcct acaatgacgg tctgacccc    1560
gtgattggca tgatggtgcc actggccatt gttgcaatgc tgattttgtt cccactgcgc    1620
caagagcgct tgaaggaaac catcgaataa                                     1650

SEQ ID NO: 151          moltype = AA  length = 549
FEATURE                 Location/Qualifiers
REGION                  1..549
                        note = CJI0323 impE2(G64D, F123C, S387T, M413T, N458K)
source                  1..549
                        mol_type = protein
                        organism = unidentified
SEQUENCE: 151
MIAKNSTPST AGHASAHTAE EFPVANAEMA TPSAIDPNHG KKTADNVGII FAALMLTMLM    60
SSLDQMIFGS ALPTIVGELG GVDQMSWVIS AFMVTMTIAM PLAGQLGDRM GRKWVYISGI    120
SICVIGSTLG GFANGMGMLI TGRAIQGFGA GIMMISSQSI VAEVVSARER GKFMGIMGGV    180
FGVSSVLGPV LGGWFTDGPG WRWGLWINIP LGLLAIIVCA FVLKLRVGEQ GFKGFDWMGF    240
AAIAITTSTL ILLTTWGGSE YEWTSPTILS MAAVVIVGAL LTVFIESRAS QPLIPVQLFK    300
NRNMVLTTLA GTVLGLAMMG VLGYMPTYLQ MVHTLTPTEA GLMMIPMMVG MIGVSTGVGF    360
IIAKTGNYKY YPIAGLAITA FALWWMTQMT VETSLTGIGV RFLVYGVGLG FVTQVLVLIV    420
QNSFPVSQVG TATAANNFFR QIGSALGASI VGSMFIHKMQ NEMATRLPDA LASLGKEGAA    480
ISQQFQGADA ANSLTPHAVA ELPDVLRDAI LNSYNDGLTP VIGMMVPLAI VAMLILFPLR    540
QERLKETIE                                                            549

SEQ ID NO: 152          moltype = DNA  length = 1650
FEATURE                 Location/Qualifiers
misc_feature            1..1650
                        note = CJI0323 impE2(G64D, F123C, S387T, M413T, N458K)
source                  1..1650
                        mol_type = other DNA
                        organism = unidentified
SEQUENCE: 152
atgatagcta aaaactccac cccaagcacg gccggccacg ccagtgctca cactgcggaa    60
gaattcccag tggccaatgc tgaaatggca acgccttcag caatcgaccc aaaccacggt    120
aaaaagaccg cggataacgt cggcattatc ttcgctgcct tgatgctcac catgctgatg    180
agctcttttgg accagatgat tttcggttcc gctctgccaa ccatcgtcgg cgagctcggc    240
ggcgtggacc agatgagctg gtaatttca gcatttatgg tcaccatgac cattgctatg    300
ccactagccg gtcagctcgg tgaccgcatg ggccgcaagt gggtctacat ctcaggtatc    360
tccatttgcg ttattggctc gacgctcggt ggctttgcca atggcatggg catgctgatc    420
accggacgtg caatccaggg cttcggtgcc ggcatcatga tgatttcctc gcagtcgatt    480
```

-continued

```
gtggctgagg ttgtctccgc acgtgagcgc ggcaagttca tgggtattat gggcggcgtc    540
tttggcgtct cctccgtact gggtccagtt ctcggtggct ggttcaccga tggtcccggt    600
tggcgttggg gcctgtggat caacattcca ctgggtctgc tggcaattat tgtctgcgct    660
ttcgtactga agctgcgcgt gggcgagcaa ggctttaagg ctttgactg gatgggtttt    720
gcggccatcg caatcacgac cagcaccctg attctgctca ccacttgggg cggaagcgaa    780
tacgagtgga cttccccaac tattttgtcc atggctgccg tagtcatcgt cggcgcgctg    840
ctcaccgtgt tcattgagtc gcgtgcatcc cagccgctga tcccggttca gctatttaag    900
aaccgcaaca tggttttgac caccctcgcc ggtactgttt gggtctggc catgatgggc    960
gtgctcggct acatgccaac ctacctgcag atggtgcaca ccctgacgcc aactgaagca   1020
ggcttgatga tgatcccgat gatggtcggc atgatcggtg tctccactgg tgttggcttc   1080
atcatcgcta agaccggcaa ctacaagtac taccccatcg cgggcctggc catcacggcg   1140
tttgctttgt ggtggatgac ccagatgacc gttgagactt cattgaccgg tatcggagtt   1200
cgcttccttg tattcggtgt cggcttgggc tttgtcacgc aggtactggt gctgattgtt   1260
caaaactcct tccctgtatc gcaggtcggt actgccacgg cgctaataa cttcttccgc    1320
cagattggtt cggcattggg tgcttccatc gtgggttcga tgttcattca caaatgcag   1380
aatgagatgg ctacccgttt gcctgatgcc cttgcatcgt tgggcaagga aggcgccgct   1440
atttcgcagc agttccaagg tgcagatgcc gccaactcct tgactccgca cgcagtcgca   1500
gagcttcccg atgtcctccg tgacgctatc ttaaattcct acaatgacgg tctgacccc   1560
gtgattggca tgatggtgcc actggccatt gttgcaatgc tgattttgtt cccactgcgc   1620
caagagcgct tgaaggaaac catcgaataa                                     1650
```

SEQ ID NO: 153          moltype = AA  length = 549
FEATURE               Location/Qualifiers
REGION                1..549
                        note = CJI0323 impE2(G64D, I243V, S387T, F405Y, M413T,
                        N458K)
source                1..549
                        mol_type = protein
                        organism = unidentified
SEQUENCE: 153
MIAKNSTPST AGHASAHTAE EFPVANAEMA TPSAIDPNHG KKTADNVGII FAALMLTMLM    60
SSLDQMIFGS ALPTIVGELG GVDQMSWVIS AFMVTMTIAM PLAGQLGDRM GRKWVYISGI   120
SIFVIGSTLG GFANGMGMLI TGRAIQGFGA GIMMISSQSI VAEVVSARER GKFMGIMGGV   180
FGVSSVLGPV LGGWFTDGPG WRWGLWINIP LGLLAIIVCA FVLKLRVGEQ GFKGFDWMGF   240
AAVAITTSTL ILLTTWGGSE YEWTSPTILS MAAVVIVGAL LTVFIESRAS QPLIPVQLFK   300
NRNMVLTTLA GTVLGLAMMG VLGYMPTYLQ MVHTLTPTEA GLMMIPMMVG MIGVSTGVGF   360
IIAKTGNYKY YPIAGLAITA FALWWMTQMT VETSLTGIGV RFLVYGVGLG FVTQVLVLIV   420
QNSFPVSQVG TATAANNFFR QIGSALGASI VGSMFIHKMQ NEMATRLPDA LASLGKEGAA   480
ISQQFQGADA ANSLTPHAVA ELPDVLRDAI LNSYNDGLTP VIGMMVPLAI VAMLILFPLR   540
QERLKETIE                                                            549

SEQ ID NO: 154          moltype = DNA  length = 1650
FEATURE               Location/Qualifiers
misc_feature        1..1650
                        note = CJI0323 impE2(G64D, I243V, S387T, F405Y, M413T,
                        N458K)
source                1..1650
                        mol_type = other DNA
                        organism = unidentified
SEQUENCE: 154

```
atgatagcta aaaactccac cccaagcacg gccggccacg ccagtgctca cactgcggaa     60
gaattcccag tggccaatgc tgaaatggca acgccttcag caatcgaccc aaaccacggt    120
aaaaagaccg cggataacgt cggcattatc ttcgctgcct tgatgctcac catgctgatg    180
agctctttgg accagatgat tttcggttcc gctctgccaa ccatcgtcgg cgagctcggc    240
ggcgtggacc agatgagctg ggtaaattca gcatttatgg tcaccatgac cattgctatg    300
ccactagccg gtcagctcgg tgaccgcatg ggccgcaagt gggtctacat ctcaggtatc    360
tccatttttcg ttattggctc gacgctcggg ggctttgcca atggcatggg catgctgatc    420
accggacgtg caatccaggg cttcggtgcc ggcatcatga tgatttcctc gcagtcgatt    480
gtggctgagg ttgtctccgc acgtgagcgc ggcaagttca tgggtattat gggcggcgtc    540
tttggcgtct cctccgtact gggtccagtt ctcggtggct ggttcaccga tggtcccggt    600
tggcgttggg gcctgtggat caacattcca ctgggtctgc tggcaattat tgtctgcgct    660
ttcgtactga agctgcgcgt gggcgagcaa ggctttaagg ctttgactg gatgggtttt    720
gcggccgtca atcacgac cagcaccctg attctgctca ccacttgggg cggaagcgaa    780
tacgagtgga cttccccaac tattttgtcc atggctgccg tagtcatcgt cggcgcgctg    840
ctcaccgtgt tcattgagtc gcgtgcatcc cagccgctga tcccggttca gctatttaag    900
aaccgcaaca tggttttgac caccctcgcc ggtactgttt gggtctggc catgatgggc    960
gtgctcggct acatgccaac ctacctgcag atggtgcaca ccctgacgcc aactgaagca   1020
ggcttgatga tgatcccgat gatggtcggc atgatcggtg tctccactgg tgttggcttc   1080
atcatcgcta agaccggcaa ctacaagtac taccccatcg cgggcctggc catcacggcg   1140
tttgctttgt ggtggatgac ccagatgacc gttgagactt cattgaccgg tatcggagtt   1200
cgcttccttg tatacggtgt cggcttgggc tttgtcacgc aggtactggt gctgattgtt   1260
caaaactcct tccctgtatc gcaggtcggt actgccacgg cgctaataa cttcttccgc    1320
cagattggtt cggcattggg tgcttccatc gtgggttcga tgttcattca caaatgcag   1380
aatgagatgg ctacccgttt gcctgatgcc cttgcatcgt tgggcaagga aggcgccgct   1440
atttcgcagc agttccaagg tgcagatgcc gccaactcct tgactccgca cgcagtcgca   1500
gagcttcccg atgtcctccg tgacgctatc ttaaattcct acaatgacgg tctgacccc    1560
gtgattggca tgatggtgcc actggccatt gttgcaatgc tgattttgtt cccactgcgc   1620
caagagcgct tgaaggaaac catcgaataa                                     1650
```

```
SEQ ID NO: 155         moltype = AA  length = 549
FEATURE                Location/Qualifiers
REGION                 1..549
                       note = CJI0323 impE2(G64D, F123C, I243V, S387T, F405Y,
                       M413T, N458K)
source                 1..549
                       mol_type = protein
                       organism = unidentified
SEQUENCE: 155
MIAKNSTPST AGHASAHTAE EFPVANAEMA TPSAIDPNHG KKTADNVGII FAALMLTMLM   60
SSLDQMIFGS ALPTIVGELG GVDQMSWVIS AFMVTMTIAM PLAGQLGDRM GRKWVYISGI  120
SICVIGSTLG GFANGMGMLI TGRAIQGFGA GIMMISSQSI VAEVVSARER GKFMGIMGGV  180
FGVSSVLGPV LGGWFTDGPG WRWGLWINIP LGLLAIIVCA FVLKLRVGEQ GFKGFDWMGF  240
AAVAITTSTL ILLTTWGGSE YEWTSPTILS MAAVVIVGAL LTVFIESRAS QPLIPVQLFK  300
NRNMVLTTLA GTVLGLAMMG VLGYMPTYLQ MVHTLTPTEA GLMMIPMMVG MIGVSTGVGF  360
IIAKTGNYKY YPIAGLAITA FALWWMTQMT VETSLTGIGV RFLVYGVGLG FVTQVLVLIV  420
QNSFPVSQVG TATAANNFFR QIGSALGASI VGSMFIHKMQ NEMATRLPDA LASLGKEGAA  480
ISQQFQGADA ANSLTPHAVA ELPDVLRDAI LNSYNDGLTP VIGMMVPLAI VAMLILFPLR  540
QERLKETIE                                                         549

SEQ ID NO: 156         moltype = DNA  length = 1650
FEATURE                Location/Qualifiers
misc_feature           1..1650
                       note = CJI0323 impE2(G64D, F123C, I243V, S387T, F405Y,
                       M413T, N458K)
source                 1..1650
                       mol_type = other DNA
                       organism = unidentified
SEQUENCE: 156
atgatagcta aaaactccac cccaagcacg gccggccacg ccagtgctca cactgcggaa    60
gaattcccag tggccaatgc tgaaatggca acgccttcag caatcgaccc aaaccacggt   120
aaaaagaccg cggataacgt cggcattatc ttcgctgcct tgatgctcac catgctgatg   180
agctctttgg accagatgat tttcggttcc gctctgccaa ccatcgtcgg cgagctcggc   240
ggcgtggacc agatgagctg ggtaatttca gcatttatgg tcaccatgac cattgctatg   300
ccactagccg gtcagctcgg tgaccgcatg ggccgcaagt gggtctacat ctcaggtatc   360
tccatttgcg ttattggctc gacgctcggt ggctttgcca atggcatggg catgctgatc   420
accggacgtg caatccaggg cttcggtgcc ggcatcatga tgatttcctc gcagtcgatt   480
gtggctgagg ttgtctccgc acgtgagcgc ggcaagttca tgggtattat gggcggcgtc   540
tttggcgtct cctccgtact gggtccagtt ctcggtgggt ggttcaccga tggtcccggt   600
tggcgttggg gcctgtggat caacattcca ctgggtctgc tggcaattat tgtctgcgct   660
ttcgtactga agctgcgcgt gggcgagcaa ggctttaagg gctttgactg gatgggtttt   720
gcggccgtcg caatcacgac cagcacccfg attctgctca ccacttgggg cggaagcgaa   780
tacgagtgga cttccccaac tattttgtcc atggctgccg tagtcatcgt cggcgcgctg   840
ctcaccgtgt tcattgagtc gcgtgcatcc cagccgctga tcccggttca gctatttaag   900
aaccgcaaca tggttttgac caccctcgcc ggtactgttt gggtctggc catgatgggc   960
gtgctcggct acatgccaac ctacctgcag atggtgcaca ccctgacgcc aactgaagca  1020
ggcttgatga tgatcccgat gatggtcggc atgatcggtg tctccactgg tgttggcttc  1080
atcatcgcta agaccggcaa ctacaagtac tacccatcg cgggcctggc catcacggcg  1140
tttgctttgt ggtggatgac ccagatgacc gttgagactt cattgaccgg tatcggagtt  1200
cgcttccttg tatacggtgt cggcttgggc tttgtcacgc aggtactggt gctgattgtt  1260
caaaactcct tccctgtatc gcaggtcggt actgccacgg cggctaataa cttcttccgc  1320
cagattggtt cggcattggg tgcttccatc gtgggttcga tgttcattca caaatgcag  1380
aatgagatgg ctaccgtttt gcctgatgcc cttgcatcgt tgggcaagga aggcgccgct  1440
atttcgcagc agttccaagg tgcagatgcc gccaactcct tgactccgca cgcagtcgca  1500
gagcttcccg atgtcctccg tgacgctatc ttaaattcct acaatgacgg tctgacccc   1560
gtgattggca tgatggtgcc actggccatt gttgcaatgc tgattttgtt cccactgcgc  1620
caagagcgct tgaaggaaac catcgaataa                                   1650
```

The invention claimd is:

1. A method for preparing 5'-inosine monophosphate, comprising culturing a microorganism of the genus Corynebacterium comprising a protein variant having activity of exporting 5'-inosine monophosphate or a polynucleotide encoding the protein variant in a medium; and recovering 5'-inosine monophosphate from the microorganism or medium, wherein the protein variant has at least 90% sequence identity to SEQ ID NO:2, and comprises one or more substitutions selected from the group consisting of: a substitution of the 123rd amino acid with cysteine, a substitution of the 243rd amino acid with valine, a substitution of the 387th amino acid with threonine, a substitution of the 405th amino acid with tyrosine, a substitution of the 413th amino acid with threonine, and a substitution of the 458th amino acid with lysine, or a combination thereof, in the amino acid sequence of SEQ ID NO: 2.

2. The method according to claim 1, wherein the protein variant further comprises a substitution of the 2nd amino acid with isoleucine, a substitution of the 64th amino acid with glutamic acid or aspartate, or a combination thereof.

3. The method according to claim 1, wherein the microorganism of the genus Corynebacterium is Corynebacterium stationis.

4. The method according to claim 2, wherein the microorganism of the genus Corynebacterium is Corynebacterium stationis.

* * * * *